United States Patent
Gouin et al.

(10) Patent No.: US 10,543,223 B2
(45) Date of Patent: Jan. 28, 2020

(54) MANNOSE DERIVATIVES USEFUL FOR TREATING PATHOLOGIES ASSOCIATED WITH ADHERENT E. COLI

(71) Applicants: ENTEROME, Paris (FR); CENTRE NATIONAL DE LA RECHERCHE SCIENTIFIQUE (CNRS), Paris (FR); UNIVERSITE CLERMONT AUVERGNE, Clermont Ferrand (FR); UNIVERSITE DE NANTES, Nantes (FR)

(72) Inventors: Sebastien Gouin, Thouare sur Loire (FR); Thibault Chalopin, Nantes (FR); Julie Bouckaert, Kortrijk (BE); Nicolas Barnich, Madriat (FR); Adeline Sivignon, Gerzat (FR); Dimitri Alexander Alvarez-Dorta, Nantes (FR); Francois Bellamy, Saulon la Rue (FR)

(73) Assignees: ENTEROME, Paris (FR); CENTRE NATIONAL DE LA RECHERCHE SCIENTIFIQUE, Paris (FR); UNIVERSITE CLERMONT AUVERGNE, Clermont Ferrand; UNIVERSITE DE NANTES, Nantes ( * ) Notice: Subject to any disclaimer, the term of this patent is extended or adjusted under 35 U.S.C. 154(b) by 0 days.

(21) Appl. No.: 15/750,471

(22) PCT Filed: Aug. 5, 2016

(86) PCT No.: PCT/EP2016/068813
§ 371 (c)(1),
(2) Date: Feb. 5, 2018

(87) PCT Pub. No.: WO2017/021549
PCT Pub. Date: Feb. 9, 2017

(65) Prior Publication Data
US 2018/0235991 A1 Aug. 23, 2018

(30) Foreign Application Priority Data
Aug. 5, 2015 (EP) .................................. 15306268

(51) Int. Cl.
A61K 31/7056 (2006.01)
A61K 45/06 (2006.01)
A61K 31/706 (2006.01)
A61P 31/04 (2006.01)

(52) U.S. Cl.
CPC ........ *A61K 31/7056* (2013.01); *A61K 31/706* (2013.01); *A61K 45/06* (2013.01); *A61P 31/04* (2018.01)

(58) Field of Classification Search
None
See application file for complete search history.

(56) References Cited

FOREIGN PATENT DOCUMENTS

EP         2690105 A1 *  1/2014 ............. C07H 15/26
WO    2014/016361 A1     1/2014

OTHER PUBLICATIONS

Meanwell, N. A. (2011). Synopsis of some recent tactical application of bioisosteres in drug design. Journal of medicinal chemistry, 54(8), 2529-2591. (Year: 2011).*
Almant, M., et al., Clustering of *Escherichia coli* Type-1 Fimbrial Adhesins by Using Multimeric Heptyl alpha-d-Mannoside Probes with a Carbohydrate Core, Chemistry, 2011, European Journal, 17(36:10029-10038.
Appeldoorn, C.C.M., et al, Novel Multvalent Mannose Compounds and Their Inhibition of the Adhesion of Type 1 Fimbriated Uropathogenic *E. coli*, Tetrahedron Asymmetry, 2005, 16:361-372.
(Continued)

*Primary Examiner* — Dale R Miller
(74) *Attorney, Agent, or Firm* — Pillsbury Winthrop Shaw Pittmann LLP

(57) ABSTRACT

The present invention relates to mannose derivatives of formula (I):

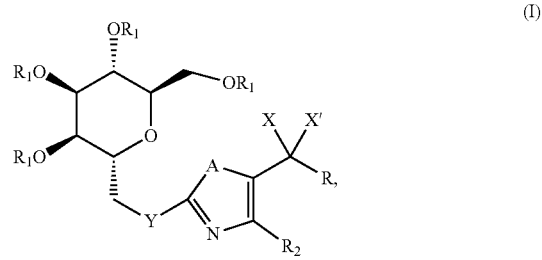

wherein
$R_1$ represents H, CO—$(C_1$-$C_6)$-alkyl or CO-alkylaryl,
Y represents a single bond, $CH_2$, O, $NR_3$, S,
A represents O, NH or S,
X represents H and X' represents OH or X and X' taken together with the carbon atom bearing them form a CO group,
$R_2$ represents H, a linear or branched $(C_1$-$C_6)$-alkyl or $CF_3$,
$R_3$ represents H, a $C_1$-$C_6$ alkyl, a CO—$(C_1$-$C_6)$-alkyl, $CF_3$ or $COCF_3$, and
R is as described in claim 1.
The mannose derivatives of formulae (I) are useful for treating pathologies associated with the presence of adherent *Escherichia coli* (AEC), in particular inflammatory bowel diseases (IBD), such as Crohn's disease and ulcerative colitis; a urinary tract infection, in particular painful bladder syndrome and cystitis, more particularly interstitial cystitis; irritable bowel syndrome; metabolic diseases such as metabolic obesity, diabetes, hypercholesterolemia; autoimmune inflammatory diseases; and colorectal cancer, in particular colon cancer.

20 Claims, 9 Drawing Sheets

(56) References Cited

OTHER PUBLICATIONS

Barghash, R., et al., Synthesis of Thiourea-Tethered C-Glycosyl Amino Acids via Isothiocyanate-Amine Coupling, Org. Biomol. Chem., 2009, 7:3319-3330.

Barnich, N., et al., CEACAM6 Acts as a Receptor for Adherent-Invasive *E. coli*, Supporting Ileal Mucosa Colonization in Crohn Disease, J. Clin. Invest, 2007, 117:1566-1574.

Bonnet, M., et al., Colonization of the Human Gut by *E. coli* and Colorectal Cancer Risk, Clin. Cancer Research 2014, 20:859-867.

Bouckaert, J., et al., Receptor Binding Studies Disclose a Novel Class of High-Affinity Inhibitors of the *Esherichia coli* FimH Adhesin, Mol. Microbial., 2005, 55: 441-455.

Bouckaert, J., et al., The Affinity of the FimH Fimbrial Adesin is Receptor-Driven and Quasi-Independent of *Escherichia coli* Pathotypes, Mol. Microbial., 2006, 61:1556-1568.

Bouckaert, J., et al., Heptyl-alpha-D-Mannosides Grafted on a Beta-Cyclodextrin Core to Interfere with *Escherichia coli* Adhesion: An In Vivo Multivalent Effect, Chemistry, a European Journal, 2013, 19:7847-7855.

Boudeau, J., et al., Invasive Ability of an *Escherichia coil* Strain Isolated from the Ileal Mucosa of a Patient with Crohn's Disease, Infect. Immun., 1999, 67,(9):4499-4509.

Bronowski, C., et al., A Subset of mucosa-Associated *Escherichia coli* Isolates from Patients with Colon Cancer, But Not Crohn's Disease, Share Pathogenicity Islands With Urinary Pathogenic *E. Coli*, Microbiology, 2008, 154:571-583.

Brument, S., et al., Thiazolylaminomannosides as Potent Antiadhesives of Type 1 Piliated *Escherichia coli* Isolated from Crohn's Disease Patients, Journal of Medicinal Chemistry, 2013, 56(13):5395-5406.

Chen, S.L., et al., Positive Selection Identifies an in vivo Role for FimH During Urinary Tract Infection in Addition to Mannose Binding, PNAS, 2009, 106(52):22439-22444.

Cho, J.H., et al., Recent Insights into the Genetics of Inflammatory Bowel Disease, Gastroenterology, 2011, 140(6):1704-12. doi: 10.1053/j.gastro.2011.02.046.

Darfeuille-Michaud, A., et al., High Prevalence of Adherent-Invasive *Escherichia coli* Associated With Ileal Mucosa in Crohn's Disease, Gastroenterology 2004, 27(2):412-421.

Dreux, N., et al., Point Mutations in FimH Adhesin of Crohn's Disease-Associated Adherent-Invasive *Escherichia coli* Enhance Intestinal Inflammatory Response, PLOS Pathogens, 2013, 9(1):e1003141.

d'Halluin M., et al., Graphite-Supported Ultra-Small Copper Nanoparticles—Preparation, Characterization and Catalysis Applications, Carbon, 2015, 93:974-983.

Liu, L., et al., A Focused Sulfated Glycoconjugate Ugi Library for Probing Heparan Sulfate-Binding Angiogenic Growth Factors, Bioorg. Med. Chem. Lett., 2012, 22(19):6190-6194.

Mansfield, C.S., et al., Remission of Histiocytic Ulcerative Colitis in Boxer Dogs Correlates with Eradication of Invasive Intramucusal *Escherichia coli*, J. Vet. Intern. Med., 2009, 23:964-969.

Martin, H.M., et al., Enhanced *Escherichia coli* Adherence and Invasion in Crohn's Disease and Colon Cancer, Gastroenterology, 2004, 27:80-93.

Martinez-Medina, M., et al., Molecular Diversity of *Escherichia coli* in the Human Gut: New Ecological Evidence Supporting the Role of Adherent-Invasive *E. coli* (AIEC) in Crohn's Disease, Inflammatory Bowel Dis., 2009, 15(6):872-882.

Martinez-Medina, M., et al., Adherent-Invasive *Escherichia coli* Phenotype Displayed by Intestinal Pathogenic *E. coli* Strains from Cats, Dogs, and Swine, Applied and Environmental Microbiology, 2011, 77(16):5813-5817.

Martinez-Medina, M., et al., Western Diet Induces Dysbiosis With Increased *E. coli* in CEABAC10 Mice, Alters Host Barrier function Favouring AIEC Colonisation, Gut, 2014, 63:116-124. doi :10.1136/gutjnl-2012-304119.

Martinez-Medina, M., et al., *Escherichia coli* in Chronic Inflammatory Bowel Diseases: An Update on Adherent Invasive *Escherichia coli* Pathogenicity, World J. Gastrointest. Pathophysiology, 2014, 5(3): 213-227.

Molodecky, N.A., et al., Increasing Incidence and Prevalence of the Inflammatory Bowel Diseases With Time, Based on Systematic Review, Gastroenterology, 2012, 142:46-54.

Raisch, J., et al., Colon Cancer-Associated B2 *Escherichia coli* Colonize Gut Mucosa and Promote Cell Proliferation, World J. Gastroenterology ,2014, 20(21):6560-6572.

Schwardt, O., et al., Design, Synthesis and Biological Evaluation of Mannosyl Triazoles as FimH Antagonists, Bioorganic & Medicinal Chemistry, 2011, 9:6454-6473.

Sobieszczanska, B., et al., Virulence Genes Profiles and Phylogenetic Origin of *Escherichia coli* from Acute and Chronic Intestinal Diseases Revealed by Comparative Genomic Hybridization Microarray, Polish Journal of Microbiology, 2012, 61(2):105-110.

Wellens, A., et al., Intervening with Urinary Tract Infections Using Anti-Adhesives Based on the Cystal Structure of the FimH-Oligomannose-3 Complex, PLoS ONE,2008, 3(4):e2040.

* cited by examiner

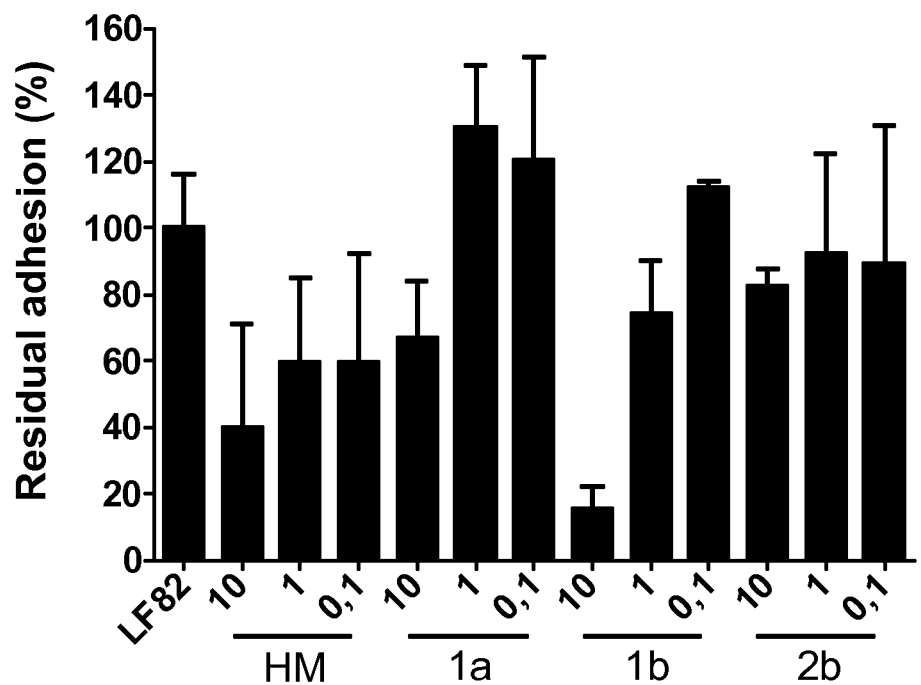
Figure 5 (Pre-incubation at different concentrations, μM)
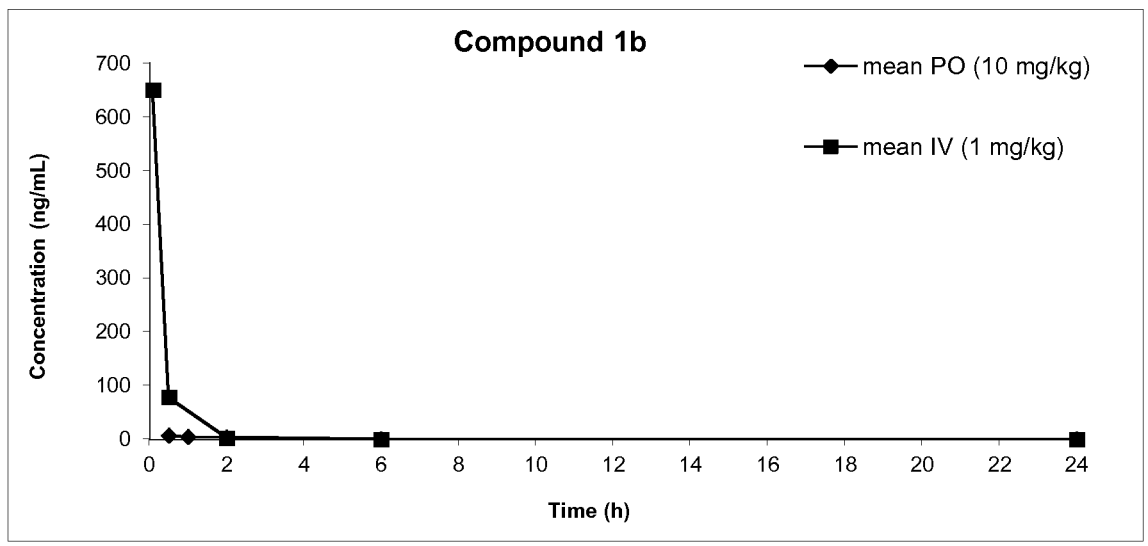
Figure 6

MANNOSE DERIVATIVES USEFUL FOR TREATING PATHOLOGIES ASSOCIATED WITH ADHERENT E. COLI

RELATED APPLICATIONS

This application is the National Phase of International Application No. PCT/EP2016/068813, filed Aug. 5, 2016 which designated the U.S. and that International Application was published under PCT Article 21(2) in English, and claims priority to European Application Serial No. 15306268.2, filed Aug. 5, 2015, all of which applications are expressly incorporated herein by reference in their entirety.

FIELD OF THE INVENTION

The present invention relates to mannose derivatives useful for treating pathologies associated with Adherent *Escherichia coli* (AEC), and pharmaceutical and veterinary compositions containing them. The present invention further relates to a method for preparing said mannose derivatives.

BACKGROUND OF THE INVENTION

The gut microbiota plays an important role in several diseases, as gut microbiota lies at the interface with the gut, the host immune system and the environment. A typical human gut microbiota comprises thousands of microbial species, among which commensal, beneficial or pathogenic bacteria. The role of each of these microorganisms is hardly described; however it is known they change their behavior in diseased individuals in favor of the pathogenic potential of certain commensal bacteria. The microbial content of the gut is believed to weigh about 1.5 kg and to outnumber the cells of the host by 10 to 1. Inflammatory bowel diseases are characterized by an aberrant immune response occurring in a genetically predisposed host in response to microbes and/or microbial compounds found in the gut microbiota.

Crohn's disease (CD) is a chronic inflammatory bowel disease (IBD) that may affect any part of the gastrointestinal tract from mouth to anus. The age of onset is generally between 15-30 years and it is equally prevalent in women and men. The highest prevalence is found in Europe and North America with just over 300 per 100.000 persons (Molodecky et al. 2012). CD generally leads to abdominal pain, severe diarrhea and weight disorders. The disease is of unknown aetiology and multifactorial: environmental factors, host genetics and gut microbiome have all been shown to impact the risk of disease and its severity (Cho et al (2011)). The clinical diagnosis of CD is supported by serologic, radiologic, endoscopic, and histologic findings.

Ulcerative colitis (or UC) is another form of inflammatory bowel disease (IBD). Ulcerative colitis is a form of colitis, a disease of the colon (the largest portion of the large intestine), that includes characteristic ulcers, or open sores. The main symptom of active disease is usually constant diarrhea mixed with blood, of gradual onset. Ulcerative colitis has the same etiology as CD, but CD can affect the whole gastrointestinal tract while UC only attacks the large intestine.

Of the bacteria that may play a role in the pathogenesis of these diseases, a pathotype of *E. coli*, called "AIEC" for "adherent-invasive *Escherichia coli*", has been strongly implicated (see in particular Boudeau et al., 1999). AIEC are able to adhere to the intestinal epithelium and colonize gut mucosa where they participate to IBD onset. More precisely, AIEC were found to be associated with ileal mucosa in 36.4% of CD patients compared with 6.2% of controls, suggesting that these bacteria are involved in CD pathogenesis (Darfeuille-Michaud et al., 2004).

AIEC are distinct from other pathogenic intestinal *E. coli* strains because they do not harbor genes typically associated with pathogens such as enterotoxigenic, enterohemorrhagic, enteroinvasive, enteroaggregative, and enteropathogenic *E. coli* (Boudeau J et al, 1999).

AIEC's adhesion to mucosal epithelial cells is mediated by proteinaceous, rod-like organelles that are called type-1 fimbriae. Type-1 fimbriae carry an adhesin at the edge of a flexible tip fibrillum. This adhesin, FimH, is a lectin having a strong affinity for highly mannosylated glycoproteins (Bouckaert J et al, 2006).

Via FimH, AIEC bacteria adhere specifically to the carcinoembryonic antigen-related cell adhesion molecule 6 (CEACAM6), a mannosylated glycoprotein which is abnormally expressed in the ileal mucosa of 35% of CD patients (Barnich N et al, 2007). Overexpression of these CEACAM6 molecules in CD patients, acting as receptors for *E. coli* adhesion in the gut, favors ileal and colonic AIEC invasion and their intracellular survival and replication within the mucosal tissues, thereby amplifying immune responses in IBD patients.

Moreover, it has been shown that point and pathoadaptative mutations in the FimH adhesin confer significantly higher ability to adhere to CEACAM-expressing intestinal epithelial cells, thus leading to an abnormal colonization of the gut and to the development of chronic inflammation in a host (Dreux et al, 2013).

AIECs have also been demonstrated to be implicated in inflammatory bowel diseases of animals such as dogs and cats, in particular in connection with animals suffering from CD or from granulomatous colitis (also called histiocytic ulcerative colitis), a disease close to the corresponding human ulcerative colitis (Bronowski et al, 2008; Martinez-Medina et al, 2011; Mansfield et al, 2009 and Martinez-Medina et al, 2014).

As patients suffering from an inflammatory bowel disease have a five-fold increased risk of developing colorectal cancer (CRC), AIECs are strongly suspected to be involved in the pathogenesis of CRC. Already, *E. coli* strains with similar features to AIECs, and belonging to the B2 and D phylogenetic groups, have been associated with CRC, in particular *E. coli* strains exhibiting adhesion properties to the ileal and colonic mucosa (Martin et al, 2004; Raisch et al, 2014; and Bonnet et al., 2014).

Such Adherent *E. coli* (AEC) have also been demonstrated to be involved in auto-immune inflammatory diseases such as celiac disease. In particular, AIECs are suspected to play an important role in the onset of celiac disease (Martinez-Medina et al 2, 2014).

AEC are also suspected to be involved in inflammatory bowel syndrome (Sobieszczanska et al, 2012), and in metabolic diseases such as metabolic syndrome, obesity, diabetes (type 1 or 2), hypercholesterolemia (see in particular Martinez-Medina et al 1, 2014).

Finally, extraintestinal *E. coli* strains largely sharing characteristic features of AIECs have been found to cause urinary tract infections (UTIs). These *E. coli* strains, called UPECs (UroPathogenic *E. coli*), specifically bind to uroplakin 1a on the bladder epithelium, which results in bacteria invasion of the bladder mucosa, via phenomena similar to those described in case of ileal and colonic AIEC invasion (Chen et al, 2009; Bronowski et al, 2008).

As AIECs, UPECs and AECs invasiveness, anti-phagocytic and pro-inflammatory properties have been demonstrated to be involved in UTIs and are likely to be involved in IBD (in humans as well as in animals), IBS, CRC and auto-immune diseases (such as celiac disease) onset, this is of crucial importance to elaborate a strategy to eradicate these different bacteria from the digestive and/or urinary tract.

A promising strategy to prevent and treat the above pathologies would be to inhibit the adhesion of AIECs, UPECs and AECs to the epithelial cells of the digestive and/or urinary tract mucosa.

To date, heptylmannose (HM) is still one of the most efficient FimH antagonists and a potent in vitro AIEC and UPEC adhesion inhibitor (Bouckaert et al, 2005, Bouckaert et al, 2013). HM is generally used as a reference in the antiadhesive assays but proved disappointing in vivo. Indeed, millimolar concentrations are required to observe a significant bacterial load reduction in a cystitis murine model (Wellens et al, 2008) and gave no effect with AIEC in a CEABAC 10 Crohn's disease model.

To improve the therapeutic effect of HM, WO 2014/016361 proposed in particular mannose derivatives of formula (IV) and (IV'), which all possess a heteroatom (NH) link between the anomeric carbon of the mannose moiety and the aromatic aglycon. A hydrocarbon link was not envisaged as it was expected to change the overall conformation of the mannose moiety (a $^1C_4$ chair conformation is indeed expected in such derivatives, see Schwardt et al, 2011), thus preventing the required interactions to occur between the FimH adhesin and the mannose moiety of the carbon analogs of the compounds of formula (IV) and (IV') of WO 2014/016361, resulting in a lower affinity of the compounds. Additionally, the crystallographic structure of a compound of formula IV in the FimH binding site showed a stabilizing hydrogen bond between the anomeric NH and a water molecule (Brument et al, 2013). This interaction is precluded when switching the NH group for a $CH_2$.

Surprisingly however, the present inventors discovered that mannose derivatives with a hydrocarbon link between the anomeric carbon of the mannose moiety and the aglycon proved very efficient in inhibiting the interaction between FimH and its receptor (CEACAM6 in the intestine or uroplakin 1a in urinary tract). Said compounds proved also stable under acidic conditions comparable to the ones encountered in the stomach, and are little or not sensitive to hydrolysis by glycosidases, in particular intestinal glycosidases, two properties required for further clinical developments.

SUMMARY OF THE INVENTION

A first aspect of the present invention encompasses a compound of formula (I):

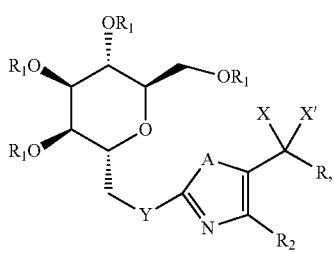

(I)

wherein $R_1$ represents H, CO—$(C_1-C_6)$-alkyl or CO-alkylaryl, preferably H, COMe or $COCH_2Ph$, Y represents a single bond, $CH_2$, O, $NR_3$, S, preferably a single bond, $CH_2$, $NR_3$, S, A represents O, NH or S, preferably O or S, X represents H and X' represents OH or X and X' taken together with the carbon atom bearing them form a CO group, $R_2$ represents H, a linear or branched $(C_1-C_6)$-alkyl or $CF_3$, $R_3$ represents H, a $C_1-C_6$ alkyl, a CO—$(C_1-C_6)$-alkyl, $CF_3$ or $COCF_3$, preferably H, $CH_3$, $COCH_3$, $CF_3$ or $OCF_3$, and R represents: a $(C_1-C_6)$-alkyl, a $(C_2-C_6)$-alkenyl, a $(C_2-C_6)$-alkynyl, a $(C_3-C_{10})$-cycloalkyl, a $(C_5-C_{10})$-cycloalkenyl, a heterocycloalkyl, a heterocycloalkenyl, an aryl, an alkyl aryl, $CF_3$, adamantyl, $OR_a$, or $NR_bR_c$, wherein $R_a$ represents H, a $(C_1-C_6)$-alkyl, a $(C_2-C_6)$-alkenyl, a $(C_2-C_6)$-alkynyl, a $(C_3-C_6)$-cycloalkyl, a $(C_3-C_6)$-cycloalkenyl, a heterocycloalkyl, a heterocycloalkenyl, an aryl, a alkylaryl, a CHO, a CO—$(C_1-C_6)$-alkyl, or CO-aryl, a $CO_2H$, a $CO_2$—$(C_1-C_6)$-alkyl, or a CONH—$(C_1-C_6)$-alkyl, and wherein $R_b$ and $R_c$ represent independently from each other any of the groups defined for $R_a$, $R_b$ representing in particular H, said $(C_1-C_6)$-alkyl, $(C_2-C_6)$-alkenyl, $(C_2-C_6)$-alkynyl, $(C_3-C_{10})$-cycloalkyl, $(C_5-C_{10})$-cycloalkenyl, heterocycloalkyl, heterocycloalkenyl, CO—$(C_1-C_6)$-alkyl, $CO_2$—$(C_1-C_6)$-alkyl, CONH—$(C_1-C_6)$-alkyl, aryl, alkylaryl, CO-aryl and CO-alkylaryl being optionally substituted by one or more, preferably 1 to 4, more preferably 1 or 2 substituent(s) R', each independently selected from:

a $(C_1-C_6)$-alkyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ represents independently H, a $(C_1-C_6)$-alkyl (preferably H or $CH_3$), T represents a monovalent cation such as a mineral monovalent cation, in particular an alkaline cation preferably selected from $Li^+$, $Na^+$, $K^+$, and even more preferable $Na^+$, and wherein T' is a monovalent anion, such as a halogenide, in particular chloride, bromide or iodide, preferably chloride, a $(C_2-C_6)$-alkenyl, a $(C_2-C_6)$-alkynyl, a $(C_3-C_{10})$-cycloalkyl, a $(C_5-C_{10})$-cycloalkenyl, a heterocycloalkyl, a heterocycloalkenyl, an aryl, optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ T and T' are as defined above, an alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ T and T' are as defined above, a NH-alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ T and T' are as defined above, a CHO,
a CO—($C_1$-$C_6$)-alkyl optionally substituted by a halogen such as fluorine or a carbohydrate,
a CO-aryl optionally substituted by one or more, preferably one to three substituents selected from a halogen, $NH_2$, OH, $CF_3$, a $C_1$-$C_6$ alkyl preferably substituted by a carbohydrate, $CH_2SO_3T$, $CH_2COOT$ or $N(R_g)_3T'$, wherein $R_g$ T and T' are as defined above,
a $CO_2H$,
a $CO_2$—($C_1$-$C_6$)-alkyl,
a CONH—($C_1$-$C_6$)-alkyl,
a CONH-aryl or NHCO-aryl optionally substituted by one or more, preferably one to three substituents selected from a halogen, $NH_2$, OH, $CF_3$, a $C_1$-$C_6$ alkyl preferably substituted by a carbohydrate, $CH_2SO_3T$, $CH_2COOT$ or $N(R_g)_3T'$, wherein $R_g$ T and T' are as defined above,
a halogen,
$CF_3$,
$OR_d$, wherein $R_d$ represents: H, a ($C_1$-$C_6$)-alkyl, a ($C_3$-$C_{10}$)-cycloalkyl, CO—($C_1$-$C_6$)-alkyl, or CO-aryl optionally substituted by one or more, preferably one to three substituents selected from a halogen, $CF_3$, a $C_1$-$C_6$ alkyl preferably substituted by a carbohydrate,
$NR_eR_f$, wherein $R_e$ and $R_f$ represent independently from each other: H, a ($C_1$-$C_6$)-alkyl, a ($C_3$-$C_{10}$)-cycloalkyl, CO—($C_1$-$C_6$)-alkyl, or CO-aryl optionally substituted by one or more, preferably one to three substituents selected from a halogen, $CF_3$, a $C_1$-$C_6$ alkyl preferably substituted by a carbohydrate,
$NHR_b$, wherein $R_b$ is as defined above,
$NO_2$,
CN, and
$CH_2SO_3T$, $CH_2COOT$ or $N(R_g)_3T'$, wherein $R_g$ T and T' are as defined above, or a pharmaceutically acceptable salt or solvate thereof.

According to another aspect, the present invention relates to a pharmaceutical or veterinary composition comprising a compound of formula (I) as described above as active substance, and a pharmaceutically or veterinary acceptable carrier.

According to another aspect, the present invention encompasses the compounds of formula (I) and the compositions of the invention for use as medicament, in particular for the treatment of pathologies caused by Adherent *Escherichia coli* and mediated by interactions between Adherent *Escherichia coli* lectins, such as FimH adhesin, and host cell surface glycans.

According to another aspect, the present invention relates to a kit comprising:
the composition of the invention, and
a second composition comprising another therapeutic compound,
as a combination product for simultaneous, separate and staggered use for treating pathologies caused by Adherent *Escherichia coli* and mediated by interactions between Adherent *Escherichia coli* lectins, such as FimH adhesin and host cell surface glycans.

According to another aspect, the present invention encompasses methods for preparing the compounds of formula (I).

DETAILED DESCRIPTION OF THE INVENTION

The present invention relates to compounds that inhibit the interaction of type I pili of Adherent *E. Coli* with its receptor epithelial cells, and which are thus useful for the treatment of pathologies associated with AEC colonization of mucosa epithelial cells, such as gut, ileal or urinary tract mucosa.

As understood in the present invention, Adherent *E. coli* (AEC) are intestinal and extraintestinal (in particular urinary) pathogenic *E. coli* strains belonging to the B2 and D phylogenic group, exhibiting adhesion properties to the mucosal epithelial cells. Said AEC preferably possess at least one proteinaceous, rod-like organelles that are called type-1 fimbriae carrying an adhesin called FimH at the edge of a flexible tip fibrillum, said adhesin having a strong affinity for highly mannosylated glycoproteins. Via FimH, intestinal AEC bacteria adhere specifically to the carcinoembryonic antigen-related cell adhesion molecule 6 (CEACAM6), while extraintestinal AEC adhere specifically to other extraintestinal receptor, such as uroplakin 1a in the case of UPEC. AEC include in particular adherent-invasive *E. coli* such as the known UPECs and AIECs.

Compounds of Formula (I)

One aspect of the invention is a compound of Formula (I):

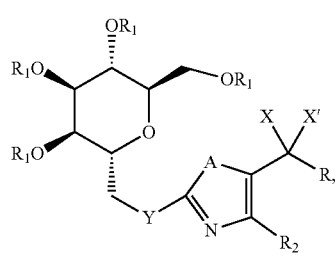

wherein
$R_1$ represents H, CO—($C_1$-$C_6$)-alkyl or CO-alkylaryl, preferably H, COMe or $COCH_2Ph$,
Y represents a single bond, $CH_2$, O, $NR_3$, S, preferably a single bond, $CH_2$, $NR_3$, S,
A represents O, NH or S, preferably O or S,
X represents H and X' represents OH or X and X' taken together with the carbon atom bearing them form a CO group,
$R_2$ represents H, a linear or branched ($C_1$-$C_6$)-alkyl or $CF_3$,
$R_3$ represents H, a $C_1$-$C_6$ alkyl, a CO—($C_1$-$C_6$)-alkyl, $CF_3$ or $COCF_3$, preferably H, $CH_3$, $COCH_3$, $CF_3$ or $OCF_3$, and
R represents: a ($C_1$-$C_6$)-alkyl, a ($C_2$-$C_6$)-alkenyl, a ($C_2$-$C_6$)-alkynyl, a ($C_3$-$C_{10}$)-cycloalkyl, a ($C_5$-$C_{10}$)-cycloalkenyl, a heterocycloalkyl, a heterocycloalkenyl, an arylan alkyl aryl, $CF_3$, adamantyl, $OR_a$, or $NR_bR_c$,
wherein $R_a$ represents H, a ($C_1$-$C_6$)-alkyl, a ($C_2$-$C_6$)-alkenyl, a ($C_2$-$C_6$)-alkynyl, a ($C_3$-$C_6$)-cycloalkyl, a ($C_3$-$C_6$)-cycloalkenyl, a heterocycloalkyl, a heterocycloalkenyl, an aryl, a alkylaryl, a CHO, a CO—($C_1$-$C_6$)-alkyl, or CO-aryl, a $CO_2H$, a $CO_2$—($C_1$-$C_6$)-alkyl, or a CONH—($C_1$-$C_6$)-alkyl,
and wherein $R_b$ and $R_c$ represent independently from each other any of the groups defined for $R_a$, $R_b$ representing in particular H,
said ($C_1$-$C_6$)-alkyl, ($C_2$-$C_6$)-alkenyl, ($C_2$-$C_6$)-alkynyl, ($C_3$-$C_{10}$)-cycloalkyl, ($C_5$-$C_{10}$)-cycloalkenyl, heterocycloalkyl, heterocycloalkenyl, CO—($C_1$-$C_6$)-alkyl, $CO_2$—($C_1$-$C_6$)-alkyl, CONH—($C_1$-$C_6$)-alkyl, aryl, alkylaryl, CO-aryl and CO-alkylaryl being optionally substituted by one or more, preferably 1 to 4, more preferably 1 or 2 substituent(s) R', each independently selected from:
- a $(C_1-C_6)$-alkyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ represents independently H, a $(C_1-C_6)$-alkyl (preferably H or $CH_3$), T represents a monovalent cation such as a mineral monovalent cation, in particular an alkaline cation preferably selected from $Li^+$, $Na^+$, $K^+$, and even more preferable $Na^+$, and wherein T' is a monovalent anion, such as a halogenide, in particular chloride, bromide or iodide, preferably chloride,
- a $(C_2-C_6)$-alkenyl,
- a $(C_2-C_6)$-alkynyl,
- a $(C_3-C_{10})$-cycloalkyl,
- a $(C_5-C_{10})$-cycloalkenyl,
- a heterocycloalkyl,
- a heterocycloalkenyl,
- an aryl, optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- an alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- a NH-alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- a CHO,
- a $CO-(C_1-C_6)$-alkyl optionally substituted by a halogen such as fluorine or a carbohydrate,
- a CO-aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- a $CO_2H$,
- a $CO_2-(C_1-C_6)$-alkyl,
- a $CONH-(C_1-C_6)$-alkyl,
- a CONH-aryl or NHCO-aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- a halogen,
- $CF_3$,
- $OR_d$, wherein $R_d$ represents: H, a $(C_1-C_6)$-alkyl, a $(C_3-C_{10})$-cycloalkyl, $CO-(C_1-C_6)$-alkyl, or CO-aryl optionally substituted by one or more, preferably one to three substituents selected from a halogen, $CF_3$, a $C_1-C_6$ alkyl preferably substituted by a carbohydrate,
- $NR_eR_f$, wherein $R_e$ and $R_f$ represent independently from each other: H, a $(C_1-C_6)$-alkyl, a $(C_3-C_{10})$-cycloalkyl, $CO-(C_1-C_6)$-alkyl, or CO-aryl optionally substituted by one or more, preferably one to three substituents selected from a halogen, $CF_3$, a $C_1-C_6$ alkyl preferably substituted by a carbohydrate,
- $NHR_b$, wherein $R_b$ is as defined above,
- $NO_2$,
- CN, and
- $CH_2SO_3T$, $CH_2COOT$ or $N(R_g)_3T'$, wherein $R_g$, T and T' are as defined above, or a pharmaceutically acceptable salt or solvate thereof.

Compounds of formula (I) wherein X represents H and X' represents OH are hypothesized to be metabolites of compounds of formula (I) wherein X and X' taken together with the carbon atom bearing them form a CO group.

Preferably, X and X' taken together with the carbon atom bearing them form a CO group.

In a preferred embodiment, $R_1$ represents H.

In another embodiment, $R_1$ represents $CO-(C_1-C_6)$-alkyl or CO-alkylaryl, preferably H, COMe or $COCH_2Ph$ (benzoyl). Without wishing to be bound by theory, in this embodiment, the compounds of the invention are considered as prodrugs. Indeed, it is assumed that substituents $R_1$ are deprotected in vivo, thus leading to compounds of formula (I) wherein $R_1$ is H, which actually bind to the adhesin FimH.

In a particular embodiment, X and X' taken together with the carbon atom bearing them forms a CO group and $R_1$ represents H.

Preferably, A represents S.

Advantageously, $R_3$ represents H, a linear or branched $(C_1-C_4)$-alkyl or $CF_3$, preferably H.

In a particular embodiment, A represents S and $R_2$ represents H. In another particular embodiment, X and X' taken together with the carbon atom bearing them forms a CO group, $R_1$ represents H, A represents S and $R_2$ represents H.

Advantageously, Y represents a single bond, $CH_2$, $NR_3$ or S, preferably Y represents a single bond or $NR_3$ with $R_3$ as defined above, even more preferably a single bond or NH.

Advantageously, R represents a $(C_1-C_6)$-alkyl, a heterocycloalkyl, a heterocycloalkenyl, an aryl, an alkyl aryl, $CF_3$, admantyl, $OR_a$, or $NHR_a$, wherein $R_a$ represents H, a $(C_1-C_6)$-alkyl, a cycloalkyl, a heterocycloalkyl, an aryl, or a alkylaryl, said $(C_1-C_6)$-alkyl, heterocycloalkyl, heterocycloalkenyl, aryl, and alkyl aryl being optionally substituted by one or more, in particular 1, 2, 3 or 4 substituent(s) R', as defined above or below, preferably 2 substituents R'.

Typically, R' represents:
- a $(C_1-C_6)$-alkyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$ represents independently H, a $(C_1-C_6)$-alkyl (preferably H or $CH_3$), T represents a monovalent cation such as a mineral monovalent cation, in particular an alkaline cation preferably selected from $Li^+$, $Na^+$, $K^+$, and even more preferable $Na^+$, and wherein T' is a monovalent anion, such as a halogenide, in particular chloride, bromide or iodide, preferably chloride,
- a $(C_3-C_6)$-cycloalkyl,
- a heterocycloalkyl,
- a heterocycloalkenyl,
- an aryl, optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above,
- an alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, a CHO, a CO—$(C_1-C_6)$-alkyl optionally substituted by a halogen such as fluorine, a CO-aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, a $CO_2H$, a $CO_2$—$(C_1-C_6)$-alkyl, a CONH—$(C_1-C_6)$-alkyl, a NHCO-aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, a NH-alkyl aryl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, a halogen, $CF_3$, $OR_d$, wherein $R_d$ represents: H, a $(C_1-C_6)$-alkyl, $NR_eR_f$, wherein $R_e$ and $R_f$ represent independently from each other: H, or a $(C_1-C_6)$-alkyl, $NHR_b$, wherein $R_b$ is as defined above, $NO_2$, and

CN.

In particular, R may represent methyl, ethyl, isopropyl, tert-butyl, phenyl, pyrrolyl, thiophenyl, naphthalenyl, pyridinyl, thiazolyl, phthalimidyl, benzothiazinonyl, isoxazolyl, benzothiazolyl, oxindolyl, chromen-2-onyl, benzyl, $CF_3$, O-methyl, O-isopropyl, NH-methyl, or NH-isopropyl, preferably a methyl, a thiazolyl or a chromen-2-only, said methyl, phenyl, pyrrolyl, thiophenyl, naphthalenyl, pyridinyl, thiazolyl, phthalimidyl, benzothiazinonyl, isoxazolyl, benzothiazolyl, oxindolyl, chromen-2-onyl and benzyl being optionally substituted (preferably on the aromatic or heteroaromatic ring in case of an aryl group) by one or more, in particular 1, 2, 3, or 4, preferably 1 or 2 substituent(s) R', as defined above or below, and in particular selected from:

a halogen (in particular bromine or chlorine or fluorine), or $CF_3$, $NH_2$, OH, $CF_3$, a methyl or ethyl optionally substituted by a carbohydrate, $NH_2$, OH, $CF_3$, $CH_2SO_3T$, $CH_2COOT$ or $N(R_g)_3T'$, wherein $R_g$ represents independently H, a $(C_1-C_6)$-alkyl (preferably H or $CH_3$), T represents a monovalent cation such as a mineral monovalent cation, in particular an alkaline cation preferably selected from $Li^+$, $Na^+$, $K^+$, and even more preferable $Na^+$, and wherein T' is a monovalent anion, such as a halogenide, in particular chloride, bromide or iodide, preferably chloride, phenyl optionally substituted by 1 to 4 halogen atoms (such as chlorine or fluorine) or $CF_3$, triazolyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, NHCO-phenyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, NH—$(C_2-C_6)$-alkynyl, NH-methyltriazolyl optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, thiazolyl (preferably 1,3-thiazolyl) optionally substituted by one or more, preferably one to three substituents selected from a halogen, $NH_2$, OH, $CF_3$, a $C_1-C_6$ alkyl preferably substituted by a carbohydrate, $CH_2SO_3T$, $CH_2COOT$ or $N(R_g)_3T'$, wherein $R_g$, T and T' are as defined above, pyrazinyl, O-methyl, O-isopropyl, NH-methyl, NH-isopropyl, $CO_2$-ethyl, $CO_2H$, CN and $NO_2$.

Specifically, R may represent: methyl, phenyl,

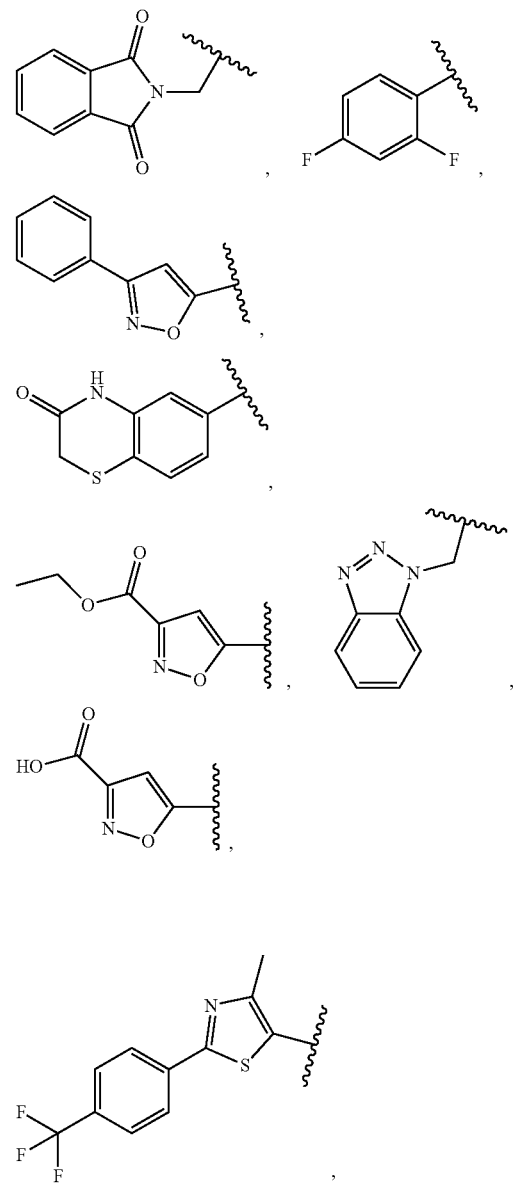

-continued
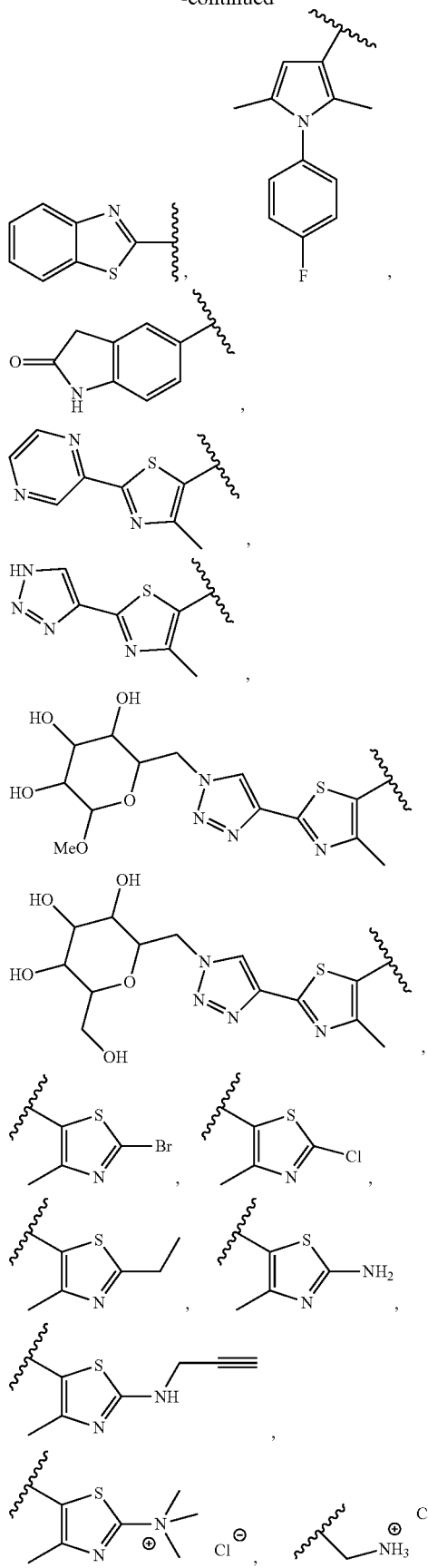
-continued
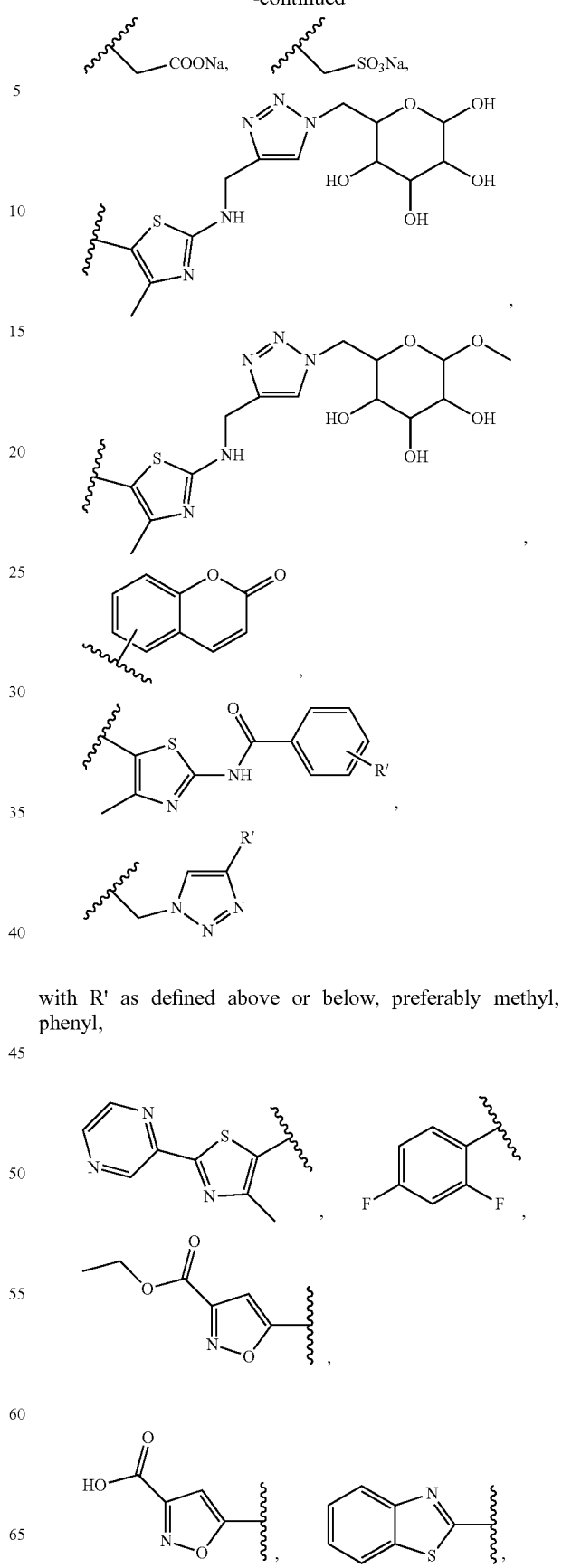
with R' as defined above or below, preferably methyl, phenyl,

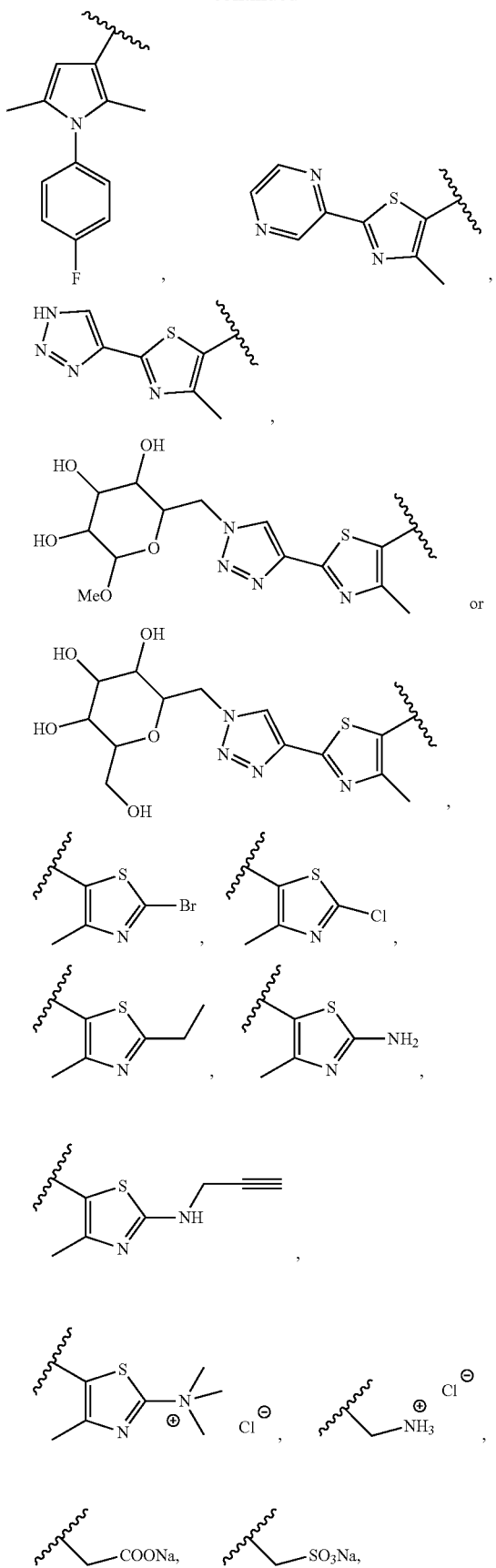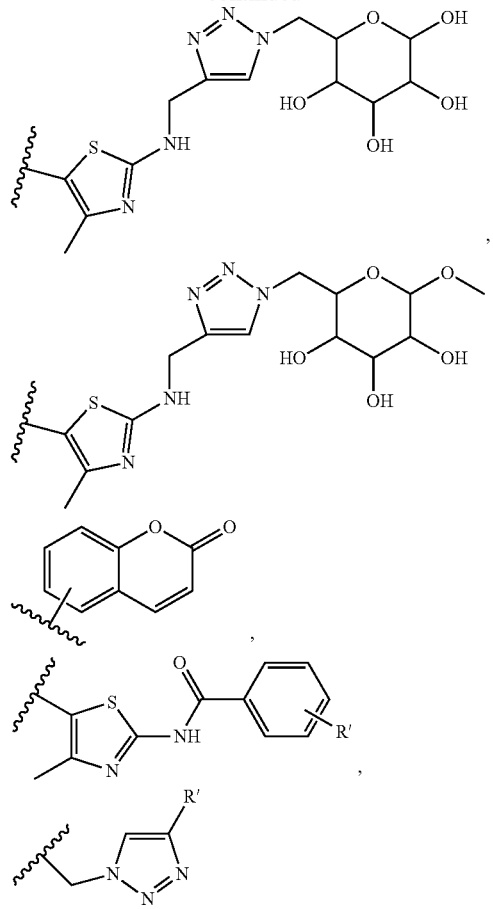
with R' as defined above or below, more preferably methyl,
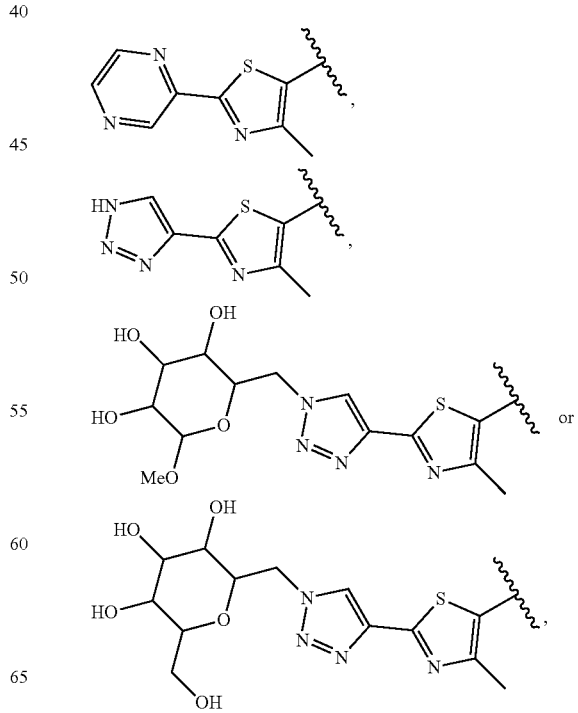

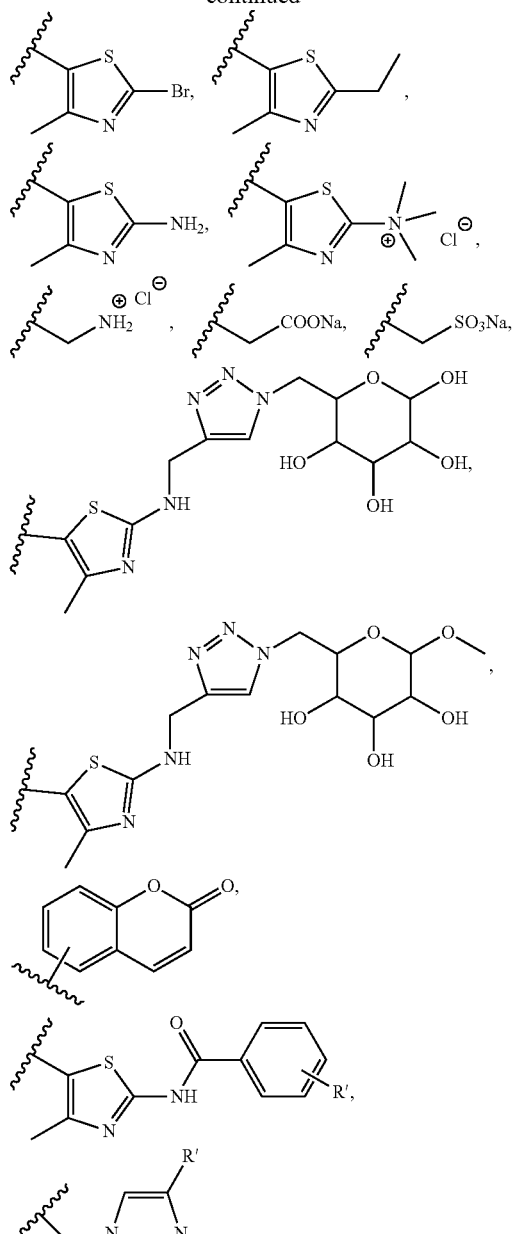
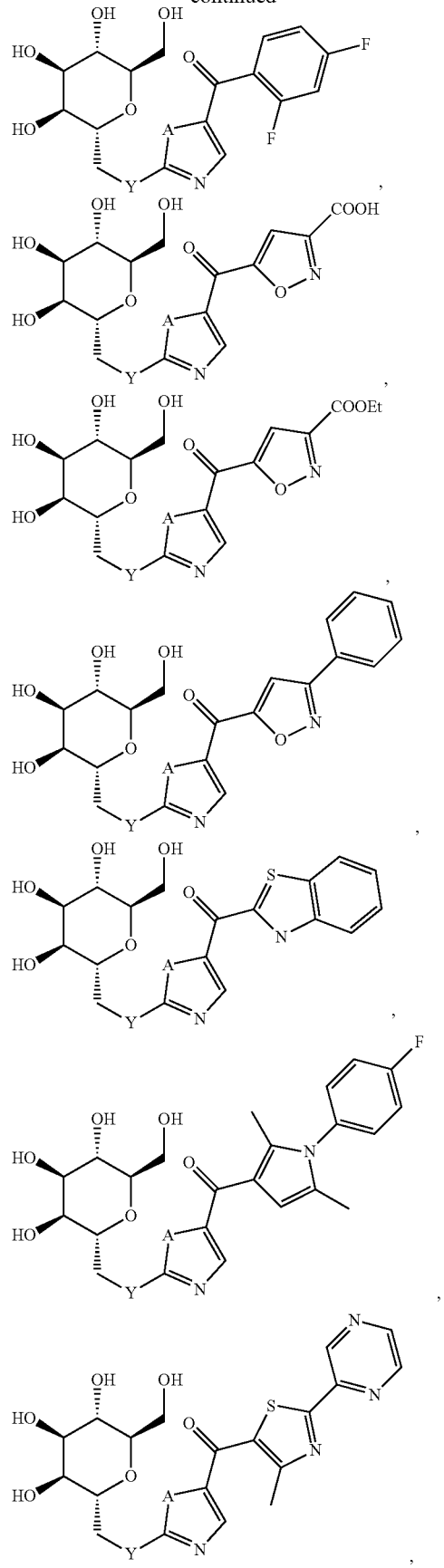
with R' as defined above or below.
In a particular embodiment, the compound of formula (I) is a monovalent compound (i.e. a compound containing only one carbohydrate moiety, mannose), and is in particular selected from:
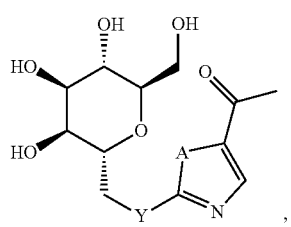

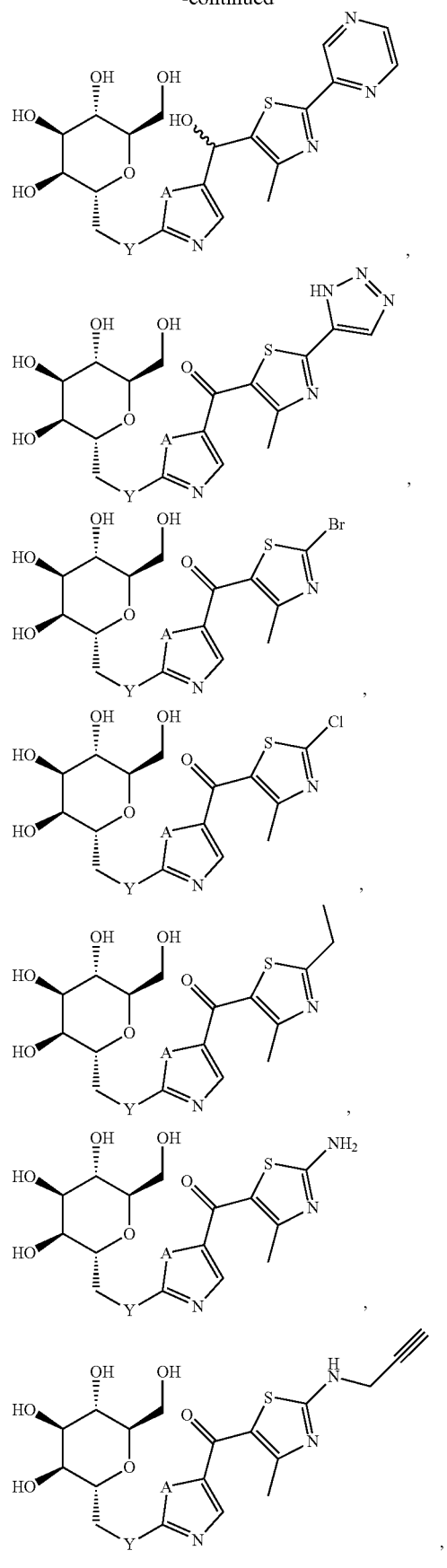
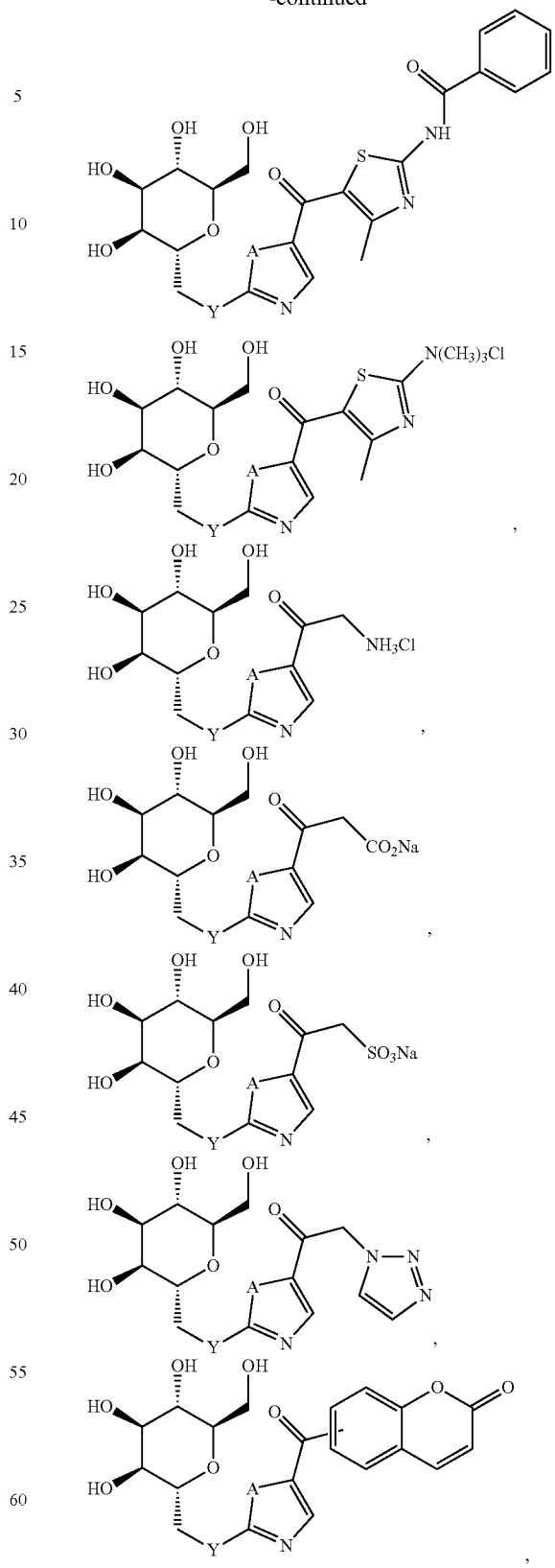
wherein A is as defined above and preferably represents S, and wherein Y is as defined above and preferably represents a single bond or NH.

In a particular embodiment, the compound of formula (I) is a monovalent compound (i.e. a compound containing only one carbohydrate moiety, mannose), and is in particular selected from:
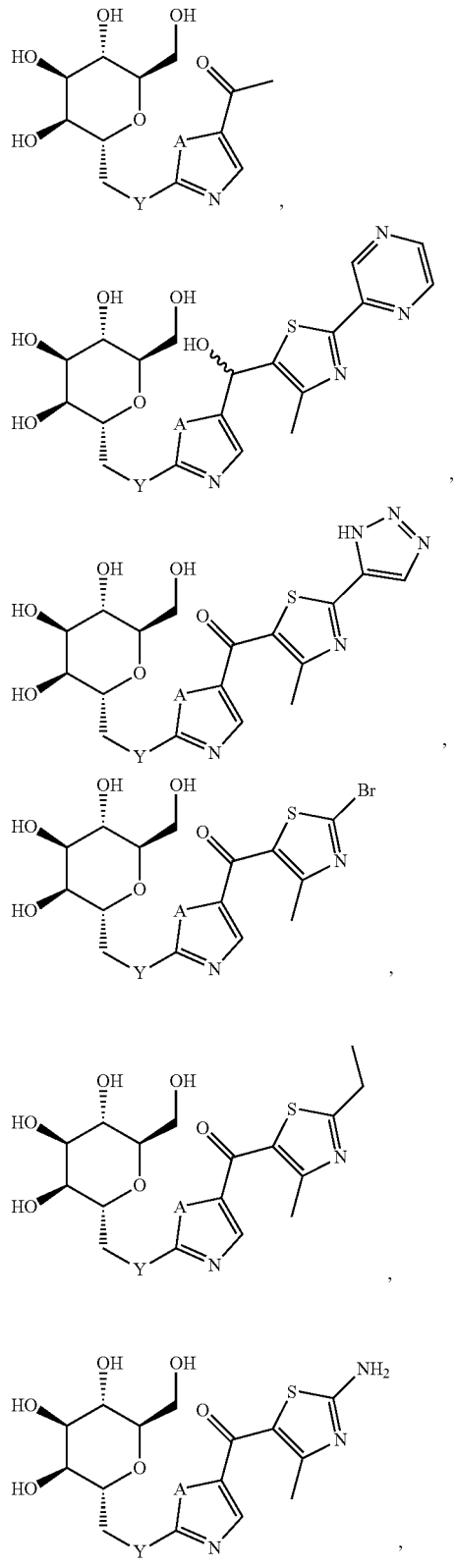
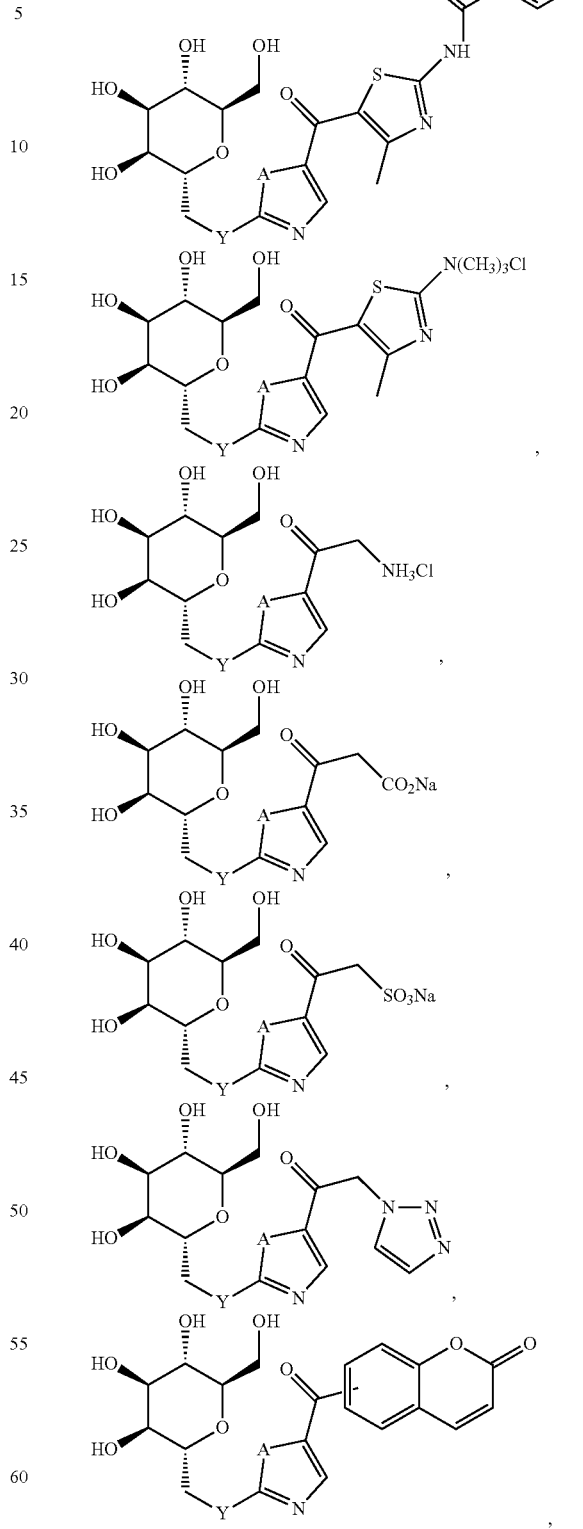
wherein A is as defined above and preferably represents S, and wherein Y is as defined above and preferably represents a single bond or NH.

Preferably, the monovalent compounds of formula (I) are selected from:
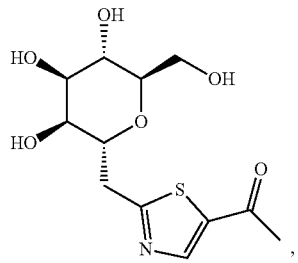,
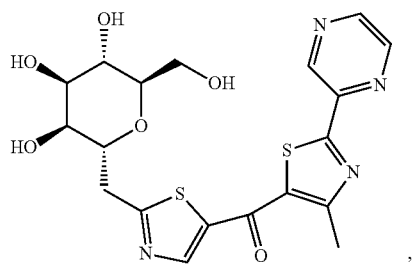,
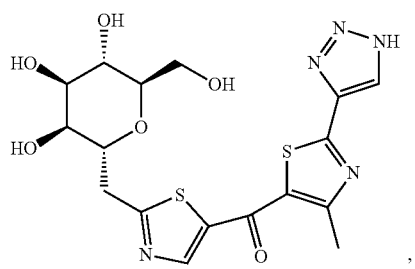,
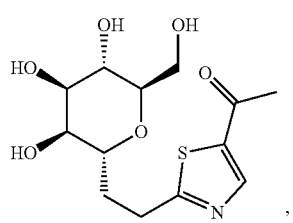,
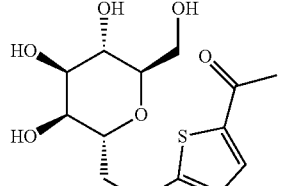,
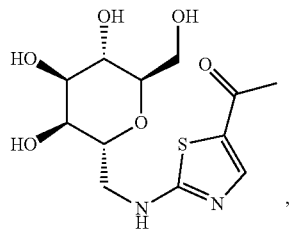,
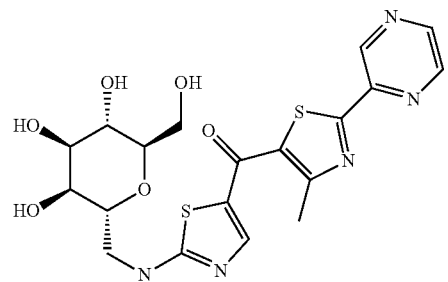,
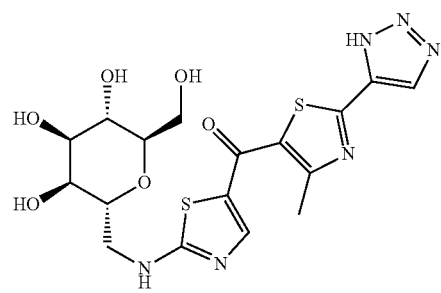,
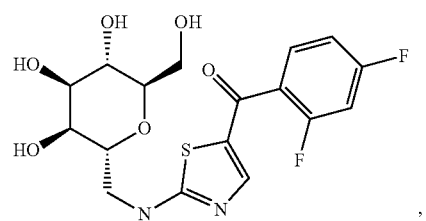,
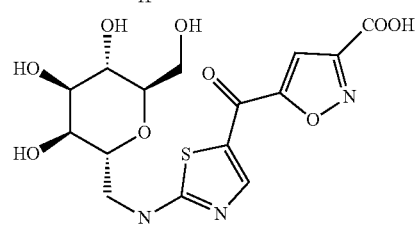,
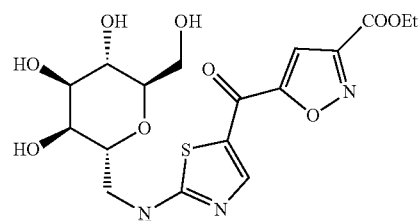,
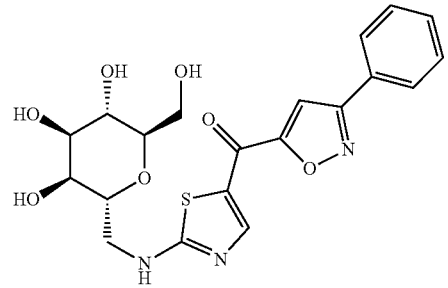,

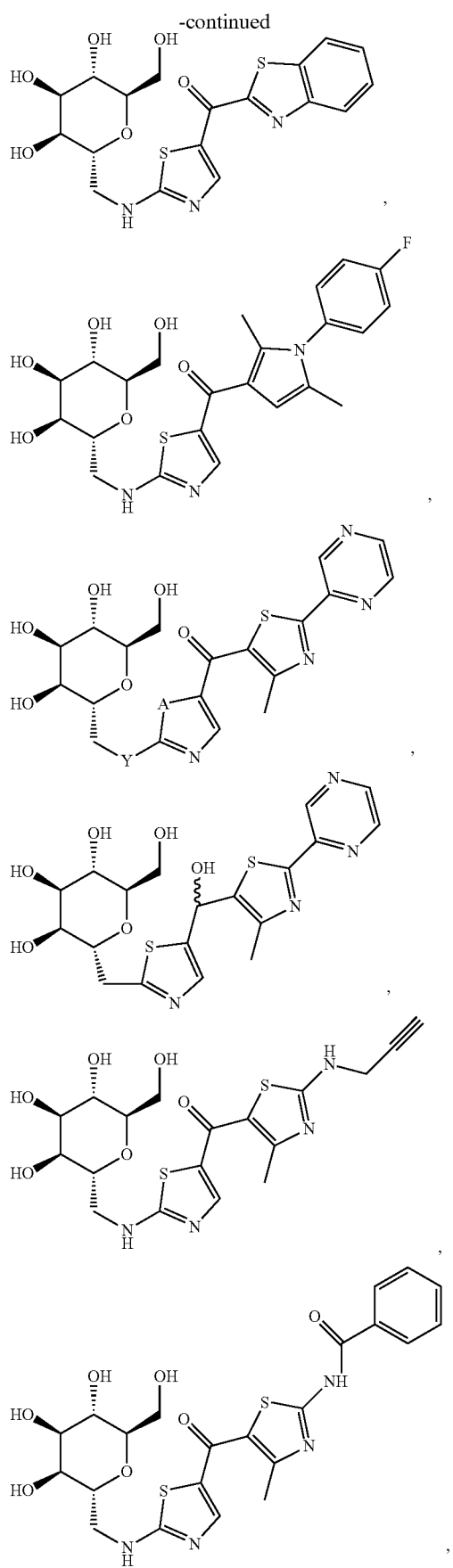
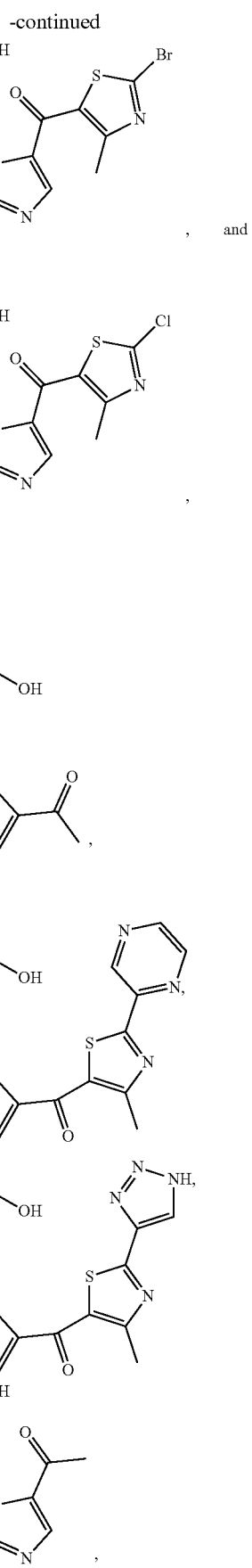
, and
more preferably from

-continued

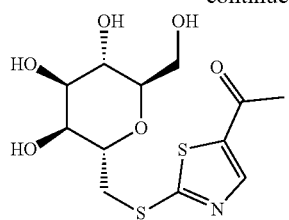

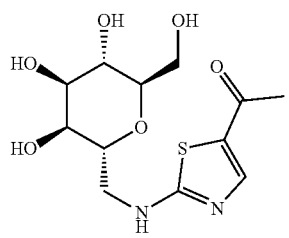

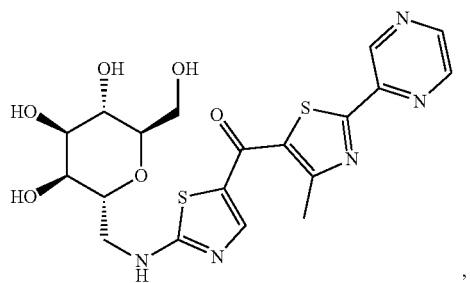

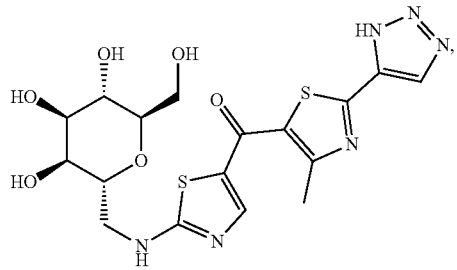

even more preferably it is

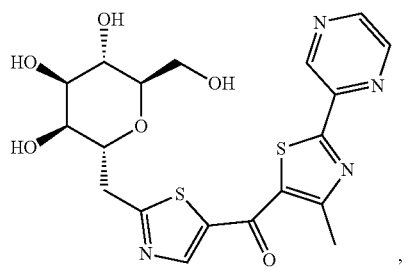 [SMILES: Cc1nc(-c2cnccn2)sc1C(=O)c1cnc(C[C@H]2O[C@H](CO)[C@@H](O)[C@H](O)[C@@H]2O)s1]

In another particular embodiment, the compound of formula (I) is a bivalent compound (i.e. compounds containing two carbohydrate moieties, including mannose), and is in particular selected from:

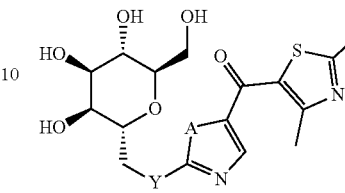

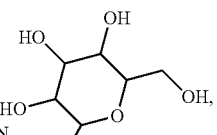

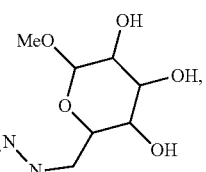

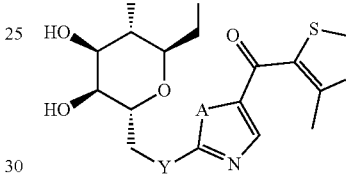

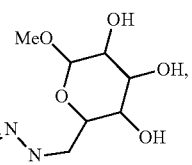

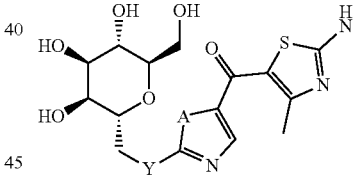

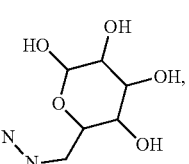

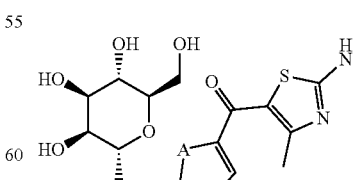

wherein A is as defined above and preferably represents S, and wherein Y is as defined above and preferably represents a single bond or NH.

Even more preferably, the bivalent compound of formula (I) is selected from:
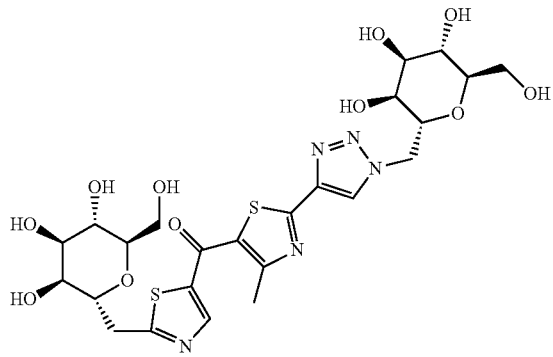
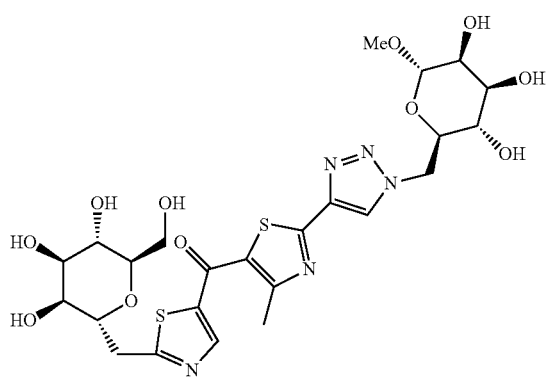
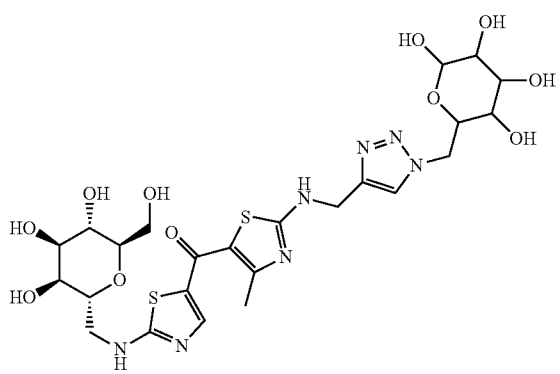
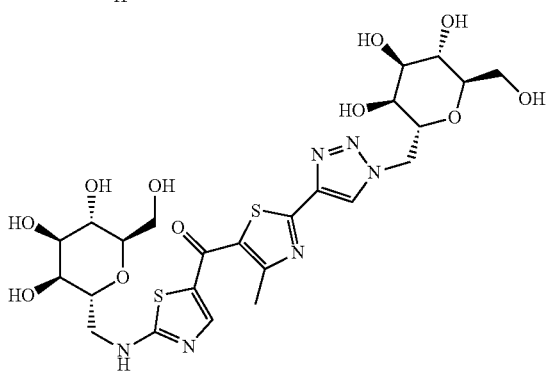
and
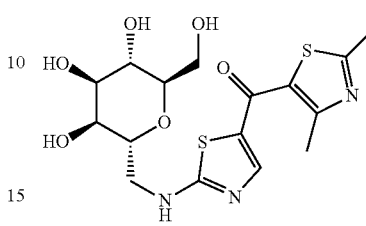
such as
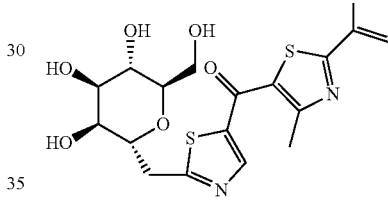
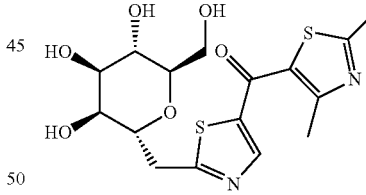
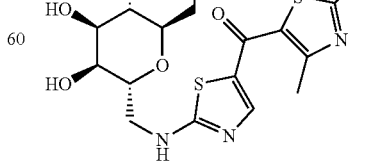
and -continued

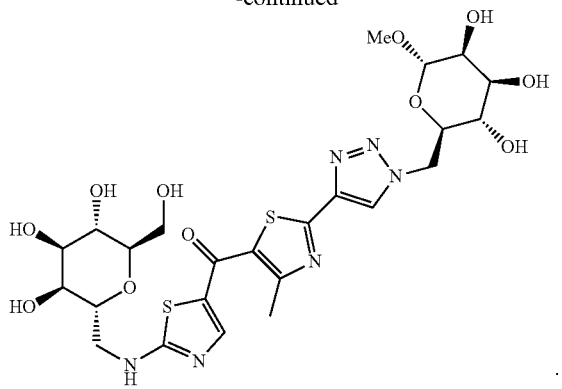

The compounds of formula (I) as described above may exist in tautomeric, diastereomeric or enantiomeric forms. The present invention contemplates all such compounds, including cis- and trans-diastereomers, E- and Z-stereomers, R- and S-enantiomers, diastereomers, d-isomers, l-isomers, the racemic mixtures thereof and other mixtures thereof. Pharmaceutically acceptable salts of such tautomeric, diastereomeric or enantiomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the compounds of the present invention may be in the form of free bases or pharmaceutically acceptable acid addition salts thereof. The term "pharmaceutically acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine- (N-methylglucamine) and procaine. All of these salts may be prepared by conventional means from the corresponding compound by reacting, for example, the appropriate acid or base with any of the compounds of the invention.

Pharmaceutical or Veterinary Compositions

Accordingly, the present invention further relates to a pharmaceutical or veterinary composition comprising a compound of any of formula (I) as described above as active substance, and a pharmaceutically or veterinary acceptable carrier.

Said pharmaceutically or veterinary acceptable carrier is selected, according to the dosage form and mode of administration desired, from the typical excipients known to persons skilled in the art.

The pharmaceutical or veterinary compositions according to the invention can be administered parenterally (such as intravenously or intradermally), topically, orally or rectally.

The term "parenteral" as used herein includes subcutaneous, intravenous, intramuscular, intravesical or infusion techniques. Preferably, the term "parenteral" refers to infusion techniques, in particular in the case of treatment of a UTI (Urinary Tract Infection).

Injectable preparations, for example, sterile injectable aqueous or oleaginous suspensions, may be formulated according to the known art using suitable dispersing or wetting agents and suspending agents.

For therapeutic purposes, formulations for parenteral administration may be in the form of aqueous or non-aqueous isotonic sterile injection solutions or suspensions.

Preferably, the compositions of the invention are administered via oral route.

Solid dosage forms for oral administration may include capsules, tablets, pills, powders, and granules. In such solid dosage forms, the compound is ordinarily combined with one or more adjuvants appropriate to the indicated route of administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

In order to selectively control the release of an inhibitor to a particular region of the gastrointestinal tract, the pharmaceutical compositions of the invention may be manufactured into one or several dosage forms for the controlled, sustained or timed release of one or more of the ingredients, as known in the art.

The amount of the compound of the invention that may be combined with the carrier materials to produce a single dosage of the composition will vary depending upon the subject and the particular mode of administration, as known in the art.

To improve the solubility of the compounds of the invention into aqueous solutions, and in particular into body fluids, said compounds may be formulated as cyclodextrine inclusion complexes, in particular as inclusion complexes with α-, β- or γ-cyclodextrins.

In a particular embodiment, the pharmaceutical or veterinary composition of the invention further comprises another one or more therapeutic compounds.

Another aspect of the present invention encompasses a combination of a compound of formula (I) as described above, with one or more therapeutic compounds.

The therapeutic compound is preferably selected from antibiotics, anticancer agents, steroidal and non-steroidal anti-inflammatory drugs, compounds useful in the treatment of IBD such as Crohn's disease (CD), compounds useful in the treatment of metabolic diseases such as metabolic syndrome, obesity, diabetes (type 1 or 2), hypercholesterolemia, and compounds useful in the treatment of irritable bowel syndrome (IBS). Said compounds are for example Alosetron Amitriptyline, Cholestyramine, Citalopram, Desipramine, Dicyclomine, Diphenoxylate-atropine, Doxepin, Elobixibat, Eluxadoline, Fluoxetine, Hyoscyamine, Imipramine, Ispaghula, Linaclotide Loperamide Lubiprostone Mesalamine/Mesalazine, PEG 3350+E, Paroxetine, Plecanatide, Prucalopride, *Psyllium*, or Rifaximin.

In some embodiments, the combination comprises 1, 2, 3, 4, or 5 therapeutic compounds, preferably one therapeutic compound.

The present invention also relates to a kit comprising:
a first composition comprising at least one compound of formula (I) as described above; and
at least one therapeutic compound, advantageously selected from antibiotics, anticancer agents, steroidal and non-steroidal anti-inflammatory drugs, compounds useful in the treatment of IBD such as CD, compounds useful in the treatment of metabolic diseases such as metabolic syndrome, obesity, diabetes (type 1 or 2), hypercholesterolemia, and compounds useful in the treatment of IBS, as a combination product for simultaneous, separate and staggered use.

The therapeutic compound is preferably an antibiotic when the kit is for use for treating UTIs. It is preferably useful in the treatment of IBD when the kit is for use for treating IBD.

The therapeutic compound is preferably a steroidal or non-steroidal anti-inflammatory drug when the kit is for use for treating an autoimmune inflammatory disease. It is preferably an anti-cancer agent when the kit is for use for treating colorectal cancer, in particular colon cancer.

In any case, the antibiotics, anticancer agents, steroidal and non-steroidal anti-inflammatory drugs, compounds useful in the treatment of IBD such as Crohn's disease (CD), compounds useful in the treatment of metabolic diseases such as metabolic syndrome, obesity, diabetes (type 1 or 2), hypercholesterolemia, and compounds useful in the treatment of IBS, used in the kit of the invention are preferably selected from the lists described above.

The therapeutic compound useful in the treatment of IBD is preferably selected in the group consisting of: azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), and Anti IL12/IL23 (Ustekinumab, ABT874).

The antibiotic is preferably selected from the group consisting of beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides.

The non-steroidal anti-inflammatory drug is preferably selected from the group consisting of salicylate and salts thereof, Celecoxib, Diclofenac and salts thereof, Diflunisal, Etodolac, Fenoprofen, Flurbiprofen, Ibuprofen, Indomethacin, Ketoprofen, Meclofenamate, Mefenamic acid, Meloxicam, Nabumetone, Naproxen, Oxaprozin, Piroxicam, Rofecoxib Salsalate, Sulindac, Tolmetin, and Valdecoxib.

The steroidal anti-inflammatory drug is preferably selected from the group consisting of Prednisone, Methylprednisolone, Prednisolone, aldosterone, cortisol, cortisone, hydrocortisone, corticosterone, tixocortol, ciclesonide, prednicarbate Triamcinolone acetonide, triamcinolone alcohol, mometasone, amcinonide, budesonide, desonide, fluocinonide, fluocinolone acetonide, halcinonide, Hydrocortisone-17-valerate, halometasone, alclometasone, betamethasone, prednicarbate, clobetasone-17-butyrate, clobetasol-17-propionate, fluocortolone, fluocortolone, fluprednidene acetate. dexamethasone, and mixtures thereof, and the corresponding salts or hydrates thereof.

The anti-cancer agent is in particular useful in treating colorectal cancer, in particular colon cancer. Examples of such anti-cancer agents include 5-fluorouracyl, leucovorin, Capecitabin, Irinotecan, and Oxaliplatin.

The compound useful in the treatment of metabolic diseases such as metabolic syndrome, obesity, diabetes (type 1 or 2), hypercholesterolemia is for instance. It can be for example chosen from among: Biguanides, Sulfonylureas, Meglitinide derivatives, Alpha-glucosidase inhibitors, Thiazolidinediones, Glucagonlike peptide-1 agonists, Dipeptidyl peptidase IV Inhibitors, Selective sodium-glucose transporter-2 inhibitors, Insulins, Amylinomimetics, Bile acid sequestrants, Dopamine agonists, orlistat, lorcaserin, phentermine, or topiramat.

Therapeutic Use

The present invention further relates to a compound or a composition or a kit of the invention for use as medicament.

Advantageously, the compound or the composition of the invention is for use for preventing or treating pathologies caused by Adherent *Escherichia coli* and mediated by interactions between Adherent *Escherichia coli* lectins, such as FimH adhesin and host cell surface glycans.

The invention further relates to the use of the compound or composition or a kit of the invention for manufacturing a medicament for preventing or treating pathologies caused by Adherent *Escherichia coli* and mediated by interactions between *Escherichia coli* lectins, such as FimH adhesin and host cell surface glycans.

The present invention further relates to a method of preventing or treating pathologies caused by Adherent *Escherichia coli* and mediated by interactions between Adherent *Escherichia coli* lectins, such as FimH adhesin and host cell surface glycans, comprising administering to a patient in need thereof an effective dose of the compound or the composition or the kit of the invention.

In particular, said pathologies are:
an inflammatory bowel disease, in particular Crohn's disease;
a urinary tract infection, in particular painful bladder syndrome and cystitis, more particularly interstitial cystitis;
an irritable bowel syndrome;
a metabolic disease such as metabolic syndrome, obesity, diabetes (in particular type 2 diabetes), hypercholesterolemia;
autoimmune inflammatory diseases including Berger's disease, Graves' disease, Hashimoto's thyroiditis, the primary myxedema, celiac disease, ulcerative colitis, Crohn's disease, rheumatoid arthritis, primary biliary cirrhosis, primary sclerosing cholangitis, the autoimmune hemolytic anemia, pernicious anemia (pernicious anemia), lupus erythematosus, CREST syndrome, type 1 diabetes, scleroderma, pemphigus vulgaris, pemphigoid oily, the epidermolysis Bullosa acquired, dermatitis herpetiformis, myasthenia, Lambert-Eaton myasthenic syndrome, polymyositis, Sjögren's syndrome, multiple sclerosis, rheumatoid arthritis, Grave's disease and psoriasis; and colorectal cancer, in particular colon cancer.

The "effective dose" of a compound of the invention varies as a function of numerous parameters such as, for example, the route of administration and the weight, the age, the sex, the advancement of the pathology to be treated and the sensitivity of the subject or patient to be treated.

As used herein, "patient" or "subject" includes any mammal, and is preferably a human being in pharmaceutical applications. For veterinary applications, the "patient" or "subject" is preferably a domestic mammal (such as a dog or a cat), or cattle such as a pig (or swine). More preferably, for veterinary applications, the "patient" or "subject" is a cat or a dog.

Preferably, in case the patient is a human being, in particular for patients living with diabetes or another disease involving increased apoptosis rate, said pathologies are:
  an inflammatory bowel disease, in particular Ulcerative colitis or Crohn's disease,
  an irritable bowel syndrome,
  a urinary tract infection, in particular painful bladder syndrome and cystitis, more particularly interstitial cystitis,
  celiac disease, and
  colorectal cancer, in particular colon cancer.

When the pathology is an IBD, and in particular CD, the patient may not have clinical symptoms of IBD (or CD). In such embodiments, the subject may have a quiescent IBD (such as CD). In other embodiments, a subject may have clinical symptoms of an IBD (such as CD), such as Diarrhea, Fever and fatigue, Abdominal pain and cramping, Blood in stool, Reduced appetite, Unintended weight loss.

In the veterinary field, the medicament is a veterinary medicament, in particular for preventing or treating Crohn's disease or colitis such as granulomatous or ulcerative colitis in mammals, such as dogs, cats or pigs, preferably dogs or cats.

Methods for Preparing the Compounds of Formula (I)
Compounds of Formula (I) Wherein Y is a Single Bond Compounds of formula (I) as defined above wherein Y represents a single bond may be prepared following a method comprising the steps of (see scheme 1 below):
  a) converting mannose into an all O-protected allylmannose of formula (II), wherein PG represents an O-protecting group, in particular benzyl or acetyl;
  b) subjecting the allylmannose of formula (II) to an ozonolysis reaction in the presence of a methoxide source such as methanol or sodium methoxide, so as to furnish the corresponding methyl mannose acetate of formula (III);
  c) converting the methyl carboxylate of the methyl mannose acetate of formula (III) into an amidine (A=NH), amide (A=O) or a thioamide (A=S) intermediate of formula (IV);
  d) cyclizing the intermediate of formula (IV) in the presence of a N,N-dimethylalcanamide di($C_1$-$C_6$)-alkyl acetal of formula (V) and an α-halogenoketone of formula (VI) to yield a heterocyclic mannose derivative of formula (VII) wherein A, R and $R_2$ are as defined above;
  e) optionally deprotecting the heterocyclic mannose derivative of formula (VII) so as to obtain a compound of formula (I) wherein $R_1$ represents H, Y is a single bond and A, R and $R_2$ are as defined above.

For obtaining compounds of formula (I) wherein Y is a single bond and $R_1$ represents CO—($C_1$-$C_6$)-alkyl, ($C_1$-$C_6$)-alkyl or alkylaryl, either the PG group of the heterocyclic mannose derivative of formula (VII) already corresponds to $R_1$, and in that case step e) is omitted. In case the PG group of the heterocyclic mannose derivative of formula (VII) differs from $R_1$, then step e) is carried out, and the process further comprises a step f) of transforming the OH groups of the mannose residue into $OR_1$ groups.

Scheme 1: Alternative method for preparing the compounds of formula (I).

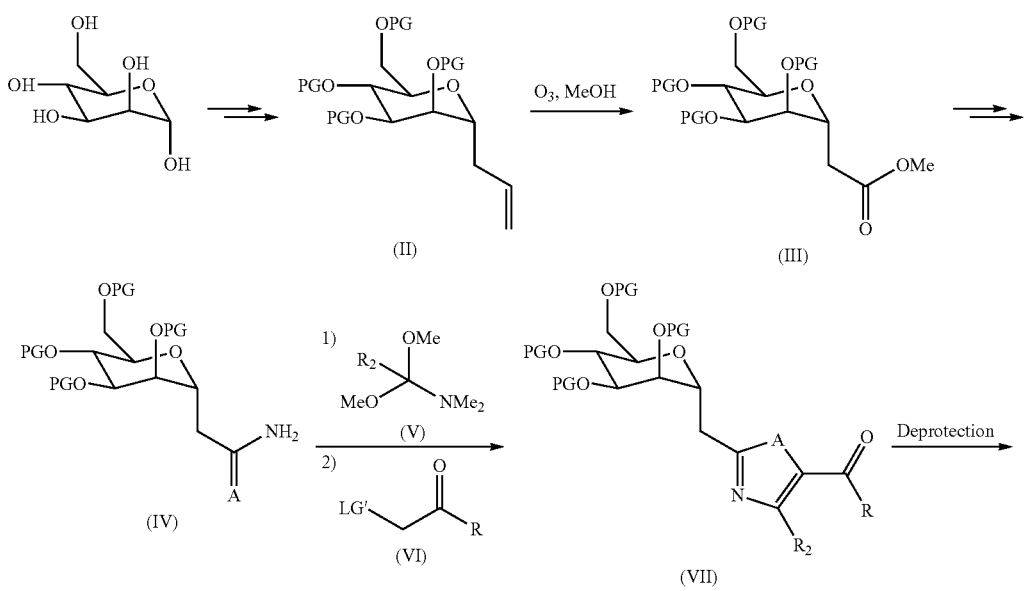

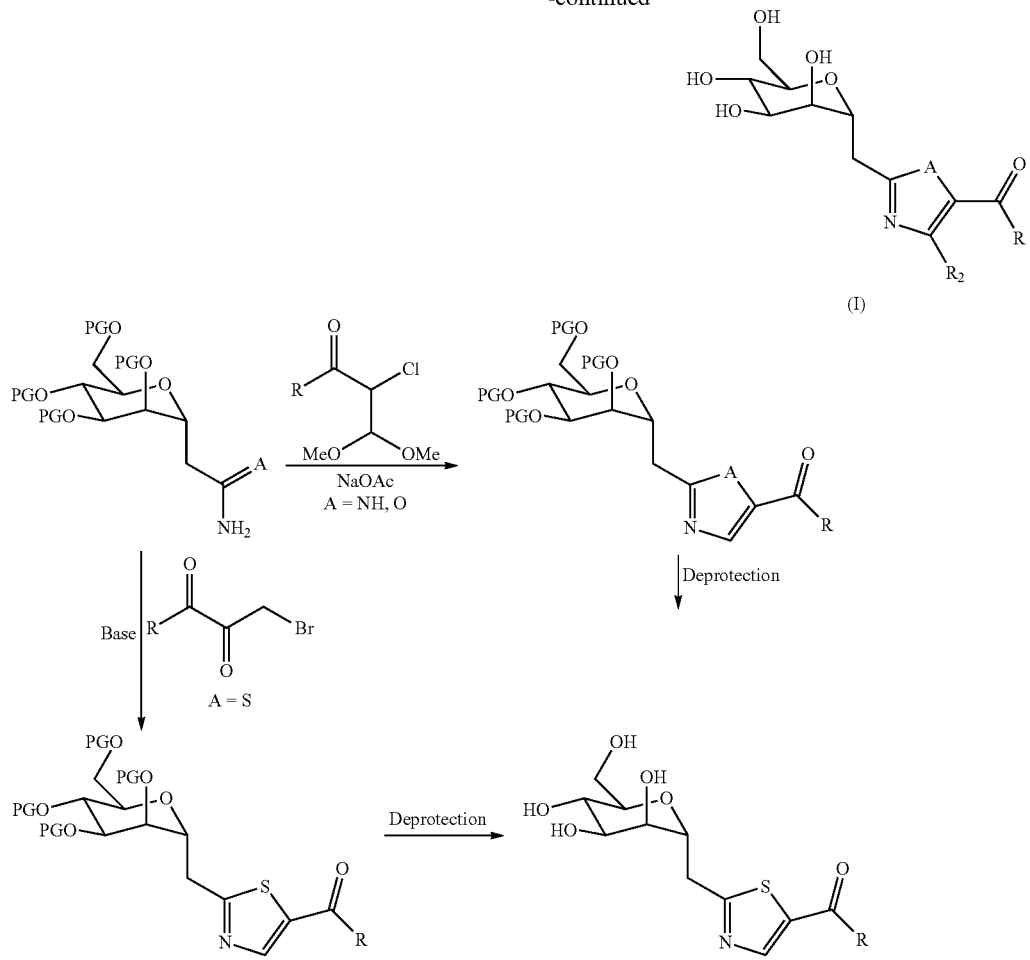

Step a) is carried out using conventional reactions known in the art, in particular using the following reaction sequence: protecting the free hydroxyl groups of mannose, followed by generating of the corresponding oxonium ion in the presence of a Lewis acid, such as trimethylsilyltriflate, and reacting said oxonium with allyltrialkylsilane, in particular allyltrimethylsilane.

Ozonolysis step b) in the presence of methanol is carried out under conventional conditions known to the one of skill in the art. For instance, the ozonolysis step b) is carried out in dichloromethane, mixed with methanol or sodium methoxide, at low temperature such as a temperature of between −78° C. and −10° C. Ozone is the bubbled in the reaction mixture at said low temperature until the reaction mixture turns blue. The reaction is then quenched for example by addition of dimethylsulfide.

Step c) is carried out using reactions known in the art. For instance, the amide of formula (IV) (in this case, A represents O) is obtained by hydrolyzing the methyl acetate of formula (III) to the corresponding carboxylic acid in the presence of a hydroxide salt (such as sodium or preferably lithium hydroxide), followed by activation of the obtained carboxylic acid, for instance by reaction with an acyl chloride (such as oxalyl chloride or acetyl chloride), and subsequent reaction with aqueous ammonia. The thioamide of formula (IV) (in this case, A represents S) is for instance obtained by reacting the amide of formula (IV) (i.e. wherein A represents O) with a sulfuring agent such as phosphorous pentasulfide.

Cyclization step d) may be carried out following the procedures described in Brument et al. 2013. In particular, step d) is carried out by reacting intermediate (IV) with a N,N-Dimethylalcanamide di($C_1$-$C_6$)-alkyl acetal (such as N,N-dimethylformamide dimethyl acetal or N,N-dimethylacetamide dimethyl acetal) in an aprotic polar solvent such as acetonitrile, at a temperature of between 40° C. and the boiling point of the solvent, preferably 60° C. An α-halogenoketone of formula (VI) is then added and the reaction mixture is further heated in the presence of a base such as a tertiary amine (preferably trimethylamine, diisopropylethylamine or hexamethyldisilazane) and of an α-halogenoketone of formula (VI), optionally activated by addition of sodium iodide, to yield a heterocyclic mannose derivative of formula (VII).

Conventional reaction conditions known in the art, such as described for instance in Greene's "Protective Groups In Organic synthesis", are used for deprotection step e).

When carried out, step f) is conducted according to conventional reactions known in the art, such as described in Greene's "Protective Groups In Organic synthesis".

Compounds of Formula (I) Wherein Y is —O—, —$NR_3$— or —S—: Route 1

Compounds of formula (I) as defined above wherein Y represents O, $NR_3$ or S, may be prepared following a method comprising the steps of (see scheme 2 below):

a) reacting an intermediate of formula (VIII) wherein PG represents an O-protecting group and LG represents a leaving group, with an heterocyclic intermediate of formula (IX) wherein Y represents O, $NR_3$ or S and A and R are as defined above, so as to obtain a heterocyclic mannose derivative of formula (X) wherein Y represents O, $NR_3$ or S and A and R are as defined above, comprising the nucleophilic substitution of the leaving group LG of the intermediate of formula (VIII) by the YH substituent of the heterocyclic intermediate of formula (IX);

b) optionally deprotecting the heterocyclic mannose derivative of formula (XIII) so as to obtain a compound of formula (I) wherein Y represents O, $NR_3$ or S, A and R are as defined above and $R_1$ represents H.

For obtaining compounds of formula (I) wherein Y represents O, $NR_3$ or S and $R_1$ represents CO—$(C_1-C_6)$-alkyl, $(C_1-C_6)$-alkyl or alkylaryl, and A and R are as defined above, either the PG group of the heterocyclic mannose derivative of formula (XII) already corresponds to $R_1$, and in that case step e) is omitted. In case the PG group of the heterocyclic mannose derivative of formula (XII) differs from $R_1$, then step b) is carried out, and the process further comprises a step c) of transforming the OH groups of the mannose residue into $OR_1$ groups.

Scheme 2: Method 1 for preparing the compounds of formula (I) as defined above wherein Y represents O, $NR_3$ and S.

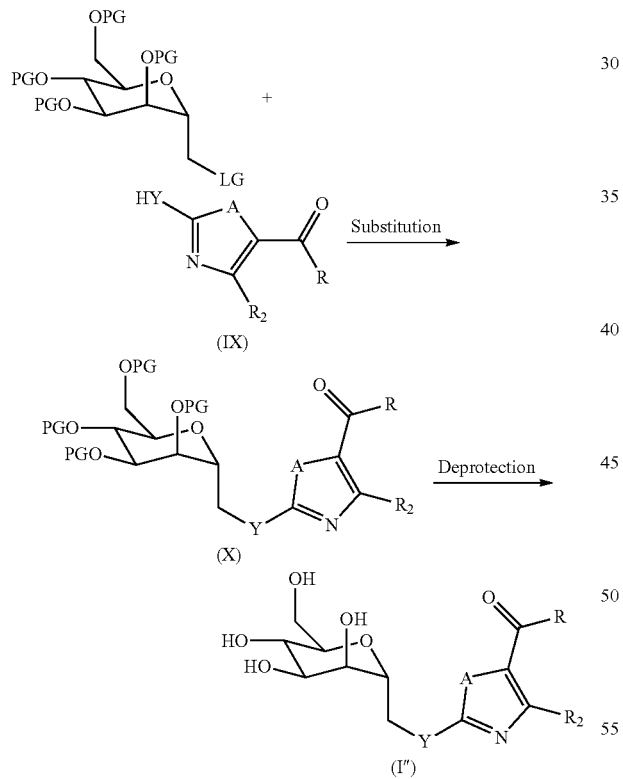

Step a) is typically carried out in the presence of a base, in particular an inorganic base such as a carbonate salt, preferably potassium carbonate. The substitution step a) is preferably carried out in a polar solvent, such as DMF (dimethylformamide), advantageously at a temperature of between 60° C. and 120° C.

Conventional reaction conditions known in the art, such as described for instance in Greene's "Protective Groups In Organic synthesis", are used for deprotection step b).

When carried out, step c) is conducted according to conventional reactions known in the art, such as described in Greene's "Protective Groups In Organic synthesis".

The intermediate of formula (VIII) (with PG representing an O-protecting group and LG representing a leaving group), may be prepared following a method comprising the steps of (see scheme 3 below):

a) converting mannose into an all O-protected allyl-C-mannosyl of formula (II), wherein PG represents an O-protecting group, in particular benzyl or acetyl;

b) Isomerizing the double bond of the allyl substituent of the allyl-C-mannosyl of formula (II), so as to obtain the vinyl mannose of formula (XI);

c) subjecting the vinyl-C-mannosyl of formula (XI) to a reductive ozonolysis reaction, so as to furnish the corresponding alcohol of formula (XII);

c) converting the alcohol of formula (XII) into the intermediate of formula (VIII).

Scheme 3: Method for preparing the intermediate of formula (VIII) with PG representing an O-protecting group and LG representing a leaving group

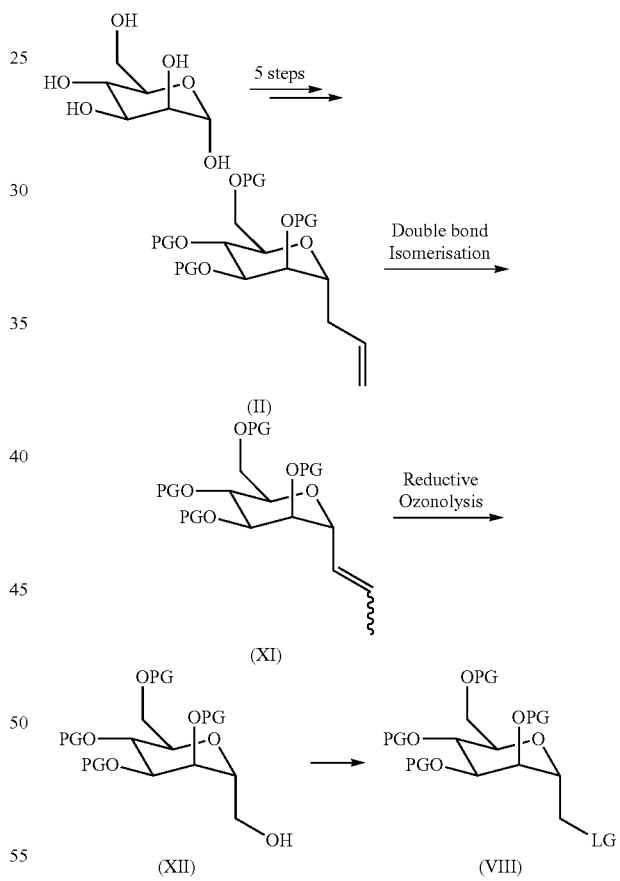

Step a) is carried out using conventional reactions known in the art, in particular using the following reaction sequence: protecting the free hydroxyl groups of mannose, followed by generating of the corresponding oxonium ion in the presence of a Lewis acid, such as trimethylsilyltriflate, and reacting said oxonium with allyltrialkylsilane, in particular allyltrimethylsilane.

Isomerization step b) is carried out under conventional conditions, such as in the presence of a palladium catalyst under an inter atmosphere The palladium catalyst is typically bis(benzonitrile)palladium (II) chloride. The solvent used in isomerization step b) is preferably an apolar aprotic solvent, in particular an apolar aprotic aromatic solvent, such as toluene or benzene.

Reductive ozonolysis step c) is carried out under conventional conditions known to the one of skill in the art. For instance, the reductive ozonolysis step c) is carried out in methanol or a mixture of dichloromethane and methanol, at low temperature such as a temperature of between −78° C. and room temperature (25° C.). Ozone is the bubbled in the reaction mixture at said low temperature until the reaction mixture turns blue. The reaction is then quenched by addition of sodium borohydride (NaBH$_4$).

The resulting alcohol function of the alcohol of formula (XII) is then converted into a leaving such as a sulfonate (preferably mesylate or tosylate) or into a halogen such as bromide, as known in the art.

The heterocyclic derivative of formula (IX) wherein Y represents O, NR$_3$ or S and A and R are as defined above and R$_2$ represents a linear or branched (C$_1$-C$_6$)-alkyl or CF$_3$, may be prepared using a method comprising the steps of (see scheme 4 below):

a) condensing urea derivative of formula (XIII) wherein A is O, S or NH, with a N,N-dimethylalcanamide di(C$_1$-C$_6$)-alkyl acetal of formula (V) wherein R$_2$ represents a linear or branched (C$_1$-C$_6$)-alkyl or CF$_3$, to obtain an intermediate of formula (XIV);

b) cyclizing the intermediate of formula (XIV) as described above, with an α-halogenoketone of formula (VI) wherein R is as described above and LG' represents a leaving group, preferably a halogen such as bromine, to yield a heterocyclic derivative of formula (IX)$_N$ with R and R$_2$ as defined above (and Y representing NH);

c) optionally converting heterocyclic derivative of formula (IX)$_N$ into a haloheterocyclic derivative of formula (XV) with R and R$_2$ as defined above and Hal representing a halogen atom, preferably chlorine or bromine;

d) subsequently converting said derivative of formula (XV) into a heterocyclic derivative of formula (IX)$_{O,S}$ with R and R$_2$ as defined above (and Y representing respectively O or S).

Scheme 4: Method for preparing the intermediate of formula (IX) wherein Y represents O, NR$_3$ or S, and A, R and are as defined above and R$_2$ represents a linear or branced (C$_1$-C$_6$)-alkyl or CF$_3$

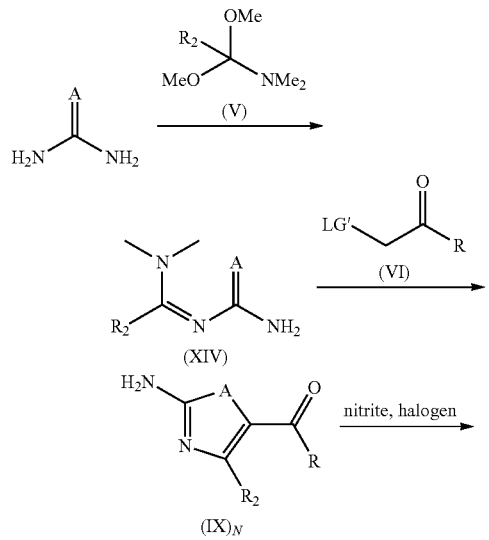

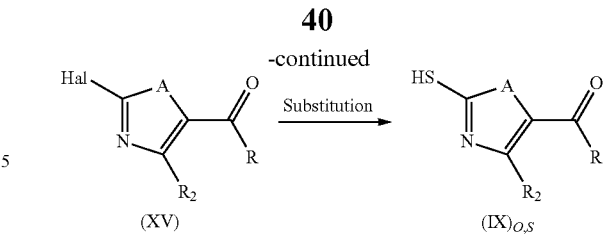

Step a) is known in the art, and is typically carried out by mixing the urea derivative of formula (XIII) and N,N-dimethylalcanamide di(C$_1$-C$_6$)-alkyl acetal of formula (V) in an aprotic apolar solvent such as dichloromethane (DCM), in particular at a temperature of between 20° C. and 40° C.

Cyclization step b) is typically carried out by reacting the intermediate of formula (XIV) with an α-halogenoketone of formula (VI) (optionally activated by addition of sodium iodide) in an aprotic polar solvent such as acetonitrile, at a temperature of between 40° C. and the boiling point of the solvent, preferably 60° C., in the presence of a base such as a tertiary amine (preferably trimethylamine, diisopropylethylamine or hexamethyldisilazane) to yield a heterocyclic mannose derivative of formula (IX)$_N$ with R and R$_2$ as defined above (and Y representing NH).

Step c) is also conventional in the art. In step c), the halogen is preferably chlorine or bromine. The first substep of step c) may consist of reacting the heterocyclic mannose derivative of formula (IX)$_N$ with isoamyl nitrite and Copper (II) Bromide (CuBr$_2$) in an aprotic polar solvent such as acetonitrile, preferably under reflux, thus leading to the corresponding bromo derivative. Alternatively, step c) may consist in reacting the heterocyclic mannose derivative of formula (IX)$_N$ with sodium nitrite in concentrated aqueous hydrochloride in the presence of copper (II) sulfate and sodium chloride, thus leading to the chloro derivative.

In step d), the halogeno derivative of formula (XV) is then reacted for instance with a thioacetate salt such as potassium thioacetate, preferably in methanol, thus leading to the compound of formula (IX)$_S$. Alternatively, the halogeno derivative of formula (XV) may be reacted with a hydroxide salt to yield the corresponding derivative of formula (IX)$_O$.

The heterocyclic derivative of formula (IX) wherein Y represents O, NR$_3$ or S and A and R are as defined above and R$_2$ represents H, may be prepared using a method comprising the steps of (see scheme 5 below):

a) condensing urea derivative of formula (XIII) wherein A is O, S or NH, dimethylacetamide dimethyl acetal, to obtain an intermediate of formula (XVI);

b) cyclizing the intermediate of formula (XVI) as described above, with an α-halogenoketone of formula (VI) wherein R is as described above and LG' represents a leaving group, preferably a halogen atom such as bromine, to yield a heterocyclic derivative of formula (IX')$_N$ with R and R$_2$ as defined above (and Y representing NH);

c) optionally converting heterocyclic derivative of formula (IX')$_N$ into a haloheterocyclic derivative of formula (XV') with R and R$_2$ as defined above and Hal represents a halogen atom, preferably chlorine or bromine;

d) subsequently converting said derivative of formula (XV') into a heterocyclic derivative of formula (IX')$_{O,S}$ with R and R$_2$ as defined above (and Y representing respectively O or S).

Scheme 5: Method for preparing the intermediate of formula (IX) wherein Y represents O, NR$_3$ or S, and A, R and are as defined above and R$_2$ is H

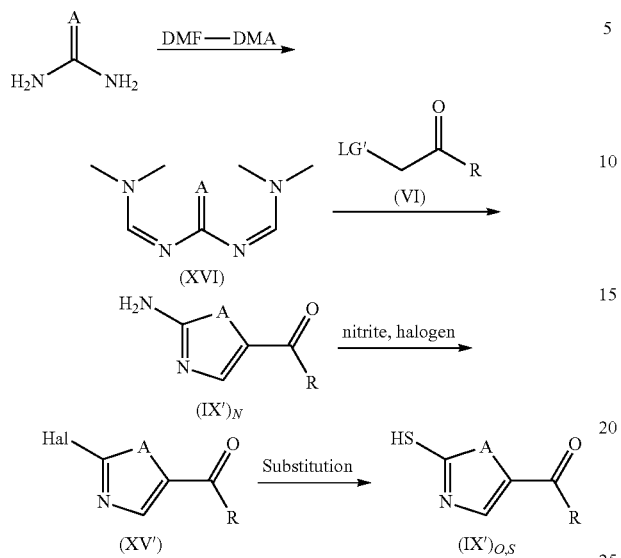

Scheme 6: Method 2 for preparing the compounds of formula (I″) (i.e. a compound of formula (I) as defined above wherein Y represents O, NR$_3$ and S).

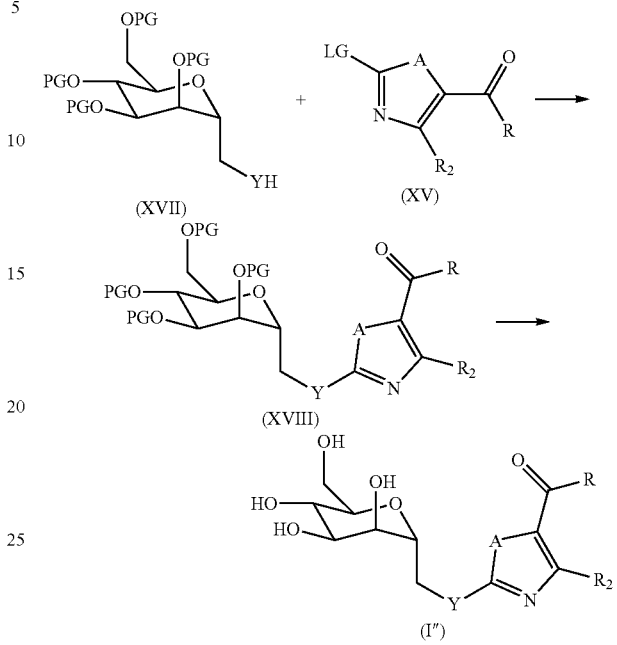

Step a) is known in the art, and is typically carried out by mixing the urea derivative of formula (XIII) and N,N-dimethyl formamide dimethyl acetal in an aprotic apolar solvent such as dichloromethane (DCM), in particular at a temperature of between 20° C. and 40° C.

Steps b), c) and d) may be carried out under conditions similar to those described above in the case where R$_2$ represents a linear or branched (C$_1$-C$_6$)-alkyl or CF$_3$.

Compounds of Formula (I) Wherein Y is —O—, —NR$_3$— or —S—: Route 2

According to a second route, compounds of formula (I) as defined above wherein Y represents O, NR$_3$ or S, may be prepared following a method comprising the steps of (see scheme 6 below):

a) reacting an intermediate of formula (XVII) wherein PG represents an O-protecting group and Y is as described above, with an heterocyclic intermediate of formula (XV) wherein A, R and R$_2$ are as defined above, so as to obtain a heterocyclic mannose derivative of formula (XVII) wherein Y represents O, NR$_3$ or S and A, R and R$_2$ are as defined above, comprising the nucleophilic substitution of the halogen group of the heterocyclic intermediate of formula (XV) by the YH substituent of the intermediate of formula (XVII);

b) optionally deprotecting the heterocyclic mannose derivative of formula (XVIII) so as to obtain a compound of formula (I) wherein Y represents O, NR$_3$ or S, and A, R and R$_2$ are as defined above and R$_1$ represents H.

For obtaining compounds of formula (I) wherein Y represents O, NR$_3$ or S and R$_1$ represents CO—(C$_1$-C$_6$)-alkyl, (C$_1$-C$_6$)-alkyl or alkylaryl, and A, R and R$_2$ are as defined above, either the PG group of the heterocyclic mannose derivative of formula (XVIII) already corresponds to R$_1$, and in that case step e) is omitted. In case the PG group of the heterocyclic mannose derivative of formula (XVIII) differs from R$_1$, then step b) is carried out, and the process further comprises a step c) of transforming the OH groups of the mannose residue into OR$_1$ groups.

Step a) is typically carried out in the presence of a base, in particular an inorganic base such as a carbonate salt, preferably potassium carbonate. The substitution step a) is preferably carried out in a polar solvent, such as DMF (dimethylformamide), advantageously at a temperature of between 60° C. and 120° C.

Conventional reaction conditions known in the art, such as described for instance in Greene's "Protective Groups In Organic synthesis", are used for deprotection step b).

When carried out, step c) is conducted according to conventional reactions known in the art, such as described in Greene's "Protective Groups In Organic synthesis".

A typical synthesis of intermediate (XVII) wherein Y represents O has been presented above (see the synthesis of alcohol XII).

When Y represents S, a typical synthesis consists in reacting intermediate (VIII) with a thioacetate salt in the presence of a base.

A typical method for preparing the intermediate (XVII) wherein Y represents NR$_3$ comprises reacting intermediate (VIII) with a nucleophilic azide source such as sodium azide, typically in a polar solvent such as DMF preferably at a temperature of between 80° C. and 120° C., to obtain the corresponding azide derivative, and subsequently reducing said azide derivative typically using triphenylphosphine preferably in a polar aprotic solvent such as an ether, in particular tetrahydrofuran (see scheme 7 below). Optionally, the method may further comprise a reductive amination step or an acylation step.

Compounds of Formula (I) Wherein Y is —O—, —NR$_3$— or —S—: Route 3

According to a third route, compounds of formula (I) as defined above wherein Y represents O, NR$_3$ or S, may be prepared following a method comprising the steps of (see scheme 7 below):

a) forming the intermediate of formula (XIX) by reacting intermediate (XVII) wherein PG represents a O-protecting group and Y represents O, NR$_3$ or S, with an alcaline salt (preferably a sodium or potassium salt) of a compound of formula $^-$NCA wherein A is O, NH or S;

b) cyclizing the intermediate of formula (XIX) in the presence of a N,N-dimethylalcanamide di(C$_1$-C$_6$)-alkyl acetal of formula (V) and an α-halogenoketone of formula (VI) to yield a heterocyclic mannose derivative of formula (XVIII) wherein A, R and R$_2$ are as defined above, and LG' is a leaving group, preferably a halogen atom such as bromine or chlorine;

c) optionally deprotecting the heterocyclic mannose derivative of formula (XVIII) so as to obtain a compound of formula (I) wherein Y represents O, NR$_3$ or S, and A, R and R$_2$ are as defined above and R$_1$ represents H.

For obtaining compounds of formula (I) wherein Y represents O, NR$_3$ or S and R$_1$ represents CO—(C$_1$-C$_6$)-alkyl, (C$_1$-C$_6$)-alkyl or alkylaryl, and A, R and R$_2$ are as defined above, either the PG group of the heterocyclic mannose derivative of formula (XVIII) already corresponds to R$_1$, and in that case step c) is omitted. In case the PG group of the heterocyclic mannose derivative of formula (XVIII) differs from R$_1$, then step b) is carried out, and the process further comprises a step d) of transforming the OH groups of the mannose residue into OR$_1$ groups.

Scheme 7: Method 3 for preparing the compounds of formula (I″) (compound of formula (I) as defined above wherein Y represents O, NR$_3$ and S). R″ represents an acyl chloride or a chlorotri-(C$_1$-C$_6$)alkyl-silane such as benzoyl chloride or chlorotrimethylsilane

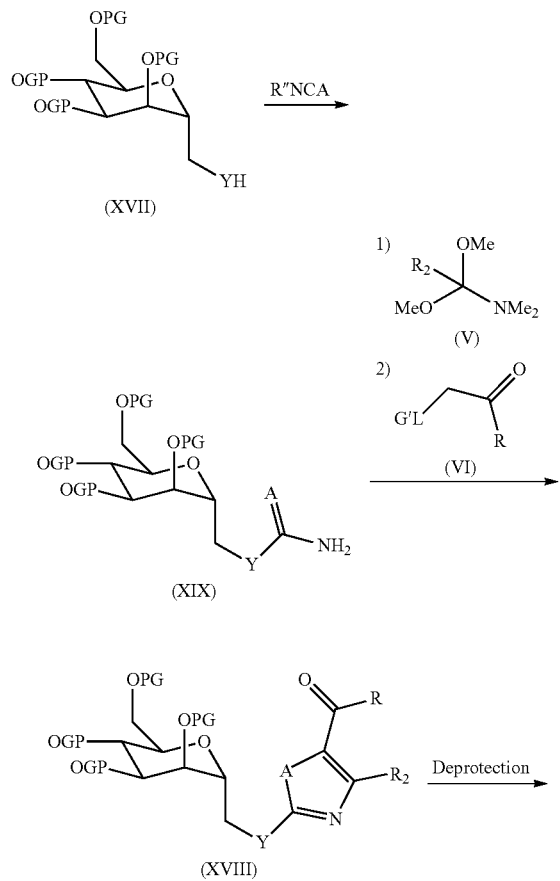

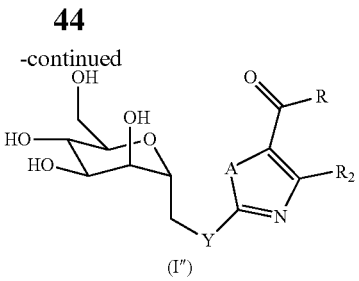

Step a) is typically carried out in the presence of an acyl chloride or a chlorotri-(C$_1$-C$_6$)alkyl-silane such as benzoyl chloride or chlorotrimethylsilane, in a polar aprotic solvent such as acetone, yielding a protected derivative (preferably a benzoyl or a trimethylsilyl derivative) which is then hydrolyzed preferably in methanol in the presence of sodium hydroxide.

Cyclization step b) is typically carried out by reacting intermediate (XIX) with a N,N-Dimethylalcanamide di(C$_1$-C$_6$)-alkyl acetal (such as N,N-dimethylacetamide dimethyl acetal or N,N-dimethylacetamide dimethyl acetal) in an aprotic polar solvent such as acetonitrile, at a temperature of between 40° C. and the boiling point of the solvent, preferably 60° C. An α-halogenoketone of formula (VI) is then added and the reaction mixture is further heated in the presence of a base such as a tertiary amine (preferably trimethylamine, diisopropylethylamine or hexamethyldisilazane) and of an α-halogenoketone of formula (VI), optionally activated by addition of sodium iodide, to yield a heterocyclic mannose derivative of formula (XVIII).

Conventional reaction conditions known in the art, such as described for instance in Greene's "Protective Groups In Organic synthesis", are used for deprotection step c).

When carried out, step d) is conducted according to conventional reactions known in the art, such as described in Greene's "Protective Groups In Organic synthesis".

Compounds of Formula (I) Wherein Y is —CH$_2$—

Compounds of formula (I) as defined above wherein Y represents —CH$_2$— may be prepared following a method comprising the steps of (see scheme 8 below):

a) converting mannose into an all O-protected allylmannose of formula (II), wherein PG represents an O-protecting group, in particular benzyl or acetyl;

b) subjecting the allylmannose of formula (II) to a reductive ozonolysis reaction, so as to furnish the corresponding mannose alcohol of formula (XX);

c) converting the mannose alcohol of formula (XX) into the corresponding intermediate of formula (XXI), wherein LG represents a leaving group;

d) converting said intermediate of formula (XXI) into the corresponding mannose nitril of formula (XXII);

e), forming an intermediate of formula (XXIII), wherein A is O (the compound of formula (XXIII) is then an amide), S (the compound of formula (XXIII) is then a thioamide) or NR3 (the compound of formula (XXIII) is then an amidine);

f) cyclizing the intermediate of formula (XXIII) in the presence of a N,N-dimethylalcanamide di(C$_1$-C$_6$)-alkyl acetal of formula (V) and a α-halogenoketone of formula (VI) to yield a heterocyclic mannose derivative of formula (XXIV) wherein A, R and R$_2$ are as defined above;

g) optionally deprotecting the heterocyclic mannose derivative of formula (VII) so as to obtain a compound of formula (I) wherein R$_1$ represents H, Y is a single bond and A, R and R$_2$ are as defined above.

For obtaining compounds of formula (I) wherein Y is CH$_2$ and R$_1$ represents CO—(C$_1$-C$_6$)-alkyl, (C$_1$-C$_6$)-alkyl or alkylaryl, either the PG group of the heterocyclic mannose derivative of formula (XXIV) already corresponds to $R_1$, and in that case step e) is omitted. In case the PG group of the heterocyclic mannose derivative of formula (XXIV) differs from $R_1$, then step e) is carried out, and the process further comprises a step h) of transforming the OH groups of the mannose residue into $OR_1$ groups.

Scheme 8: Method for preparing the compounds of formula (I''')
(compound of formula (I) as defined above wherein Y represents $(CH_2)$.

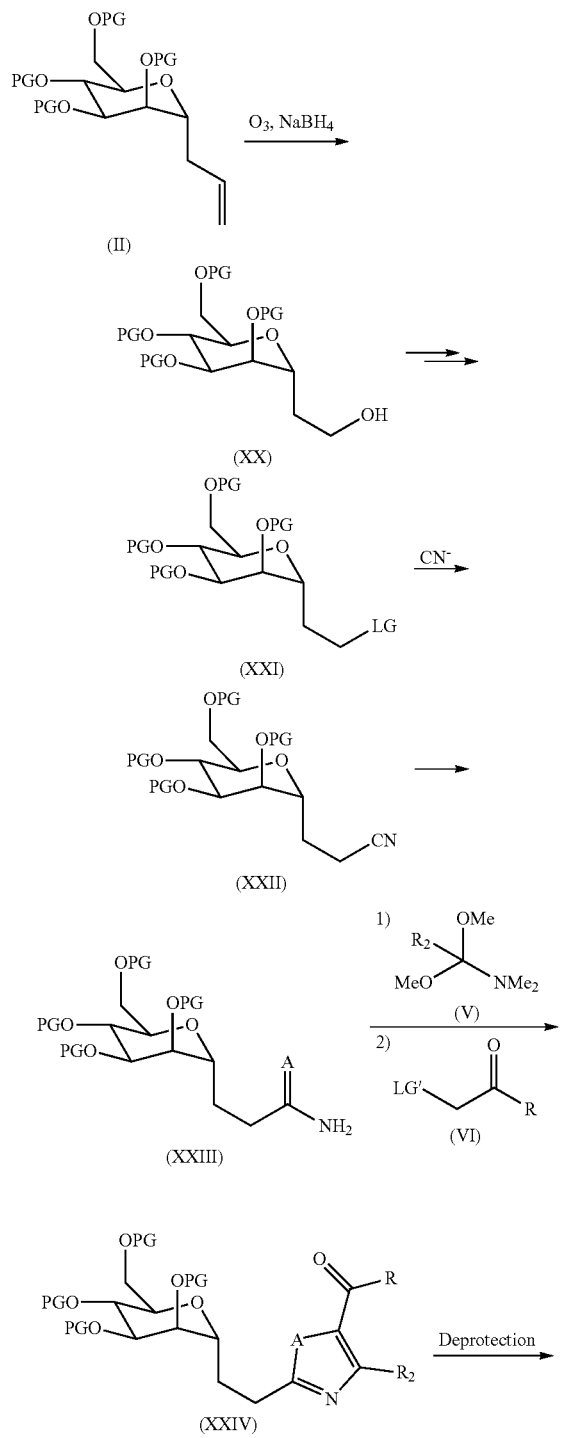

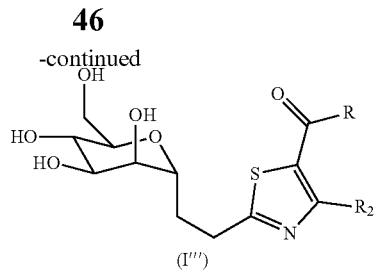

Step a) is carried out using conventional reactions known in the art, in particular using the following reaction sequence: protecting the free hydroxyl groups of mannose, followed by generating of the corresponding oxonium ion in the presence of a Lewis acid, such as trimethylsilyltriflate, and reacting said oxonium with allyltrialkylsilane, in particular allyltrimethylsilane.

Reductive ozonolysis step b) is carried out under conventional conditions known to the one of skill in the art. For instance, the reductive ozonolysis step b) is carried out in methanol or a mixture of dichloromethane and methanol, at low temperature such as a temperature of between −78° C. and room temperature (25° C.). Ozone is the bubbled in the reaction mixture at said low temperature until the reaction mixture turns blue. The reaction is then quenched by addition of a brohydride such as sodium borohydride ($NaBH_4$).

In step c), the resulting alcohol function of the alcohol of formula (XX) is then converted into a leaving such as a sulfonate (preferably mesylate or tosylate) or into a halogen such as bromide, as known in the art.

Step d) is a nucleophilic substitution using a cyanide ion, in particular a cyanide alkaline salt such as potassium cyanide. Step d) is preferably carried out in a polar solvent such as DMF.

Step e) is carried out using reactions known in the art. For instance, the amide of formula (XXIII) (in this case, A represents O) is obtained by hydrolyzing the mannose cyanide of formula (XXII) to the corresponding carboxylic acid, followed by activation of the obtained carboxylic acid, for instance by reaction with an acyl chloride (such as oxalyl chloride or acetyl chloride), and subsequent reaction with aqueous ammonia. The thioamide of formula (XXIII) (in this case, A represents S) is for instance obtained by reacting the amide of formula (XXIII) (i.e. wherein A represents O) with a sulfuring agent such as phosphorous pentasulfide.

Cyclization step f) is typically carried out by reacting intermediate (XXIII) with a N,N-Dimethylalcanamide di($C_1$-$C_6$)-alkyl acetal (such as N,N-dimethylacetamide dimethyl acetal or N,N-dimethylacetamide dimethyl acetal) in an aprotic polar solvent such as acetonitrile, at a temperature of between 40° C. and the boiling point of the solvent, preferably 60° C. An α-halogenoketone of formula (VI) is then added and the reaction mixture is further heated in the presence of a base such as a tertiary amine (preferably trimethylamine, diisopropylethylamine or hexamethyldisilazane) and of an α-halogenoketone of formula (VI), optionally activated by addition of sodium iodide, to yield a heterocyclic mannose derivative of formula (VII).

Conventional reaction conditions known in the art, such as described for instance in Greene's "Protective Groups In Organic synthesis", are used for deprotection step g).

When carried out, step h) is conducted according to conventional reactions known in the art, such as described in Greene's "Protective Groups In Organic synthesis".

Of note, the group PG listed in intermediates (II), (III), (IV), (VII), (VIII), (X), (XI), (XII), (XVII), (XVIII), (XIX), (XX), (XXI), (XXII), (XXIII) and (XXIV) may be identical or different. In particular, during a specific reaction sequence, the PG group may be changed for improving the global reactivity of the intermediate in a particular reaction step.

Definitions

The term "halogen", as used in the present invention, refers to a fluorine, bromine, chlorine or iodine atom, preferably a chlorine, bromine or fluorine atom.

The term "($C_1$-$C_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "($C_2$-$C_6$)alkenyl", as used in the present invention, refers to a straight or branched unsaturated hydrocarbon chain containing from 2 to 6 carbon atoms and comprising at least one double bond including, but not limited to, ethenyl, propenyl, butenyl, pentenyl, hexenyl and the like.

The term "($C_2$-$C_6$)alkynyl", as used in the present invention, refers to a straight or branched unsaturated hydrocarbon chain containing from 2 to 6 carbon atoms and comprising at least one triple bond including, but not limited to, ethynyl, propynyl, butynyl, pentynyl, hexynyl and the like.

The term "($C_3$-$C_{10}$)cycloalkyl", as used in the present invention, refers to a hydrocarbon monocyclic or bicyclic (fused) ring having 3 to 10 carbon atoms including, but not limited to, cyclopropyl, cyclopentyl, cyclohexyl and the like.

The term "($C_5$-$C_{10}$)cycloalkenyl", as used in the present invention, refers to a hydrocarbon monocyclic or bicyclic (fused) ring having 5 to 10 carbon atoms and comprising at least one double bond including, but not limited to, cyclopentenyl, cyclohexenyl and the like.

The term "heterocycloalkyl", as used in the present invention, refers to a hydrocarbon monocyclic or bicyclic (fused) ring having 3 to 10 ring atoms, containing at least one heteroatom, preferably 1 or 2 heteroatoms, in the ring. The heteroatom is preferably selected from O, N or S, and the S atom may be mono or dioxidized, i.e. the sulphur atom may be S, S(O) or $SO_2$, heterocycloalkyls include, but are not limited to, epoxide, aziridine, pyrrolidinyl, tetrahydrofuranyl, tetrahydrothiophenyl, tetrahydropyranyl, piperidinyl, piperazinyl, morpholinyl, thiomorpholinyl.

The term "heterocycloalkenyl", as used in the present invention, refers to a hydrocarbon monocyclic or bicyclic (fused) ring having 5 to 10 ring atoms, containing at least one heteroatom, preferably 1 or 2 heteroatoms, in the ring, and comprising at least one double bond. The heteroatom is preferably selected from O, N or S, and the S atom may be mono or dioxidized, i.e. the sulphur atom may be S, S(O) or $SO_2$, heterocycloalkenyls include, but are not limited to, pyrrolyl, dihydrofuranyl, dihydrothiophenyl, dihydropyranyl, tetrahydropyridinyl, dihydrooxazinyl, oxindolyl, benzothiazinyl, benzothiazinonyl, phthalimidyl, indolinyle, isoindolinyle.

As used herein, an "aryl group" may be an aromatic or heteroaromatic group.

The term "aromatic group" as used herein alone or as part of another group denotes optionally substituted homocyclic aromatic groups, preferably monocyclic or bicyclic (fused) groups, containing from 6 to 12 carbons in the ring portion, such as phenyl, naphthyl and indenyle. Phenyl and naphthyl are the most preferred aromatic groups.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 to 3 heteroatoms preferably selected from O, N and S in the ring, and may be bonded to the remainder of the molecule through a carbon or heteroatom. Exemplary heteroaromatics include furyl, thiophenyl, pyrrolyl, isoxazolyl, oxazolyl, isothiazolyl, thiazolyl, imidazolyl, triazolyl, pyridyl, pyrimidinyl, pyrazinyl, pyridazinyl, indolyl, isoindolyl, chromene-2-onyle (or coumarinyl), benzoxazolyl, benzothiazolyl, benzotriazolyl, quinolinyl, or isoquinolinyl and the like. Preferably, the heteroaromatic group is selected from a pyrrolyl, thiophenyl, isoxazolyl, triazolyl, oxazolyl, thiazolyl, benzothiazolyl, benzotriazolyl, pyrindinyl and pyrazinyl, in particular pyrrolyl, isoxazolyl, 1,3-oxazolyl, 1,3-thiazolyl, 1,2,3-triazolyl, benzothiazolyl, benzotriazolyl, pyrindinyl and pyrazinyl.

As used herein, the term "alkylaryl" refers to a ($C_1$-$C_6$) alkyl-aryl group. Preferably, the alkylaryl group is a benzyl group, a methyl-(1,2,3)-triazole or a methylbenzotriazole.

The term "carbohydrate" as used in the present invention refers to erythrose, threose, ribose, arabinose, xylose, lyxose, allose, altrose, glucose, mannose, gulose, idose, galactose, talose, erythrulose, ribulose, xylulose, psicose, fructose, sorbose, tagatose or a cyclodextrine, in particular α-, β- or γ-cyclodextrin, in D or L form. The carbohydrate of the invention is not protected (i.e. it does not contain any O-protecting groups), except for the anomeric OH group which may be replaced by a methoxy (OMe) group. Preferably, the carbohydrate is a pyranose carbohydrate, such as galactose or mannose, advantageously in its D form. The carbohydrate is preferably linked to the rest of the compound via a $CH_2$ link, preferably on the anomeric position or on the C6 position of the carbohydrate in the case of pyranose carbohydrates.

The term "O-Protecting group" (or OPG) as used in the present invention refers to a substituent which protects hydroxyl groups against undesirable reactions during synthetic procedures such as those O-protecting groups disclosed in Greene's "Protective Groups In Organic synthesis". O-protecting groups comprise ($C_1$-$C_6$)alkyl groups, such as methyl, ethyl tert-butyl; substituted methyl ethers, for example, methoxymethyl (MOM), benzyloxymethyl, 2-methoxyethoxymethyl, 2-(trimethylsilyl) ethoxymethyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl (TBS) and t-butyldiphenylsilyl; and esters prepared by reacting the hydroxyl group with a carboxylic acid for example, acetate, propionate, benzoate and the like. Preferably, in the present invention, the O-Protecting group is a CO—($C_1$-$C_6$)-alkyl, a COaryl or a tri-($C_1$-$C_6$)alkylsilyle, even more preferably a benzoyl group ($COCH_2Ph$), an acyl group ($C(O)CH_3$) or a trimethylsilyl (TMS) group.

The term "leaving group" as used in the present invention refers to a chemical group which can be easily replaced with a nucleophile during a nucleophilic substitution reaction, the nucleophile being in particular an alcohol (i.e. a molecule carrying a group OH), a thiol (i.e. a molecule carrying a group SH) or an amine (i.e. a molecule carrying a group $NHR_3$ with $R_3$ as defined above, preferably $NH_2$). Such a leaving group can be in particular a halogen atom or a sulfonate. The sulfonate is in particular a group —$OSO_2$—$R_{10}$ with $R_{10}$ representing a ($C_1$-$C_6$)alkyl, aryl, aryl-($C_1$-$C_6$)-alkyl or ($C_1$-$C_6$)-alkyl-aryl group. The sulfonate may be a mesylate ($CH_3$—$S(O_2)O$—), a triflate (CF3-$S(O)_2O$—) or a tosylate (p-Me-$C_6H_4$—$S(O)_2O$—). Preferably, in the present invention, the leaving group is an halogen atom or a mesylate group, more specifically a chlorine atom, a bromine atom or a mesylate group.

Also, in the present invention, Me stands for methyl, Ph stands for phenyl, Bn stands for benzyl and Bz stands for benzoyl, Ac stands for acetyl, and TMS stands for trimethylsilyl. More generally, the abbreviations used to refer to chemical groups have the meaning commonly known in the art.

DESCRIPTION OF THE FIGURES

FIG. 5. Dose-dependent inhibitory effects on the ability of the AIEC strain LF82 to adhere to T84 cells obtained with HM and the compounds of the following examples in a preincubation protocol. Horizontal scale: concentration of inhibitors expressed in μM. Results are expressed as percentage of bacteria adhering to the cells (means±SEM); 100% corresponds to adhesion in the absence of any treatment (LF82, control).

FIG. 6. Plasmatic concentrations after administration of Compound 1b to Sprague Dawley rats at 1 mg/kg by intravenous route (squares) and 10 mg/kg by oral route (diamonds). The X-axis represents the time (in hours), the Y-axis represents the plasmatic concentration of compound 1b in ng/L.

EXAMPLES

Figure 1:
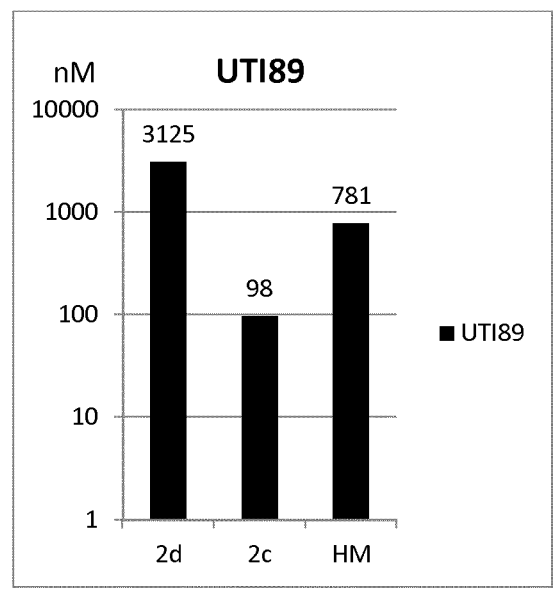
FIG. 1. Inhibition of Haemagglutination by the uropathogenic *E. coli* strain UTI89. The formation of the cross-linked network due to the interaction of the *E. coli* FimH adhesins with the glycocalyx of the erythrocytes was prevented at a certain concentration of inhibitors. The minimal inhibitory concentration (MIC) for the tested compounds is expressed in nanomolar (nM) on a logarithmic scale. Due to serial dilutions, the error is ±one well or a factor of two.

The following examples are included to demonstrate preferred embodiments of the invention. All matter set forth or shown in the following examples and accompanying drawings is to be interpreted as illustrative and not in a limiting sense.

I. Synthesis

Materials and Methods:

NMR spectra were recorded at room temperature with a Bruker Avance 300 Ultra Shield or eBruker Avance III 400 spectrometer, and chemical shifts are reported in parts per million (ppm) relative to tetramethylsilane or a residual solvent peak ($CDCl_3$: 1H, δ=7.26; 13C, δ=77.2; DMSO-$d^6$: 1H, δ=2.54, 13C, δ=40.4). Peak multiplicity is reported as: singlet (s), doublet (d), triplet (t), quartet (q), multiplet (m), and broad (br).

Optical rotations were measured on a 343 Perkin Elmer at 20° C. in a 1 cm cell in the stated solvent.

High resolution mass spectra (HRMS) were obtained by electrospray ionization (ESI) on a Micromass-Waters Q-TOF Ultima Global or with a Bruker Autoflex III Smart-Beam spectrometer (MALDI).

Abbreviations

| | |
|---|---|
| RT | Room temperature |
| TLC | Thin layer chromatography |
| eq | Molar equivalent |
| Da | Dalton |
| GP | General Procedure |
| ACN | acetonitrile |
| DCM | dichloromethane |
| DMA-DMA | N,N-Dimethylacetamide dimethyl acetal |
| DMF | dimethylformamide |
| DMF-DMA | N,N-Dimethylformamide dimethyl acetal |
| EDTA | (Ethylenedinitrilo)tetraacetic acid |
| PE | Petroleum ether |
| THF | Tetrahydrofuran |
| AcOEt | Ethyl Acetate |
| Bn | Benzyl |

General Procedure (1): Replacement of Acetyl Groups by Benzyl Groups.

The acetylated carbohydrate (1 eq) was solubilised in a mixture of DCM/MeOH 1:1 (1 mL/mmol), and MeONa (0.1M in MeOH, 0.55 eq) was added to the mixture, which was stirred at RT for 3 h. The reaction mixture was then concentrated and solubilised in DMF (3 mL/mmol). NaH (6 eq) was added at 0° C., and the reaction mixture was stirred over 1 h at this temperature. Then BnBr (6 eq) was slowly added at 0° C. The mixture was allowed to warm at RT overnight, hydrolysed with saturated aqueous NH$_4$Cl, and extracted several times with Et$_2$O. The organic layers were united, washed several times with brine, dried over MgSO$_4$, filtered and concentrated under vacuum. The residue was purified by flash chromatography on silica gel.

General Procedure (2): Activation of Alcohol by Methanesulfonyl Group

The alcohol derivative was solubilized in pyridine; methanesulfonyle chloride (2 eq) was added. The reaction mixture was stirred 1 h, then diluted by DCM and pyridine was removed thanks to washings with 2M aqueous H$_2$SO$_4$ and saturated aqueous CuSO$_4$. The organic layer was then washed by brine, dried over MgSO$_4$, filtered and concentrated under vacuum. The residue was purified by flash chromatography on silica gel.

General Procedure (3): Substitution of Methanesulfonyl Group by KCN

The methanesulfonyle derivative (1 eq) was solubilised in DMF (4 mL/mmol), then KCN (4 eq) was added and the mixture was warmed to 90° C. overnight. The reaction was quenched by addition of saturated aqueous NH$_4$Cl, extracted several time with Et$_2$O, washed with brine, dried over MgSO$_4$ and concentrated under vacuum. The residue was purified by flash chromatography on silica gel.

General Procedure (4): Formation of the Thioamide from Nitrile

The nitrile derivative (1 eq) was dissolved in thioacetic acid, and Di-O-ethyl dithiophosphate (2 eq) was added. The mixture was heated to 60° C. until completion of the reaction (monitored by TLC), and then saturated aqueous NaHCO$_3$ was added. The product was extracted with DCM, washed several time with saturated aqueous NaHCO$_3$, dried over MgSO$_4$ and concentrated under vacuum. The residue was purified by flash chromatography on silica gel.

General Procedure (5): Condensation of DMF-DMA

The thioamide (1 eq) was dissolved in acetonitrile, DMF-DMA (1.3 eq) was added and the mixture was warmed to 60° C. for 40 min. The mixture was concentrated under vacuum, and the crude product was purified by flash chromatography on silica gel.

General Procedure (6): Cyclisation for C-Linked Thiazoles

The thiazadiene derivative (1 eq) was solubilised in ACN, and α-halogenoketone (1.2 eq) was added with a 0.2 eq of potassium iodide. After 15 min of stirring at RT, triethylamine (2 eq) was added, and the mixture was heated to 60° C. until completion of the reaction (monitored by TLC). The mixture was washed with brine, extracted with AcOEt, dried over MgSO$_4$, and concentrated under vacuum. The residue was purified by flash chromatography on silica gel.

General Procedure (7): "One Pot" Cyclisation

The thioamide (1 eq) was dissolved in acetonitrile, DMF-DMA (1.3 eq) was added and the mixture was warmed to 60° C. for 40 min. After completion of the reaction (monitored by TLC), α-halogenoketone (1.2 eq) was added with a 0.2 eq of potassium iodide. After 15 min of stirring at RT, triethylamine (2 eq) was added, and the mixture was heated to 60° C. until completion of the reaction (monitored by TLC). The mixture was washed with brine, extracted by AcOEt, dried over MgSO$_4$, and concentrated under vacuum. The residue was purified by flash chromatography on silica gel.

General Procedure (8) Deprotection of Acetyl Groups

The protected carbohydrate (1 eq) was dissolved in methanol, and sodium methoxide (0.2 eq) was added. The mixture was stirred at RT and completion of the reaction was monitored by TLC. After completion, water was added, followed by addition of acidic Amberlyt resin (Amberlite® IR120 under hydrogen form) until the pH of the reaction mixture was around 5. After filtration of the resin and concentration in vacuum, the crude product was purified by flash chromatography on silica gel.

General Procedure (9) Deprotection of Benzyl Groups with BCl$_3$

The protected carbohydrate (1 eq) was dissolved in DCM under inert atmosphere, and the temperature was lowered to −10° C. A 1M solution of BCl$_3$ in DCM (3 eq per BnO group to be deprotected) was then added dropwise at −10° C., then the mixture was allowed to warm to RT over 20 h. Methanol was added slowly, and the mixture was concentrated under vacuum. Co-evaporation was repeated 4 times. Then the resulting product was purified by flash chromatography on silica gel.

General Procedure (10) Click Chemistry

The azide derivative and the alkyne derivative were dissolved in dioxane, and water was added. Graphite supported copper oxide nanoparticles (Halluin et al, 2015) were added (0.05 eq per azide), and the mixture was heated to 70° C. until completion. The mixture was filtered over celite, and rinsed with dioxane or other suitable solvent, then concentrated and purified.

General Procedure A: Cyclisation "One Pot"

The thiourea 2c4 or 2k1 (1 eq) was dissolved in THF (20 mL/mmol), DMF-DMA (1.3 eq) was added and the mixture was warmed at 60° C. for 40 min. After completion of adduct formation, as indicated by TLC, α-halogenoketone (1.2 eq) and KI (0.05 eq) were added. After 15 min of stirring at room temperature, triethylamine (2 eq) was added and the mixture was heated to 70° C. until completion. The mixture was washed with brine, extracted by EtOAc, dried over MgSO$_4$ and concentrated in vacuum. The residue was purified by flash chromatography on silica gel.

General Procedure B: O-Acetyl Deprotection with Zemplen Conditions

The protected mannosyl amide (1 eq) was dissolved in dry MeOH (30 mL) and sodium methoxide (1 M solution in MeOH, 10% mol per AcO) was added. The mixture was stirred for 4 h, neutralized with Amberlite IR120 (H), filtered and the solvents evaporated to dryness. The substrate was dissolved in water and subjected to lyophilization.

General Procedure C: O-Benzyl Deprotection with $BCl_3$

To a solution of per-benzylated mannose derivative in dry DCM (40 mL/mmol), at −10° C. and under $N_2$, was added dropwise 1M $BCl_3$ in DCM (3 equiv/BnO). After 10 h of stirring, MeOH (10 mL/mmol) was added, the mixture was warmed up at room temperature and concentrated in vacuo.

Example 1: Compounds of Formula (I) Wherein Y is a Single Bond

Compound 1a

Intermediate 1a 1: 2,3,4,6-tetra-O-benzyl-1-allyl-α-D-mannopyranose

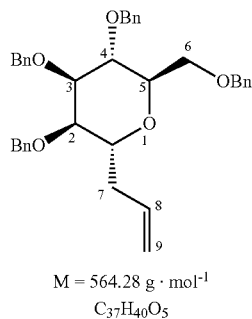 [SMILES: C=CC[C@H]1O[C@H](COCc2ccccc2)[C@@H](OCc2ccccc2)[C@H](OCc2ccccc2)[C@@H]1OCc1ccccc1]

M = 564.28 g · mol⁻¹
$C_{37}H_{40}O_5$ 2,3,4,6-tetra-O-benzyl-1-acetyl-D-mannopyranose (3.9 g, 6.7 mmol, obtained from D-mannose as described in *J. Org. Chem.*, 1997, 62 (20), pp 6961-6967) was dissolved in dry acetonitrile (60 mL), allyltrimethylsilane (1.3 eq) was added under nitrogen, and cooled to 0° C. TMSOTf (0.5 eq, 604 mL)) was added slowly, then the mixture was sonicated in a bath kept under 10° C. with ice for 20 min, and give a yellow solution. The mixture was quenched with triethylamine (2 eq, 1.8 ml), then concentrated under vacuum, and purified by flash chromatography on silicagel (PE/AcOEt, 95-5 to 9-1), to afford 3.1 g of the desired product, in a 82% yield.

$^1$H NMR (400 MHz, $CDCl_3$): δ (ppm): 7.23-7.38 (m, 18H, HBn), 7.18-7.23 (m, 2H, HBn), 5.76 (ddt, $^3$J=7.0/9.6/14.0 Hz, 1H, H8), 5.04 (m, 1H, H9), 5.00 (m, 1H, H9'), 4.70 (d, $^2$J=11.6 Hz, 1H, H $CH_2Bn$), 4.50-4.62 (m, 7H, H $CH_2Bn$), 4.04 (ddd, $^3$J=4.74/6.26/7.54 Hz, 1H, H1), 3.80-3.88 (m, 2H, H5+H4), 3.74-3.80 (m, 2H, H3+H6), 3.71 (dd, $^3$J=3.6/10.3 Hz, 1H, H6'), 3.62 (dd, $^3$J=3.0/4.7 Hz, 1H, H2), 2.33 (m, 2H, H7). $[α]_D$=+15.1 (c=1 g/100 mL, $CHCl_3$, 20° C., 589.3 nm).

HRMS, MALDI: $[M+Na^+]_{calc}$=587.2768 Da/$[M+Na^+]_{mes}$=587.2766 Da.

Intermediate 1a2: methyl 2-(2,3,4,6-tetra-O-benzyl-α-D-mannopyranosyl) acetate

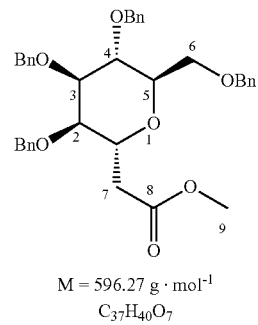 [SMILES: COC(=O)C[C@H]1O[C@H](COCc2ccccc2)[C@@H](OCc2ccccc2)[C@H](OCc2ccccc2)[C@@H]1OCc1ccccc1]

M = 596.27 g · mol⁻¹
$C_{37}H_{40}O_7$ 2,3,4,6-tetra-O-benzyl-1-allyl-α-D-mannopyranose (intermediate 1a1) (3.1 g, 5.49 mmol) was dissolved in DCM (enough to allow the bubbling), then a 2.5 M sodium methanolate in methanol was added (20 mL). The mixture was cooled to −78° C., then ozone was bubbled. The mixture became quickly yellow, and the bubbling was continued until a green/blue colour appeared. Then ozone was replaced by nitrogen, and dimethylsulfide (3 mL) was added. The mixture was allowed to warm to room temperature, then washed by 2M aqueous HCl, brine, dried over $MgSO_4$, and concentrated under vacuum.

The resulting oil was purified on silica gel PE/AcOEt 90:10 to 80:20, to afford 1.82 g of the desired product as colourless oil in 57% yield.

$^1$H NMR (400 MHz, $CDCl_3$): δ (ppm): 7.20-7.34 (m, 20H, HBn), 4.49-4.61 (m, 8H, $H_{CH2Bn}$), 4.47 (m, 1H, H1), 3.92 (m, 1H, H5), 3.84 (t, $^3$J=5.8 Hz, 1H, H4), 3.77-3.81 (m, 3H, H3+H6), 3.63 (dd, $^3$J=2.8/6.6 Hz, 1H, H2), 3.62 (s, 3H, H9), 2.67 (dd, A part of ABX system, $^{AB}$J=15.2 Hz, $^{BX}$J=5.3 Hz 1H, H7'), 2.54 (dd, A part of ABX system, $^{AB}$J=15.2 Hz, $^{BX}$J=8.3 Hz 1H, H7').

$[α]_D$=+9.2 (c=0.55 g/100 mL, $CHCl_3$, 20° C., 589.3 nm).

HRMS, MALDI: $[M+Na^+]_{calc}$=619.2666 Da/$[M+Na^+]_{mes}$=604.2684 Da.

Intermediate 1a3: 2-(2,3,4,6-tetra-O-benzyl-α-D-mannopyranosyl) acetamide

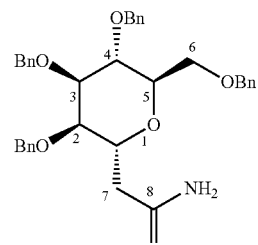

M = 581.697 g · mol⁻¹
$C_{36}H_{39}NO_6$

Intermediate 1a2 (3.76 g, 6.31 mmol) was dissolved in THF (50 mL), and lithium hydroxide was added (10 eq, 1.5 g). Water was added until total solubility, then the mixture was stirred at room temperature overnight (or warmed to reflux during 2 h). The solution was acidified by HCl 4M, then extracted with AcOEt, and washed with brine, dried over MgSO$_4$, and concentrated under vacuum.

The crude oil was dissolved in DCM (60 mL), and cooled to 0° C. under nitrogen. A drop of DMF was added, and then oxalyl chloride (4 eq, 2.18 mL) was added slowly. The mixture was stirred at room temperature 6 h, and concentrated in vacuum (broke with nitrogen). The resulting oil was dissolved in DCM, and poured in a cold solution of 25% aqueous ammonia (exothermic reaction). Extracted with DCM, then acidified with 4M HCl, washed with brine, dried over MgSO$_4$, and concentrated under vacuum.

The resulting oil was purified by flash chromatography on silica gel PE/AcOEt 40:60 to 30:70, to afford 2.93 g of the desired product as white powder in 79% yield.

$^1$H NMR (400 MHz, CDCl$_3$): δ (ppm): 7.18-7.36 (20H, m, H-Bn), 5.40 (1H, bs, NH$_2$), 4.43-4.60 (8H, m, H$_{CH2Bn}$), 4.25 (1H, ddd, $^3$J=2.1, $^3$J=8.4, $^3$J=10.2 Hz, H-1), 4.06-4.13 (2H, m, H-6, H—), 3.79 (1H, dd, $^3$J=3.1 Hz $^3$J=4.3 Hz, H-3), 3.57 (1H, dd, $^3$J=2.8 Hz $^3$J=8.1 Hz, H-2), 3.53 (1H, dd, $^3$J=2.4 Hz $^3$J=4.6 Hz, H-4), 3.44 (1H, m, H-6'), 2.68 (1H, dd, $^3$J$_{7-1}$=2.2 Hz $^3$J$_{7-7}$=16.5 Hz, H-7), 2.49 (1H, dd, $^3$J$_{7'-1}$=10.2 Hz $^3$J$_{7-7}$=16.5 Hz, H-7) [α]$_D$=−17.9 (c=1 g/100 mL, CHCl$_3$, 20° C., 589.3 nm).

HRMS, MALDI: [M+Na$^+$]$_{calc}$=604.2670 Da/[M+Na$^+$]$_{mes}$=604.2663 Da.

Intermediate 1a4: 2-(2,3,4,6-tetra-O-acetyl-α-D-mannopyranosyl)acetamide

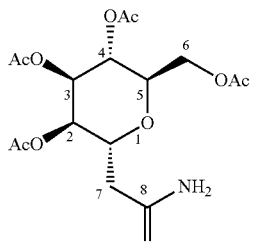

M = 389.13 g · mol$^{-1}$
C$_{16}$H$_{23}$NO$_{10}$

Intermediate 1a3 (2.930 g, 4.97 mmol) was dissolved in a 1:1 mixture of DCM and MeOH (40 mL). Pearlman catalyst (1 g) was added, and the flask was placed under H$_2$ atmosphere overnight. The mixture was the filtrated on decalite, and rinsed with water. The solution was concentrated, and co-evaporated with toluene to remove all water (or lyophilised). The resulting white powder was suspended in pyridine (40 mL), and acetic anhydride (30 eq, 14 mL) was added, with a catalytic amount of DMAP). The mixture was stirred overnight at room temperature, and then concentrated under vacuum, and co-evaporated with toluene (removing pyridine by washing steps result in a loss of product).

The crude product was purified by flash chromatography on silica gel, eluted with AcOEt to afford 1.93 g of the desired product as white powder in 96% yield.

$^1$H NMR (400 MHz, CDCl$_3$): δ (ppm): 6.11 (bs, 1H, NH$_2$), 5.41 (bs, 1H, NH$_2$), 5.28 (dd, $^3$J=3.3/6.3 Hz 1H, H3), 5.10 (dd, $^3$J=3.3/6.6 Hz 1H, H2), 5.06 (dd, $^3$J=5.02/6.2 Hz 1H, H4), 4.48 (dd, A part of ABX system, $^{AB}$J=12.1 Hz, $^{AX}$J=7.9 Hz, 1H, H6), 4.38 (ddd, $^3$J=3.9/6.5/10.0 Hz 1H, H1), 4.22 (dd, B part of ABX system, $^{AB}$J=12.1 Hz, $^{BX}$J=4.0 Hz, 1H, H6'), 4.04 (m, 1H, H5), 2.59 (dd, A part of ABX system, $^{AB}$J=15.5 Hz, $^{BX}$J=9.4 Hz 1H, H7), 2.51 (dd, B part of ABX system, $^{AB}$J=15.5 Hz, $^{BX}$J=3.8 Hz 1H, H7'), 2.11 (s, 3H, CH$_3$OAc), 2.09 (s, 3H, CH$_3$OAc), 2.08 (s, 3H, CH$_3$OAc), 2.07 (s, 3H, CH$_3$OAc).

HRMS, ESI: [M+Na$^+$]$_{calc}$=412.12142 Da/[M+Na$^+$]$_{mes}$=412.12131 Da.

Intermediate 1a5: 2-(2,3,4,6-tetra-O-acetyl-1-α-D-mannopyranosyl)thioacetamide

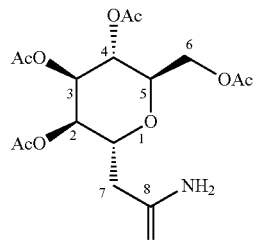

M = 405.11 g · mol$^{-1}$
C$_{16}$H$_{23}$NO$_9$S

Intermediate 1a4 (330 mg, 0.85 mmol) was dissolved in THF; phosphorous pentasulfide (1.1 eq, 207 mg) was added and stirred 1 h at room temperature. The mixture was washed by brine, extracted by AcOEt, dried over MgSO$_4$, and concentrated under vacuum.

The crude product was purified by flash chromatography on silica gel, PE/AcOEt 6:4 to 5:5 to afford 255 mg of the desired product as white powder in 74% yield.

$^1$H NMR (400 MHz, CDCl$_3$): δ (ppm): 7.74 (bs, 1H, NH$_2$), 7.61 (bs, 1H, NH$_2$), 5.27 (dd, $^3$J=3.3/6.0 Hz 1H, H3), 5.08 (dd, $^3$J=3.3/6.9 Hz 1H, H2), 5.03 (dd, $^3$J=4.5/6.1 Hz 1H, H4), 4.48 (dd, A part of ABX system, $^{AB}$J=12.1 Hz, $^{AX}$J=8.1 Hz, 1H, H6), 4.42 (ddd, $^3$J=4.1/6.9/8.3 Hz 1H, H1), 4.22 (dd, B part of ABX system, $^{AB}$J=12. Hz, $^{BX}$J=4.0 Hz, 1H, H6'), 4.07 (m, 1H, H5), 3.05 (dd, A part of ABX system, $^{AB}$J=15.4 Hz, $^{BX}$J=4.0 Hz 1H, H7), 3.00 (dd, B part of ABX system, $^{AB}$J=15.4 Hz, $^{BX}$J=8.4 Hz 1H, H7'), 2.11 (s, 3H, CH$_3$OAc), 2.09 (s, 3H, CH$_3$OAc), 2.08 (s, 3H, CH$_3$OAc), 2.07 (s, 3H, CH$_3$OAc). [α]$_D$=+18.3 (c=0.9 g/100 mL, CHCl$_3$, 20° C., 589.3 nm).

HRMS, MALDI: [M+Na$^+$]$_{calc}$=428.0986 Da/[M+Na$^+$]$_{mes}$=428.0970 Da.

Intermediate 1a6: 5-acetyl-2-(2,3,4,6-tetra-O-acetyl-α-D-mannopyranos-1-yl)methyl)thiazole

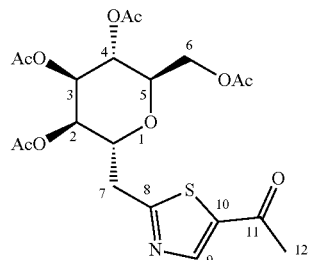

M = 471.11 g · mol$^{-1}$
C$_{20}$H$_{25}$NO$_{10}$S

Prepared following GP (6), starting from Intermediate 1a5 (100 mg, 0.247 mmol) and chloroacetone. After purification over silica gel (PE/AcOEt 4:6), 45 mg of the desired product was obtained in 39% yield, as a slightly yellow oil.

$^1$H NMR (400 MHz, CDCl$_3$): δ (ppm): 8.20 (s, 1H, H9) 5.33 (dd, $^3$J=3.4/6.7 Hz 1H, H3), 5.19 (dd, $^3$J=3.3/6.0 Hz 1H, H2), 5.09 (dd, $^3$J=5.3/6.7 Hz 1H, H4), 4.45 (dd, A part of ABX system, $^{AB}$J=13.0 Hz, $^{AX}$J=8.5 Hz, 1H, H6), 4.36 (ddd, $^3$J=5.6/7.7/11.8 Hz 1H, H1), 4.11 (m, 2H, H5+H6') 3.30-3.79 (m, 1H, H6'), 2.56 (s, 3H, H12), 2.11 (s, 3H, CH$_3$OAc), 2.09 (s, 3H, CH$_3$OAc), 2.08 (s, 3H, CH$_3$OAc), 2.04 (s, 3H, CH$_3$OAc). [α]$_D$=−7.6 (c=0.5 g/100 mL, CHCl$_3$, 20° C., 589.3 nm).

HRMS, MALDI: [M+Na$^+$]$_{calc}$=472.1272 Da/[M+Na$^+$]$_{mes}$=472.1285 Da.

Compound 1a: 5-acetyl-2-((α-D-mannopyranos-1-yl)methyl)thiazole

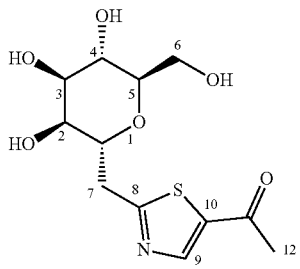

M = 303.08 g · mol$^{-1}$
C$_{12}$H$_{17}$NO$_6$S

Prepared following GP (7), starting from Intermediate 1a6 (87 mg, 0.184 mmol). After purification over silica gel (DCM/MeOH 9:1) and lyophilisation, 25 mg of the desired product was obtained in 45% yield, as a light white solid.

$^1$H NMR (400 MHz, MeOD): δ (ppm): 8.37 (s, 1H, H9), 4.36 (ddd, $^3$J=4.0/4.9/9.2 Hz 1H, H1), 3.83 (dd, $^3$J=6.1/11.8 Hz 1H, H6), 3.78-3.81 (m, 2H, H2+H3) 3.72-3.77 (m, 2H, H6'+H4), 3.62-3.67 (m, 1H, H5), 3.38-3.44 (m, 2H, H7). [α]$_D$=+40.1 (c=1.25 g/100 mL, MeOH, 20° C., 589.3 nm).

HRMS, ESI: [M−H$^-$]$_{calc}$=302.0693 Da/[M−H$^-$]$_{mes}$=302.0692 Da.

Compound 1b

Intermediate 1b1: 5-(4-methyl-2-(pyrazin-2-yl)thiazole-5-carbonyl) 2-((2,3,4,6-tetra-O-acetyl-α-D-mannopyranos-1-yl)methyl)thiazole

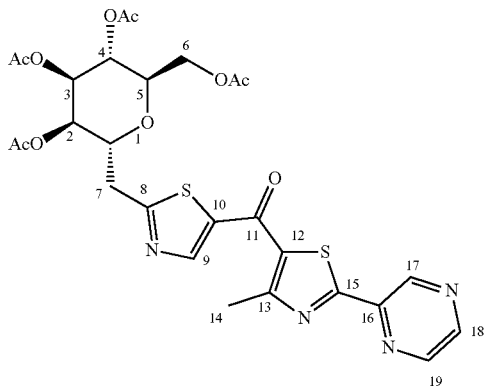

M = 632.12 g · mol$^{-1}$
C$_{27}$H$_{28}$N$_4$O$_{10}$S$_2$

Prepared following GP (6), starting from intermediate 1a6 (70 mg, 0.15 mmol) and 2-bromo-1-[4-methyl-2-(2-pyrazinyl)-1,3-thiazol-5-yl]-1-ethanone (CAS: 423768-43-8). After purification over silica gel (PE/AcOEt 4:6), 52 mg of the desired product was obtained in 55% yield, as a gum.

$^1$H NMR (400 MHz, CDCl$_3$): δ (ppm): 9.46 (d, $^3$J=1.5 Hz, 1H, H19), 8.66 (d, $^4$J=2.6 Hz, 1H, H17), 8.58 (d, $^3$J=1.5 Hz, $^4$J=2.6 Hz, 1H, H17), 8.39 (s, 1H, H9), 5.34 (dd, $^3$J=3.2/6.5 Hz, 1H, H3), 5.20 (dd, $^3$J=3.2/6.0 Hz, 1H, H2), 5.08 (t, $^3$J=6.3 Hz, 1H, H4), 4.47 (dd, $^3$J=8.5/12.8 Hz, 1H, H6), 4.39 (dd, $^3$J=6.4/13.2 Hz, 1H, H1), 4.08-4.15 (m, 2H, H6'+H5), 3.39 (s, 1H, H), 3.37 (s, 2H, H7), 2.78 (s, 3H, H14), 2.11 (s, 3H, CH$_3$OAc), 2.09 (s, 3H, CH$_3$OAc), 2.08 (s, 3H, CH$_3$OAc), 2.04 (s, 3H, CH$_3$OAc). [α]$_D$=−4.6 (c=0.36 g/100 mL, CHCl$_3$, 20° C., 589.3 nm).

HRMS, MALDI: [M+H$^+$]$_{calc}$=633.1320 Da/[M+H$^+$]$_{mes}$=633.1332 Da.

Compound 1b: 5-(4-methyl-2-(pyrazin-2-yl)thiazole-5-carbonyl) 2-((-α-D-mannopyranos-1-yl)methyl)thiazole

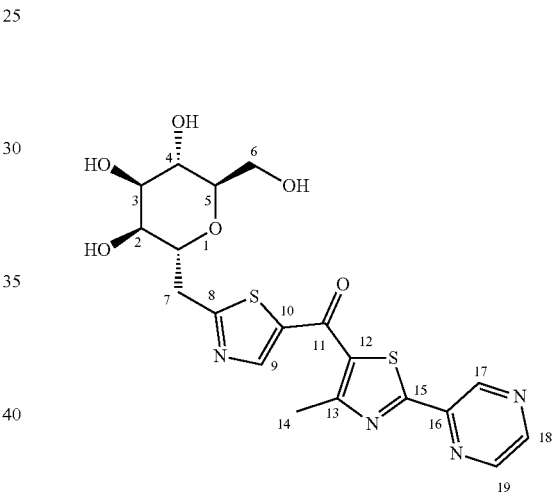

M = 464.08 g · mol$^{-1}$
C$_{19}$H$_{20}$N$_4$O$_6$S$_2$

Prepared following GP (7), starting from intermediate 1b1 Tc5-062-1 (52 mg, 0.082 mmol). After purification over silica gel (DCM/MeOH 9:1) and lyophilisation, 19 mg of the desired product was obtained in 50% yield, as a white powder.

$^1$H NMR (400 MHz, DMSO): δ (ppm): 9.39 (d, $^3$J=1.4 Hz, 1H, H19), 8.85 (d, $^3$J=2.4 Hz 1H, H17), 8.79 (dd, $^3$J=1.4, $^4$J=2.4 Hz 1H, H18), 8.50 (s, 1H, H9), 4.81 (d, $^3$J=4.7 Hz, 1H, OH4), 4.78 (d, $^3$J=4.7 Hz, 1H, OH3), 4.69 (d, $^3$J=5.6 Hz, 1H, OH2), 4.37 (t, $^3$J=5.7 Hz, 1H, OH6), 4.06 (ddd, $^3$J=3.9/5.2/9.1 Hz, 1H, H1), 3.56-3.70 (m, 5H, H6+H4+H3+H2), 3.54 (m, 1H, H5), 3.42 (dd, A part of ABX system, $^{AB}$J=15.7 Hz, $^{AX}$J=3.9 Hz, 1H, H7), 3.30 (dd, B part of ABX system, $^{AB}$J=15.7 Hz, $^{BX}$J=9.3 Hz, 1H, H7), 2.70 (s, 3H, H14). [α]$_D$=+36.5 (c=0.266 g/100 mL, DMSO, 20° C., 589.3 nm).

HRMS, ESI: [M−H$^-$]$_{calc}$=463.0741 Da/[M−H$^-$]$_{mes}$=463.0736 Da.

Compound 1c

Intermediate 1c1

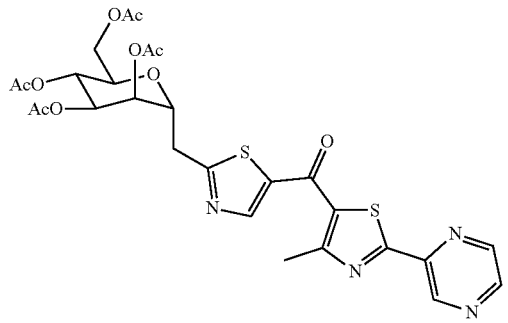

1b1

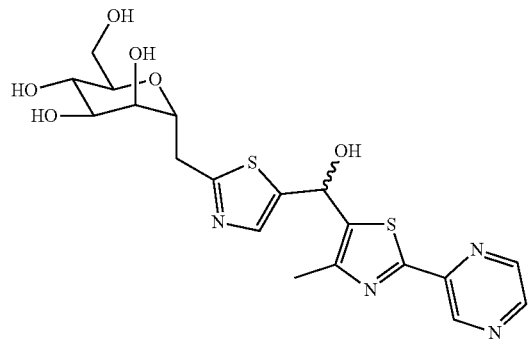

Chemical Formula: $C_{19}H_{22}N_4O_6S_2$
Exact Mass: 466.0981
Molecular Weight: 466.5270

According to the general procedure B, using the alcohol 1c1 (17 mg, 0.027 mmol) as starting material, the derivative 1c was obtained after lyophilization (11 mg, 0.024 mmol, 87%, 1:1 mixture of diasteroisomers R/S) as an amorphous white solid.

$^1$H NMR (400 MHz, MeOD) as an homotopic mixture of two diastereomers δ 2.43 (6H, s, thiazol), 3.34 (4H, m, H-7R, H-7S), 3.62 (2H, m, H-5R, H-5S), 3.69-3.93 (12H, m), 4.23 (2H, m, H-1R, H-1S), 6.38 (2H, s, H-11R, H-11S), 7.58 (2H, s, thiazols), 8.60 (4H, s), 9.27 (2H, s).

m/z [M+Na]$^+$ 489; HRMS (ESI) m/z calcd for $C_{19}H_{22}N_4O_6S_2Na$ [M+Na]$^+$ 489.0857, found 489.0878.

1. Example 2: Compounds of Formula (I) wherein Y=—CH$_2$—, —O—, —S—, —NH—

Compound 2a (Y=—CH$_2$—)

Intermediate 2a 1: 2,3,4,6-tetra-O-benzyl-1-(2-hydroxyethyl)-α-D-mannopyranose

1c1

To a solution of the ketone 1b1 (95 mg, 0.150 mmol) in MeOH (3 mL), at 0° C. and under N$_2$, was added NaBH$_4$ (3.4 mg, 0.090 mmol). After 1 h, the mixture was diluted with DCM and washed with 1M HCl and brine. The crude was purified by silica gel column chromatography (EtOAc) to give the alcohol 1c1 (70 mg, 0.110 mmol, 73%, 1:1 mixture of diasteroisomers R/S) as a colorless oil.

$^1$H NMR (400 MHz, CDCl$_3$) δ 2.00 (3H, s, AcO), 2.03 (3H, s, AcO), 2.049 (3H, s, AcO), 2.051 (3H, s, AcO), 2.068 (3H, s, AcO), 2.075 (3H, s, AcO), 2.077 (6H, s, 2×AcO), 2.437 (3H, s, thiazol), 2.442 (3H, s, thiazol), 3.31 (4H, m, H-7R, H-7S), 4.08 (4H, m, H-5R, H-5S, H-6aR, H-6aS), 4.38 (4H, m, H-1R, H-1S, H-6bR, H-6bS), 5.11 (2H, dd, $J_{4,3}$=7.2 Hz, $J_{4,5}$=6.1 Hz, H-4R, H-4S), 5.19 (2H, dd, $J_{2,1}$=5.3 Hz, $J_{2,3}$=3.3 Hz, H-2R, H-2S), 5.29 (1H, dd, $J_{3,2}$=3.3 Hz, $J_{3,4}$=1.4 Hz, H-3R or H-3S), 5.31 (1H, dd, $J_{3,2}$=3.3 Hz, $J_{3,4}$=1.4 Hz, H-3R or H-3S), 6.33 (2H, bs, H-11R, H-11S), 7.54 (2H, m, H-9R, H-9S), 8.52 (2H, dd, $J_{18,19}$=2.6 Hz, $J_{19,17}$=1.6 Hz, H-18R, H-18S), 8.56 (2H, d, $J_{17,18}$=2.5 Hz, H-17R, H-17S), 9.34 (2H, d, $J_{19,18}$=1.5 Hz, H-19R, H-19S).

m/z [M+H]$^+$ 634; HRMS (ESI) m/z calcd for $C_{27}H_{31}N_4O_{10}S_2$[M+Na]$^+$ 635.1476, found 635.1474.

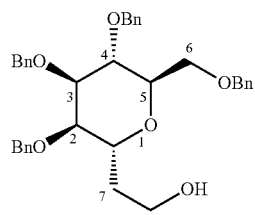

M = 568.28 g·mol$^{-1}$
$C_{36}H_{40}O_6$

Intermediate 1a2 (1.1 g, 1.95 mmol) was dissolved in DCM/MeOH 9:1, in a volume adapted to fit the ozonolysis apparatus, and the temperature was decreased to −78° C. Ozone was then bubbled until the mixture was blue, then the remaining ozone was chased by bubbling N$_2$. Sodium borohydride was added, and the mixture was allowed to warm to RT over 2 h. The mixture was hydrolysed using 30 mL of 1M aqueous HCl, washed with brine, dried over MgSO$_4$, and concentrated under vacuum.

The residue was purified on silica gel (PE/AcOEt: 6/4) to afford 900 mg of the desired product as colourless oil in 81% yield.

$^1$H NMR (400 MHz, CDCl$_3$): δ (ppm): 7.19-7.33 (m, 20H, HBn), 4.49-4.62 (m, 8H, H$_{CH2Bn}$), 4.16 (ddd, $^3$J=3.5/6.0/9.9 Hz, 1H, H1), 3.97 (ddd, $^3$J=4.7/7.8/9.0 Hz, 1H, H5), 3.74-3.82 (m, 4H, H8+H6+H3), 3.71 (t, $^3$J=5.6 Hz, 1H, H4), 3.63 (dd, $^3$J=4.1/10.2 Hz, 1H, H6'), 3.60 (dd, $^3$J=2.9/6.2 Hz, 1H, H2), 1.72-1.92 (m, 2H, H7). [α]$_D$=+13.9 (c=0.5 g/100 mL, CHCl$_3$, 20° C., 589.3 nm).

HRMS, MALDI: [M+Na$^+$]$_{calc}$=591.2717 Da/[M+Na$^+$]$_{mes}$=591.2732 Da.

Intermediate 2a2:
2-(2,3,4,6-tetra-O-benzyl-α-D-mannopyranosyl) ethyl methanesulfonate

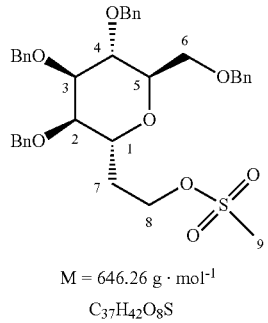 [SMILES: CS(=O)(=O)OCC[C@H]1O[C@H](COCc2ccccc2)[C@@H](OCc2ccccc2)[C@H](OCc2ccccc2)[C@@H]1OCc1ccccc1 ; "C37H42O8S"]

M = 646.26 g · mol$^{-1}$
C$_{37}$H$_{42}$O$_8$S

Prepared following GP (1), starting from intermediate 2a1 (3.23 g, 5.68 mmol). The resultant oil was purified on silica gel (PE/AcOEt 70:30), to afford 3.49 g of the desired product as colourless oil in 95% yield.

$^1$H NMR (400 MHz, CDCl$_3$): δ (ppm): 7.19-7.36 (m, 20H, HBn), 4.46-4.60 (m, 8H, H$_{CH2Bn}$), 4.28-4.33 (m, 2H, H8) 4.06 (ddd, $^3$J=3.6/6.7/10.1 Hz, 1H, H1) 3.89 (m, 1H, H5), 3.74-3.80 (m, 3H, H6+H4+H3), 3.69 (dd, $^3$J=4.7/10.1 Hz, 1H, H6'), 3.57 (dd, $^3$J=2.5/6.5 Hz, 1H, H2), 2.88 (s, 3H, H8), 2.02-2.12 (m, 1H, H7), 1.86-1.96 (m, 1H, H7'). [α]$_D$=+20.4 (c=0.5 g/100 mL, CHCl$_3$, 20° C., 589.3 nm).

HRMS, MALDI: [M+Na$^+$]$_{calc}$=669.2493 Da/[M+Na$^+$]$_{mes}$=669.2518 Da.

Intermediate 2a3:
3-(2,3,4,6-tetra-O-benzyl-α-D-mannopyranosyl) propionitrile

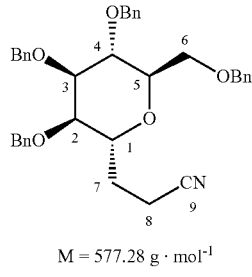

M = 577.28 g · mol$^{-1}$
C$_{37}$H$_{39}$NO$_5$

Prepared following GP (2), starting from intermediate 2a2 (660 mg, 1.02 mmol). The resultant oil was purified on silica gel PE/AcOEt 80:20 to 70:30, to afford 569 mg of the desired product as colourless oil in 97% yield.

$^1$H NMR (400 MHz, CDCl$_3$): δ (ppm): 7.19-7.39 (m, 20H, HBn), 4.40-4.56 (m, 8H, H$_{CH2Bn}$), 43.89-3.99 (m, 2H, H1+H5), 3.77-3.83 (m, 2H, H3+H6), 3.74 (dd, $^3$J=3.3/4.8 Hz, 1H, H4), 3.68 (dd, $^3$J=5.3/10.1 Hz, 1H, H6), 3.53 (dd, $^3$J=2.8/7.7 Hz, 1H, H2), 2.32-2.47 (m, 2H, H8), 1.98-2.08 (m, 1H, H7), 1.79 (m, 1H, H7). [α]$_D$=+34.9 (c=0.5 g/100 mL, CHCl$_3$, 20° C., 589.3 nm).

HRMS, MALDI: [M+Na$^+$]$_{calc}$=600.2720 Da/[M+Na$^+$]$_{mes}$=600.2713 Da.

Intermediate 2a4: 3-(2,3,4,6-tetra-O-acetyl-α-D-mannopyranosyl)propionitrile

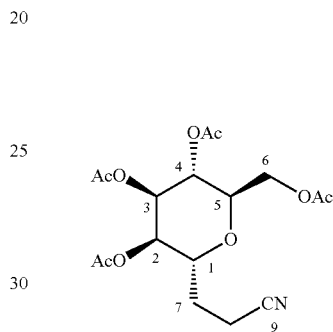

M = 385.13 g · mol$^{-1}$
C$_{17}$H$_{23}$NO$_9$

Intermediate 2a3 (1 g, 1.73 mmol) was solubilised in DCM/MeOH (9:1) (40 mL), and Pd/C was added (500 mg). The mixture was placed under H2 atmosphere, and stirred during 6 h the reaction was monitored by TLC (DCM/MeOH 8:2). After filtration, the mixture was concentrated, diluted in pyridine, and acetic anhydride (3.3 mL, 20 eq) was added followed by a catalytic amount of DMAP. The mixture was stirred overnight, and then extracted by toluene. Washed by a 2M solution of HCl, then water, NaHCO3 and finally brine, dried over MgSO$_4$, and concentrated under vacuum.

The residue was purified on silica gel (PE/AcOEt 1:1) to afford 307 mg of the desired product as colourless oil (46% yield).

$^1$H NMR (400 MHz, CDCl$_3$): δ (ppm): 5.25 (dd, $^3$J=3.2/6.6 Hz, 1H, H3), 5.04-5.07 (m, 2H, H2+H4), 4.58 (dd, $^3$J=7.8/12.2 Hz, 1H, H6), 4.10 (dd, $^3$J=3.7/12.2 Hz, 1H, H6'), 4.04 (ddd, $^3$J=4.7/6.0/10.8 Hz, 1H, H1), 3.96 (ddd, $^3$J=3.8/5.0/8.2 Hz, 1H, H5), 2.47 (t, $^3$J=6.8 Hz, 2H, H8), 2.11 (s, 3H, CH$_3$OAc), 2.10 (s, 3H, CH$_3$OAc), 2.093 (s, 3H, CH$_3$OAc), 2.090 (s, 3H, CH$_3$OAc), 1.92-2.02 (m, 2H, H7). [α]$_D$=+17.2 (c=0.5 g/100 mL, CHCl$_3$, 20° C., 589.3 nm).

HRMS, MALDI: [M+Na$^+$]$_{calc}$=408.1265/[M+Na$^+$]$_{mes}$=408.1272 Da.

Intermediate 2a5: 3-(2,3,4,6-tetra-O-acetyl-α-D-mannopyranosyl) thiopropanamide

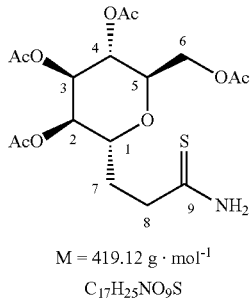

M = 419.12 g · mol⁻¹
C₁₇H₂₅NO₉S

Prepared following GP (3), starting from intermediate 2a4 (307 mg, 0.80 mmol). The resultant oil was purified on silica gel PE/AcOEt 6:4 to 1:1, to afford 155 mg of the desired product as colourless oil in 46% yield.

¹H NMR (400 MHz, CDCl₃): δ (ppm): 7.62 (bs, 1H, NH₂), 7.34 (bs, 1H, NH₂), 5.24 (dd, ³J=3.4/8.4 Hz, 1H, H3), 5.14 (t, 3J=7.8 Hz, 1H, H4), 5.13 (t, 3J=3.7 Hz, 1H, H2), 4.36 (dd, ³J=6.3/12.1 Hz, 1H, H6), 4.11 (dd, ³J=3.0/12.1 Hz, 1H, H6'), 3.99 (ddd, ³J=3.7/3.9/10.9 Hz, 1H, H1), 3.91 (ddd, ³J=3.2/7/10.1 Hz, 1H, H5), 2.63-2.79 (m, 2H, H8), 2.06-2.28 (m, 2H, H7), 2.10 (s, 3H, CH₃OAc), 2.09 (s, 3H, CH₃OAc), 2.06 (s, 3H, CH₃OAc), 2.02 (s, 3H, CH₃OAc). [α]$_D$=+7.8 (c=0.6 g/100 mL, CHCl₃, 20° C., 589.3 nm).

HRMS, MALDI: [M+Na⁺]$_{calc}$=442.1142 Da/[M+Na⁺]$_{mes}$=442.1130 Da.

Intermediate 2a6: 5-acetyl-2-(2-(2,3,4,6-tetra-O-acetyl-α-D-mannopyranosyl) ethyl)thiazole

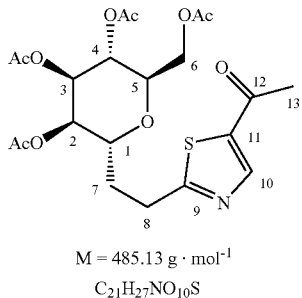 [SMILES: CC(=O)OC[C@H]1O[C@H](CCc2ncc(C(C)=O)s2)[C@@H](OC(C)=O)[C@@H](OC(C)=O)[C@@H]1OC(C)=O ; "C21H27NO10S"]

M = 485.13 g · mol⁻¹
C₂₁H₂₇NO₁₀S

Prepared following GP (6), starting from intermediate 2a5 (50 mg, 0.105 mmol) and chloroacetone. After purification over silica gel (PE/AcOEt 4:6), 21 mg of the desired product was obtained in 41% yield, as a slightly yellow oil.

¹H NMR (400 MHz, CDCl₃): δ (ppm): 8.18 (s, 1H, H10), 5.24 (dd, ³J=3.4/8.4 Hz, 1H, H3) 5.15 (t, ³J=7.7 Hz, 1H, H4), 5.14 (t, ³J=3.7 Hz, 1H, H2), 4.39 (dd, ³J=6.8/12.1 Hz, 1H, H6), 4.06 (dd, ³J=3.3/12.1 Hz, 1H, H6'), 3.99 (m, 1H, H1), 3.92 (ddd, ³J=3.2/7.0/7.0 Hz, 1H, H5), 3.01-3.22 (m, 2H, H8), 2.55 (s, 3H, H13), 2.19-2.32 (m, 1H, H7), 2.03-2.17 (m, 1H, H7'), 2.10 (s, 3H, CH₃OAc), 2.09 (s, 3H, CH₃OAc), 2.07 (s, 3H, CH₃OAc), 2.03 (s, 3H, CH₃OAc).

[α]$_D$=+8.6 (c=1.05 g/100 mL, CHCl₃, 20° C., 589.3 nm).
HRMS, MALDI: [M+Na⁺]$_{calc}$=486.1428 Da/[M+Na⁺]$_{mes}$=486.1441 Da.

Compound 2a: 5-acetyl-2-(2-(α-D-mannopyranosyl) ethyl)thiazole

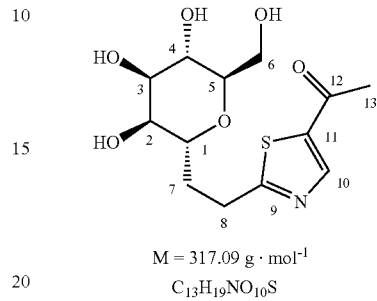

M = 317.09 g · mol⁻¹
C₁₃H₁₉NO₁₀S

Prepared following GP (7), starting from intermediate 2a6 (20 mg, 0.041 mmol). After purification over silica gel (DCM/MeOH 9:1) and lyophilisation, 7.77 mg of the desired product was obtained in 59% yield, as a light white solid.

¹H NMR (400 MHz, MeOD): δ (ppm): 8.36 (s, 1H, H10), 3.87 (ddd, ³J=3.5/6.8/10.8 Hz, 1H, H1), 3.57-3.81 (m, 5H, H2+H3+H4+H6), 3.51 (ddd, ³J=3.1/6.7/10.0 Hz, 1H, H5), 3.11-3.27 (m, 2H, H8), 2.57 (s, 3H, H13), 2.17-2.27 (m, 1H, H7), 1.96-2.06 (m, 1H, H7').

[α]$_D$=+8.6 (c=1.05 g/100 mL, CHCl₃, 20° C., 589.3 nm).
HRMS, MALDI: [M+H⁺]$_{calc}$=318.1006 Da/[M+H⁺]$_{mes}$=318.1005 Da.

Compound 2b (Y=—S—)

Intermediate 2b1: 2,3,4,6-tetra-O-benzyl-1-(prop-1-en-1-yl)-α-D-mannopyranose

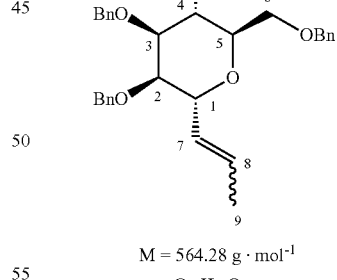

M = 564.28 g · mol⁻¹
C₃₇H₄₀O₅

Intermediate 1a2 (1.162 g, 2.06 mmol, 1 eq) was solubilised in dry benzene (70 mL), and bis(benzonitrile)palladium(II) chloride (78 mg, 0.1 eq) was added. The mixture was refluxed during 48 h, then filtered on celite, and concentrated under vacuum, then purified on silica gel PE/AcOEt 90:10 to afford 1.082 g of the desired product as a colorless oil in 93% yield, as a mixture of E/Z isomers in a E/Z=80:20 ratio. The product also contained <10% of starting material which could not be separated. The obtained product was used as such in the following step.

$^{13}$C NMR (100 MHz, CDCl$_3$): δ (ppm): 138.65 (CBn$_{IV}$), 138.60 (CBn$_{IV}$), 138.56 (CBn$_{IV}$), 138.55 (CBn$_{IV}$), 129.82 (C8 or 7), 127.50-128.7 (CBn), 127.24 (C8 or 7), 76.47, 75.52, 74.66 (CCH2Bn), 74.08, 73.91, 73.52, 72.26 (CCH2Bn), 71.87 (C CH$_2$Bn), 69.75 (C6), 18.22 (C9).

HRMS, MALDI: [M+Na$^+$]$_{calc}$=587.2768 Da/[M+Na$^+$]$_{mes}$=587.2760 Da.

Intermediate 2b2: 2,3,4,6-tetra-O-benzyl-1-(hydroxymethyl)-α-D-mannopyranose

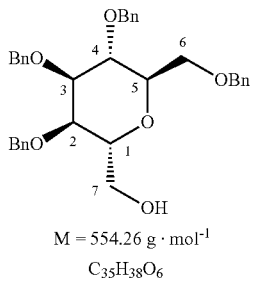 [SMILES: OC[C@H]1O[C@H](COCc2ccccc2)[C@@H](OCc2ccccc2)[C@H](OCc2ccccc2)[C@@H]1OCc1ccccc1 ; "C35H38O6"]

M = 554.26 g·mol$^{-1}$

C$_{35}$H$_{38}$O$_6$

Intermediate 2b1 (1.082 g, 1.91 mmol, 1 eq) was solubilised in DCM/MeOH, 1:1 (100 mL), and the temperature was decreased to −70° C., then ozone was bubbled until the mixture was blue. Ozone was then remove by bubbling nitrogen, and NaBH$_4$ was added (2 eq, 146 mg), then allowed to warm up to rt. After 1 h, the mixture was washed with saturated aqueous NH$_4$Cl, dried over MgSO$_4$, filtered, concentrated under vacuum. The resulting oil was purified on silica gel PE/AcOEt 90:10 to afford 814 mg of the desired product as a colourless oil in 77% yield. The product also contained <10% of the compound carrying 2 carbon in anomeric position, which could not be separated. The obtained product was used as such in the following step.

$^1$H NMR (400 MHz, CDCl$_3$): δ (ppm): 7.26-7.35 (m, 16H, HBn), 7.21-7.24 (m, 4H, HBn), 4.44-4.57 (m, 8H, H$_{CH2Bn}$), 4.07 (ddd, $^3$J=2.8/5.4/7.8 Hz, 1H, H5), 3.96 (ddd, $^3$J=3.4/4.7/7.8 Hz, 1H, H1), 3.83 (dd, $^3$J=7.3/10.3 Hz, 1H, H6), 3.74-3.81 (m, 4H, H7+H2+H3), 3.70 (dd, $^3$J=2.9/4.1 Hz, 1H, H4), 3.65 (dd, $^3$J=5.3/10.2 Hz, 1H, H6').

[α]$_D$=+18.3 (c=1 g/100 mL, CHCl$_3$, 20° C., 589.3 nm).

HRMS, MALDI: [M+Na$^+$]$_{calc}$=577.2561 Da/[M+Na$^+$]$_{mes}$=577.2553 Da.

Intermediate 2b3: (2,3,4,6-tetra-O-benzyl-α-D-mannopyranosyl)-methylmethane-sulfonate

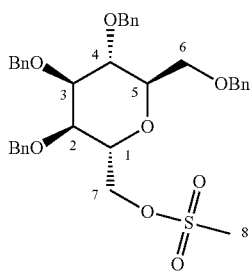

M = 632.24 g·mol$^{-1}$

C$_{36}$H$_{40}$O$_8$S

Prepared following GP (1), starting from intermediate 2b2 (6.04 mmol, 3.350 g). The resultant oil was purified on silica gel PE/AcOEt 90:10 to 75:25, to afford 2.980 g of the desired product as colourless oil in 78% yield.

$^1$H NMR (400 MHz, CDCl$_3$): δ (ppm): 7.26-7.37 (m, 16H, HBn), 7.19-7.24 (m, 4H, HBn), 4.41-4.57 (m, 10H, H$_{CH2Bn}$+H7), 4.05-4.15 (m, 2H, H5+H1), 3.77-3.85 (m, 3H, H6+H2+H3), 3.71 (dd, $^3$J=2.8/4.08 Hz, 1H, H4), 3.65 (dd, $^3$J=5.45/10.3 Hz, 1H, H6'), 2.98 (s, 3H, H8).

[α]$_D$=+29.0 (c=1 g/100 mL, CHCl$_3$, 20° C., 589.3 nm).

HRMS, ESI+: [M+Na$^+$]$_{calc}$=655.23361/[M+Na$^+$]$_{mes}$=655.23265 Da.

Intermediate 2b4: (2,3,4,6-tetra-O-benzyl-1-bromomethyl-α-D-mannopyranose)

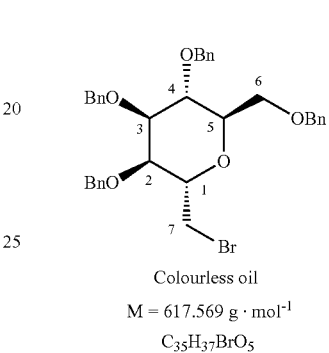

Colourless oil

M = 617.569 g·mol$^{-1}$

C$_{35}$H$_{37}$BrO$_5$

Intermediate 2b3 (4.7 mmol, 2.980 g) was diluted in DMF (70 mL), and TBAB (2 eq, 3.03 g) was added. The mixture was heated at 90° C. overnight, and then concentrated in vacuum. The residue was diluted in Et$_2$O, and washed 5 times by brine, dried over MgSO$_4$, and concentrated under vacuum. The crude product was purified by flash chromatography on silica gel (PE/AcOEt 9:1) to afford 2.33 g of the desired product as colourless oil, in 80% yield.

$^1$H NMR (400 MHz, CDCl$_3$): δ (ppm): 7.19-7.35 (m, 20H, HBn), 4.45-4.57 (m, 8H, H$_{CH2Bn}$), 4.10 (m, 1H, H1), 4.06 (m, 1H, H5), 3.87 (dd, $^3$J=2.2/7.5 Hz, 1H, H2), 3.76-3.82 (m, 3H, H3+H4+H6), 3.72 (dd, $^3$J=5.4/10.2 Hz, 1H, H6'), 3.61 (dd, A part of ABX system, $^{AB}$J=10.8 Hz, $^{BX}$J=4.4 Hz 1H, H7'), 2.53 (dd, A part of ABX system, $^{AB}$J=10.8 Hz, $^{BX}$J=5.7 Hz 1H, H7').

[α]$_D$=+17.6 (c=1 g/100 mL, CHCl$_3$, 20° C., 589.3 nm).

HRMS, MALDI: [M+Na$^+$]$_{calc}$=639.1722 Da/[M+Na$^+$]$_{mes}$=639.1719 Da.

Intermediate 2b5: 5-acetyl-2-((2,3,4,6-tetra-O-acetyl-α-D-mannopyranos-1-yl)methylthioxy)thiazole

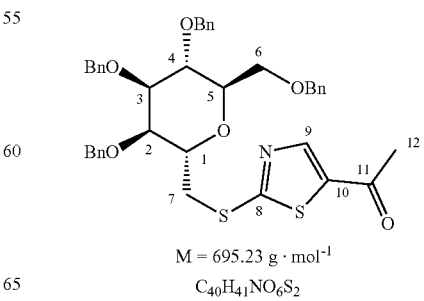

M = 695.23 g·mol$^{-1}$

C$_{40}$H$_{41}$NO$_6$S$_2$

Intermediate 2b3 (150 mg, 0.24 mmol) was placed in DMF (6 mL), and 2-mercapto-5-acetylthiazol (60 mg, 1.5 eq, obtained as described in example 17ter of WO 2014/016361), $K_2CO_3$ (201 mg, 6 eq), and a catalytic amount of KI were added. The mixture was heated to 100° C. during 2 days, then extracted by $Et_2O$, washed with brine 5 times, dried over $MgSO_4$, and concentrated under vacuum.

The residue was purified on silica gel (PE/AcOEt: 6/4) to afford the 140 mg of the desired product as colourless oil in 84% yield.

$^1$H NMR (400 MHz, $CDCl_3$): δ (ppm): 8.02 (s, 1H, H9), 7.20-7.35 (m, 18H, HBn), 4.46-4.60 (m, 8H, $H_{CH2Bn}$), 4.28 (ddd, $^3J$=4.7/7.2/7.2 Hz, 1H, H1), 3.98 (ddd, $^3J$=4.9/4.9/10.4 Hz, 1H, H5), 3.76-3.87 (m, 4H, H6+H3+H2+H4), 3.69 (dd, $^3J$=4.9/10.4 Hz, 1H, H6'), 3.67 (dd, $^3J$=4.9/13.2 Hz, 1H, H7), 3.46 (dd, $^3J$=7.6/13.2 Hz, 1H, H7'), 2.50 (s, 3H, H12).

$[α]_D$=+12.7 (c=0.5 g/100 mL, $CHCl_3$, 20° C., 589.3 nm).
HRMS, MALDI: $[M+Na^+]_{calc}$=718.2267 Da/$[M+Na^+]_{mes}$=718.2258 Da.

Compound 2b: 5-acetyl-2-((α-D-mannopyranos-1-yl)methylthioxy)thiazole

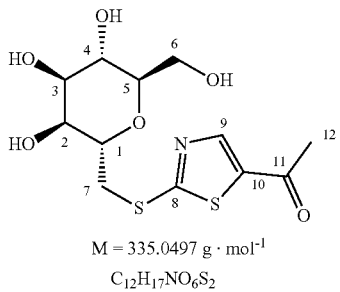 [SMILES: CC(=O)c1cnc(SC[C@H]2O[C@H](CO)[C@@H](O)[C@H](O)[C@@H]2O)s1 ; "C12H17NO6S2"]

M = 335.0497 g · mol$^{-1}$
$C_{12}H_{17}NO_6S_2$

Prepared following GP (9), starting from intermediate 2b5 (64 mg, 0.092 mmol). After purification over silica gel (DCM/MeOH 9:1) and lyophilisation, 14.75 mg of the desired product was obtained in 48% yield, as a light white solid.

$^1$H NMR (400 MHz, MeOD): δ (ppm): 8.31 (s, 1H, H9), 4.28 (m, 1H, H1), 3.90 (t, $^3J$=3.6 Hz, 1H, H2), 3.76-3.83 (m, 2H, H6+H3), 3.70-3.76 (m, 2H, H4+H6'), 3.61-3.70 (m, 2H, H7), 3.53-3.60 (m, 1H, H5), 2.53 (s, 3H, H12).

$[α]_D$=+43.1 (c=0.9 g/100 mL, MeOH, 20° C., 589.3 nm).
HRMS, MALDI: $[M+H^+]_{calc}$=336.0570 Da/$[M+H^+]_{mes}$=336.0568 Da Compound 2c (Y═NH—)

Intermediate 2c1: 2,3,4,6-tetra-O-acetyl-1-azidomethyl-α-D-mannopyranose

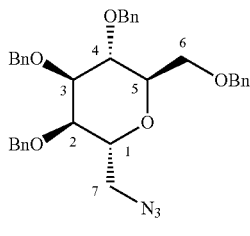

M = 579.2733 g · mol$^{-1}$
$C_{35}H_{37}N_3O_5$

Intermediate 2b3 (900 mg, 1.42 mmol) was placed in DMF (15 mL), and $NaN_3$ (462 mg, 6 eq), and TBAI (1 eq, 523 mg) were added. The mixture was heated to 110° C. during 24 h, then extracted by $Et_2O$, washed with brine 5 times, dried over $MgSO_4$, and concentrated under vacuum.

The residue was purified on silica gel (PE/AcOEt 9:1) to afford the 587 mg of the desired product as colourless oil in 71% yield.

$^1$H NMR (400 MHz, $CDCl_3$): δ (ppm): 7.18-7.36 (m, 20H, HBn), 4.41-4.57 (m, 8H, $H_{CH2Bn}$), 4.10 (ddd, $^3J$=2.6/6.0/6.4 Hz, 1H, H5), 4.06 (ddd, $^3J$=4.5/5.5/8.5 Hz, 1H, H1), 3.82 (dd, A part of ABX system, $J^{AX}$=6.6, $J^{AB}$=10.1 Hz, 1H, H6), 3.76-3.81 (m, 2H, H3+H4), 3.76 (dd, $^3J$=2.8/8.5 Hz, 1H, H2), 3.71 (dd, A part of ABX system, $J^{BX}$=6.0, $J^{AB}$=10. Hz, 1H, H6'), 3.40-3.48 (m, 2H, H7).

$[α]_D$=+27.5 (c=0.5 g/100 mL, $CHCl_3$, 20° C., 589.3 nm).
HRMS, ESI: $[M+H^+]_{calc}$=580.2811 Da/$[M+H^+]_{mes}$=580.2787 Da.

Intermediate 2c2: 2,3,4,6-tetra-O-acetyl-1-aminomethyl-α-D-mannopyranose

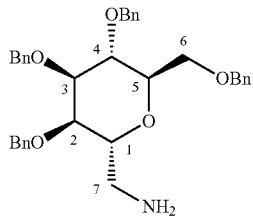

M = 553.2828 g · mol$^{-1}$
$C_{35}H_{33}NO_5$

Intermediate 2c1 (587 mg, 1.01 mmol) was dissolved in THF (15 mL), and few drops of water were added. Triphenylphosphine (345 mg, 1.3 eq) was added and the mixture was heated to reflux for 2 h. The mixture was concentrated in vacuum, rinsed by PE, concentrated and dissolved in $Et_2O$: the triphenylphosphine oxide precipitate and is filtered. The mixture was dried over $MgSO_4$, filtered, concentrated in vacuum.

The residue was purified on silica gel (CHCl3/MeOH 1:0 to 97:3) to afford the 469 mg of the desired product as colourless oil in 84% yield.

$^1$H NMR (400 MHz, $CDCl_3$): δ (ppm): 7.20-7.34 (m, 20H, HBn), 4.47-4.60 (m, 8H, $H_{CH2Bn}$), 3.96 (m, 1H, H), 3.86 (pq, $^3J$=6.07 Hz, 1H, H1), 3.80 (dd, A part of ABX system, $J^{AX}$=6.8, $J^{AB}$=10.2 Hz, 1H, H6), 3.76-3.83 (m, 2H, H3+H4), 3.70 (dd, A part of ABX system, $J^{BX}$=5.0, $J^{AB}$=10.2 Hz, 1H, H6'), 3.65 (dd, $^3J$=2.1/7.0 Hz, 1H, H2), 2.82-2.85 (m, 2H, H7).

$[α]_D$=+20.4 (c=0.5 g/100 mL, $CHCl_3$, 20° C., 589.3 nm).
HRMS, MALDI: $[M+H^+]_{calc}$=554.2901 Da/$[M+H^+]_{mes}$=554.2873 Da.

Intermediate 2c3: N-benzoyl-N'-((2,3,4,6-tetra-O-benzyl-(-D-mannopyranosyl) methyl)-thiourea

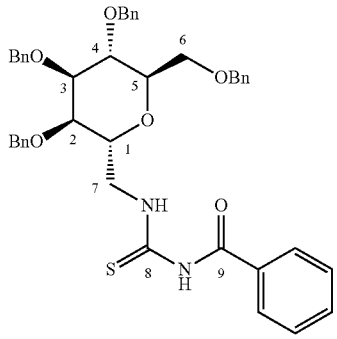

M = 716.2920 g · mol$^{-1}$
C$_{43}$H$_{44}$N$_2$O$_6$S

Potassium isothiocyanate (3 eq, 411 mg), was dissolved in acetone (10 mL), and benzoyl chloride (2 eq, 400 mL) was added the white suspension was stirred 20 min, then intermediate 2c2 (780 mg, 1.41 mmol) was diluted in DCM (5 mL), and added to the mixture. After 10 min, the reaction was complete. The mixture was washed by brine, extracted by DCM, dried over MgSO$_4$ and concentrated under vacuum.

The resulting oil was purified by flash chromatography on silica gel (EP/AcOEt 8:2 to 7:3) to afford 870 mg of the desired product with a 86% yield, as a colourless oil.

$^1$H NMR (400 MHz, CD$_2$Cl$_2$): δ (ppm): 10.95 (1H, bt, $^3$J$_{NH-7}$=10.0 Hz, NH), 8.94 (1H, s, NH), 7.77-7.82 (2H, m, H-Bz), 7.57-7.64 (1H, m, H-Bz), 7.46-7.54 (2H, m, H-Bz), 7.20-7.36 (20H, m, H-Bn), 4.48-4.67 (8H, m, H—CH$_2$Bn), 4.19-4.26 (1H, m), 4.04-4.15 (2H, m), 3.77-3.91 (3H, m), 3.70-3.77 (1H, m), HRMS, MALDI: [MNa$^+$]$_{calc}$ 739.2812=, [MNa$^+$]$_{mes}$=739.2783.

Intermediate 2c4: N-((2,3,4,6-tetra-O-benzyl-α-D-mannopyranosyl) methyl)-thiourea

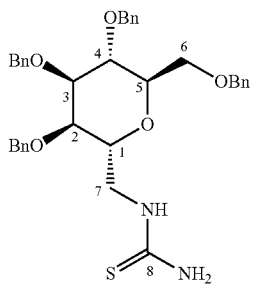

M = 612.2657 g · mol$^{-1}$
C$_{36}$H$_{40}$N$_2$O$_5$S

Intermediate 2c3 (870 mg, 1.21 mmol) was diluted in MeOH (6 mL), sodium hydroxide pellets were added. After 10 min, the reaction was complete. The mixture was filtered, then neutralised by 2M HCl, extracted with DCM, washed with brine, dried over MgSO$_4$ and concentrated under vacuum.

The resulting oil was purified by flash chromatography on silica gel (EP/AcOEt 1:1) to afford 698 mg of the desired product with a 94% yield, as colourless oil.

NMR spectra couldn't be obtained with accuracy, due to the signal of the thiourea substituent (in particular because of the NH and NH$_2$ groups) which blurred a significant part of the spectra.

MS, MALDI m/z: [m+H$^+$]=613.3.
HRMS, MALDI: [MH$^+$]$_{calc}$ 613.2731=, [MH$^+$]$_{mes}$=613.2706.

Intermediate 2c5: 5-acetyl-2-(((2,3,4,6-tetra-O-benzyl-α-D-mannopyranosyl) methyl)amino)-thiazole

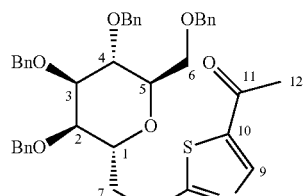

M = 678.2763 g · mol$^{-1}$
C$_{40}$H$_{42}$N$_2$O$_6$S

Prepared following GP (6), starting from intermediate 2c4 (166 mg, 0.271 mmol) and chloroacetone. After a first purification over silica gel (PE/AcOEt 3:6) and a second purification (CHCl$_3$/AcOEt 7:3), 152 mg of the desired product was obtained in 83% yield, as a light yellow oil.

$^1$H NMR (400 MHz, CDCl$_3$): δ (ppm): 7.76 (1H, s, H-9), 7.16-7.37 (20H, m, H-Bn), 6.05 (1H, bt, NH), 4.36-4.55 (8H, m, H—CH$_2$Bn), 4.03-4.10 (2H, m, H-1, H-5), 3.79-3.86 (2H, m, H-4, H-6), 3.67-3.72 (2H, m, H-2, H-3), 3.61 (1H, dd, $^2$J$_{6}$-6'=10.3 Hz, $^3$J$_{6'-5}$=5.6 Hz, H-6'), 3.43-3.61 (2H, m, H-7), 2.43 (3H, s, H-12).

[α]$_D$=+13.8 (c=0.5 g/100 mL, CHCl$_3$, 20° C., 589.3 nm).
HRMS, MALDI: [MH$^+$]$_{calc}$ 679.2836=, [MH$^+$]$_{mes}$=679.2836.

Compound 2c: 5-acetyl-2-((((-D-mannopyranosyl) methyl)amino)-thiazole

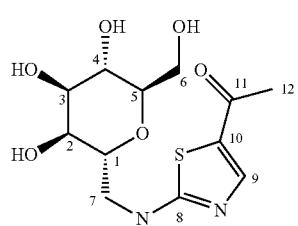

M = 318.0885 g · mol$^{-1}$
C$_{12}$H$_{18}$N$_2$O$_6$S

Prepared following GP (9), starting from intermediate 2c5 (152 mg, 0.224 mmol). After purification over silica gel (DCM/MeOH 9:1) and lyophilisation, 52.15 mg of the desired product was obtained in 73% yield, as a light white solid.

¹H NMR (400 MHz, D₂O): δ (ppm): 8.15 (1H, s, H-9), 4.27 (1H, m, H-1), 4.06 (1H, t, ³J=3.2 Hz, H-2), 3.84-3.93 (4H, m, H-3, H-6, H7'), 3.79 (1H, t, ³J=8.3 Hz, H-4), 3.67-3.74 (2H, m, H-5, H-7'), 4.03-4.10 (2H, m, H-1, H-5), 3.79-3.86 (2H, m, H-4, H-6), 3.67-3.72 (2H, m, H-2, H-3), 3.61 (1H, dd, ²J₆-6=10.3 Hz, ³J₆-5=5.6 Hz, H-6'), 3.43-3.61 (2H, m, H-7), 2.43 (3H, s, H-12)

[α]$_D$=+43.8 (c=1.75 g/100 mL, H2O, 20° C., 589.3 nm).
HRMS, MALDI: [MH⁺]$_{calc}$ 319.0958=, [MH⁺]$_{mes}$=319.0949.

Compound 2d (Y=—NH—)

Intermediate 2d1: 5-(4-methyl-2-(pyrazin-2-yl) thiazol-5-ylcarbonyl)-2-(((2,3,4,6-tetra-O-benzyl-α-D-mannopyranosyl) methyl)amino)-thiazole

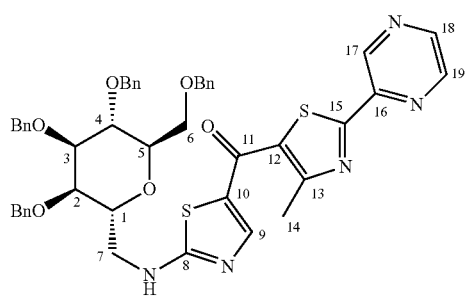

M = 839.2811 g · mol⁻¹
C₄₇H₄₅N₅O₆S₂

Prepared following GP (6), starting from Intermediate 2c4 (300 mg, 0.49 mmol) and 2-Bromo-1-[4-methyl-2-(2-pyrazinyl)-1,3-thiazol-5-yl]-1-ethanone. After purification over silica gel (PE/AcOEt 4:6) 249 mg of the desired product was obtained in 60% yield, as yellow oil.

¹H NMR (400 MHz, CDCl₃): δ (ppm): 9.46 (1H, d, ³J₁₉-₁₈=0.5 Hz, H-19), 8.64 (1H, d, ³J₁₇-₁₈=2.5 Hz, H-17), 8.58 (1H, dd, ³J₁₇-₁₈=2.5 Hz, ³J₁₉-₁₈=1.5 Hz, H-18), 7.96 (1H, s, H-9), 7.17-7.37 (20H, m, H-Bn), 6.24 (1H, bt, NH), 4.36-4.56 (8H, m, H—CH₂Bn), 4.05-4.13 (2H, m, H-1, H-5), 3.81-3.87 (2H, m, H-4, H-6), 3.68-3.73 (2H, m, H-2, H-3), 3.61 (1H, dd, ²J₆-₆'=10.2 Hz, ³J₆'-₅=5.6 Hz, H-6'), 3.47-3.63 (2H, m, H-7), 2.75 (3H, s, H-14).

[α]$_D$=+2.1 (c=0.5 g/100 mL, CHCl₃, 20° C., 589.3 nm).
HRMS, MALDI: [MH⁺]$_{calc}$=840.2884, [MH⁺]$_{mes}$=840.2857.

Compound 2d: 5-(4-methyl-2-(pyrazin-2-yl)thiazol-5-ylcarbonyl)-2-(((α-D-mannopyranosyl) methyl) amino)-thiazole

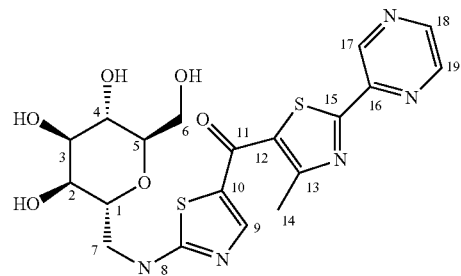

M = 479.5299 g · mol⁻¹
C₁₉H₂₁N₅O₆S₂

Prepared following GP (9), starting from intermediate 2d1 (239 mg, 0.284 mmol). After purification over silica gel (DCM/MeOH 8:2) and lyophilisation, 130 mg of the desired product was obtained in 95% yield, as a yellow powder.

¹H NMR (400 MHz, DMSO): δ (ppm): 9.36 (1H, d, ³J₁₉-₁₈=1.4 Hz, H-19), 8.94 (1H, bs, NH) 8.82 (1H, d, ³J₁₇-₁₈=2.5 Hz, H-17), 8.77 (1H, dd, ³J₁₇-₁₈=2.5 Hz, ³J₁₉-₁₈=1.4 Hz, H-18), 8.01 (1H, s, H-9), 4.83 (1H, d, ²J=5.0 Hz, OH), 4.79 (1H, d, ²J=4.3 Hz, OH), 4.70 (1H, d, ²J=5.4 Hz, OH), 4.41 (1H, dd, ²J=5.1 Hz, ²J=6.5 Hz, OH), 3.86 (1H, m, H-1), 3.57-3.71 (4H, m, H-3, H-4, H-6, H-7), 3.42-3.57 (4H, m, H-2, H-5H-6', H-7'), 2.62 (3H, s, H14).

[α]$_D$=+28.8 (c=0.5 g/100 mL, DMSO, 20° C., 589.3 nm).
HRMS, ESI: [MNa⁺]$_{calc}$=502.0831, [MNa⁺]$_{mes}$=502.0841.

Compound 2e (Y=—NH—)

Intermediate 2e1: 1-(1-Dimethylamino-ethylidene)-2-methyl-isothiourea

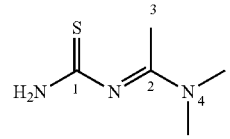

M = 145.0673 g · mol⁻¹
C₅H₁₁N₃S

Thiourea (500 mg, 6.58 mmol) was suspended in DCM (8 mL), and DMA-DMA, (1.25 mL, 1.3 eq) was added. The mixture was heated to reflux, then filtered on silica pad (DCM/AcOEt 1:1). The solid was then washed by Et₂O, to provide 830 mg of white solid in a 87% yield.

¹H NMR (300 MHz, DMSO): δ (ppm): 8.11 (1H, bs, NH), 7.69 (1H, bs, NH), 2.93 (6H, s, H-4), 2.17 (3H, s, H3), (matching literature data (*Journal of Heterocyclic Chemistry*, 38(1), 93-98; 2001)).

MS, ESI m/z: [m+H⁺]=146.2.

Intermediate 2e2: 2-amino-4-methyl-5-acétylthiazol

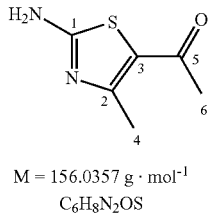

M = 156.0357 g · mol$^{-1}$
C$_6$H$_8$N$_2$OS

Intermediate 2e1 (200 mg, 1.38 mmol) was solubilised in DCM (5 mL), and chloroacetone (229 mL, 2 eq) was added, followed by Et$_3$N (375 mL, 2 eq). The mixture was stirred at rt overnight, then filtered and rinsed with DCM to provide 140 mg of the desired product In a 65% yield.

$^1$H NMR (300 MHz, DMSO): δ (ppm): 7.88 (2H, s, NH), 2.39 (3H, s, H-4), 2.31 (3H, s, H-6) (matching literature data (*Journal of Medicinal Chemistry*, 47(7), 1662-1675; 2004)).

HRMS, ESI: [MH$^+$]$_{calc}$=157.0430, [MH$^+$]$_{mes}$=157.0428.

Intermediate 2e3: 2-bromo-4-methyl-5-acétylthiazol

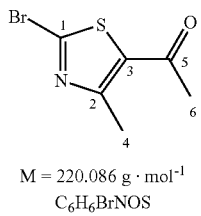

M = 220.086 g · mol$^{-1}$
C$_6$H$_6$BrNOS

Intermediate 2e2 (200 mg, 1.26 mmol) was suspended in ACN (15 mL), copper bromide (286 mg, 1 eq), and isoamyl nitrite (511 mL, 3 eq) were added. The mixture was heated to reflux 3 h, then diluted by DCM, washed by brine, then by a solution of EDTA, dried over MgSO$_4$, and concentrated under vacuum.

After purification over silica gel (DCM) 263 mg of the desired product was obtained in 94% yield, as yellow oil.

$^1$H NMR (75 MHz, CDCl$_3$): δ (ppm): 2.71 (3H, s, H-4), 2.51 (3H, s, H-6), (matching literature data (PCT Int. Appl., 2010128163).

HRMS, ESI: [MNa$^+$]$_{calc}$=219.94262, [MNa$^+$]$_{mes}$=219.24264.

Intermediate 2e4: 2-bromo-4-methyl-5-bromoacétylthiazol

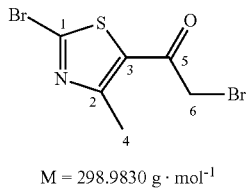

M = 298.9830 g · mol$^{-1}$
C$_6$H$_5$Br$_2$NOS

Intermediate 2e3 (100 mg, 0.45 mmol) was solubilised in dioxane (7 mL), and copper bromide was added. The mixture was heated overnight at 110° C., diluted with DCM, washed with brine, then with a solution of EDTA, dried over MgSO$_4$, and concentrated under vacuum.

After purification over silica gel (EP/AcOEt 1:1) 90 mg of the desired product was obtained in 66% yield, as a yellow oil.

$^1$H NMR (300 MHz, CDCl$_3$): δ (ppm): 4.18 (2H, s, H-6), 2.75 (3H, s, H-4).

HRMS, ESI: [MNa$^+$]$_{calc}$=297.85314, [MNa$^+$]$_{mes}$=297.85223.

Intermediate 2e5

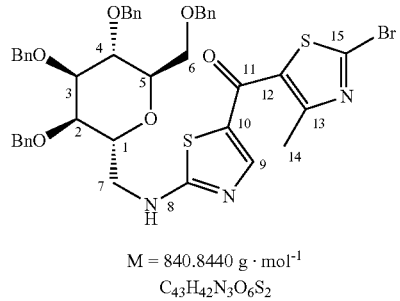 [SMILES: Cc1nc(Br)sc1C(=O)c1cnc(NC[C@H]2O[C@H](COCc3ccccc3)[C@@H](OCc3ccccc3)[C@H](OCc3ccccc3)[C@@H]2OCc2ccccc2)s1]

M = 840.8440 g · mol$^{-1}$
C$_{43}$H$_{42}$N$_3$O$_6$S$_2$

Prepared following GP (6), starting from intermediate 2c4 (200 mg, 0.326 mmol) and intermediate 2e4, and DIPEA was used instead of triethylamine. After purification over silica gel (PE/AcOEt 1:1) 220 mg of the desired product was obtained in 80.5% yield, as a yellow oil.

$^1$H NMR (400 MHz, CDCl$_3$): δ (ppm): 7.82 (1H, s, H-9), 7.17-7.37 (20H, m, H-Bn), 6.30 (1H, bs, NH), 4.35-4.55 (8H, m, H—CH$_2$Bn), 4.05-4.11 (2H, m, H-1, H-5), 3.82-3.86 (2H, m, H-4, H-6), 3.68-3.71 (2H, m, H-2, H-3), 3.57-3.64 (2H, m, H-6', H-7), 3.46-3.53 (1H, m, H-7'), 2.64 (3H, s, H-14) [α]$_D$=+1.0 (c=0.5 g/100 mL, CHCl$_3$, 20° C., 589.3 nm).

HRMS, ESI: [MH$^+$]$_{calc}$=840.17712, [MH$^+$]$_{mes}$=840.17780.

Intermediate 2e6: 5-(4-methyl-2-((trimethylsilyl)ethynyl) thiazol-5-ylcarbonyl)-2-(((2,3,4,6-tetra-O-benzyl-α-D-mannopyranosyl) methyl)amino)-thiazole

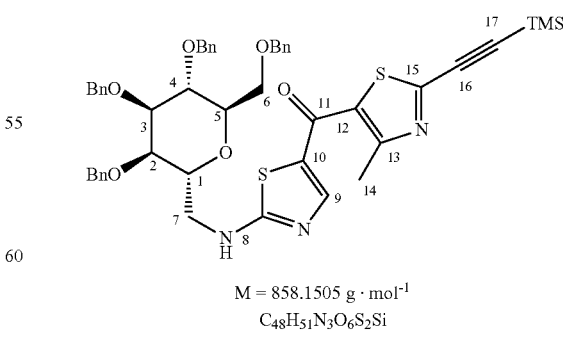

M = 858.1505 g · mol$^{-1}$
C$_{48}$H$_{51}$N$_3$O$_6$S$_2$Si

Intermediate 2e5 (1.236 g, 1.47 mmol) was solubilised in THF, and triethylamine (0.6 mL, 3 eq) was added. The mixture was sonicated under nitrogen bubbling during 15 min, then (Trimethylsilyl)acetylene (1.24 mL, 6 eq) was added, followed by Bis(triphenylphosphine)palladium(II) chloride (52 mg, 0.05 eq), and copper(I) iodide (14 mg, 0.05 eq). The mixture was stirred at rt during 3 h, then diluted by AcOEt, washed by brine, dried over MgSO4, and concentrated under vacuum.

After purification over silica gel (PE/AcOEt 7:3) 769 mg of the desired product was obtained in 61% yield, as a yellow oil.

$^1$H NMR (400 MHz, CDCl$_3$): δ (ppm): 7.83 (1H, s, H-9), 7.17-7.36 (20H, m, H-Bn), 6.19 (1H, bt, NH), 4.35-4.55 (8H, m, H—CH$_2$Bn), 4.04-4.11 (2H, m, H-1, H-5), 3.81-3.86 (2H, m, H-4, H-6), 3.67-3.72 (2H, m, H-2, H-3), 3.57-3.63 (2H, m, H-6', H-7), 3.47-3.54 (1H, m, H-7'), 2.66 (3H, s, H-14), 0.29 (9H, s, H-TMS).

$[α]_D$=+1.9 (c=0.5 g/100 mL, CHCl$_3$, 20° C., 589.3 nm).
HRMS, ESI: [MH$^+$]$_{calc}$=858.3067, [MH$^+$]$_{mes}$=858.3104.

Intermediate 2e7: 5-(4-methyl-2-(ethynyl) thiazol-5-ylcarbonyl)-2-(((2,3,4,6-tetra-O-benzyl-α-D-mannopyranosyl) methyl)amino)-thiazole

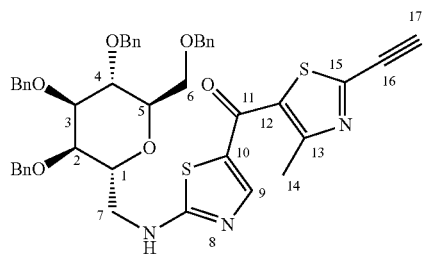

M = 785.2593 g · mol$^{-1}$
C$_{45}$H$_{43}$N$_3$O$_6$S$_2$

Intermediate 2e6 (650 mg, 0.76 mmol) was solubilised in MeOH, and potassium carbonate (210 mg, 2 eq) was added. The suspension was stirred 30 min at rt, then extracted with DCM, washed with a saturated solution of NH$_4$Cl, then brine, dried over MgSO$_4$, and concentrated under vacuum.

After purification over silica gel (DCM/AcOEt 7:3) 500 mg of the desired product was obtained in 87% yield, as a yellow oil.

$^1$H NMR (400 MHz, CDCl$_3$): δ (ppm): 7.84 (1H, s, H-9), 7.16-7.38 (20H, m, H-Bn), 6.23 (1H, bt, NH), 4.33-4.55 (8H, m, H—CH$_2$Bn), 4.03-4.12 (2H, m, H-1, H-5), 3.80-3.88 (2H, m, H-4, H-6), 3.66-3.72 (2H, m, H-2, H-3), 3.57-3.65 (2H, m, H-6', H-7), 3.55 (1H, s, H-17) 3.46-3.55 (1H, m, H-7'), 2.67 (3H, s, H-14).

$[α]_D$=+2.1 (c=0.5 g/100 mL, CHCl$_3$, 20° C., 589.3 nm).
HRMS, ESI: [MH$^+$]$_{calc}$=786.2672, [MH$^+$]$_{mes}$=786.2682.

Intermediate 2e8: 5-(4-methyl-2-(1-1H-1,2,3-triazol-4-yl) thiazol-5-ylcarbonyl)-2-(((2,3,4,6-tetra-O-benzyl-α-D-mannopyranosyl) methyl)amino)-thiazole

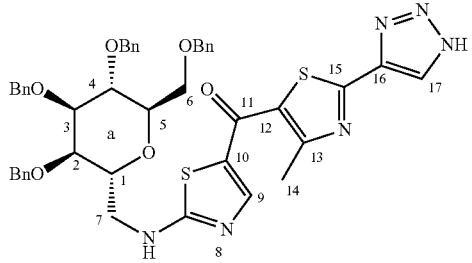

M = 828.9974 g · mol$^{-1}$
C$_{45}$H$_{44}$N$_6$O$_6$S$_2$

Intermediate 2e7 was solubilised in a mixture of DMF and methanol (9:1, 2 mL) and placed in a tube, trimethylsilylazide (72 mL, 6 eq) and copper(I)iodide (2 mg, 0.1 eq) were added, the tube was sealed, and heated to 90° C. for 5 h. After completion, the mixture was diluted with Et$_2$O, washed with brine, dried over MgSO$_4$, and concentrated under vacuum. After purification over silica gel (CHCl$_3$/AcOEt 6:4 to 3:7) 36 mg of the desired product was obtained in 49% yield, as a yellow oil.

$^1$H NMR (400 MHz, CDCl$_3$): δ (ppm): 8.24 (1H, s, H-9), 8.05 (1H, s, H-17), 7.14-7.40 (20H, m, H-Bn), 4.38-4.58 (8H, m, H—CH$_2$Bn), 4.07-4.17 (2H, m, H-1, H-5), 3.81-3.93 (2H, m, H-4, H-6), 3.69-3.77 (2H, m, H-2, H-3), 3.50-3.69 (3H, m, H-6', H-7), 2.75 (3H, s, H-14).

$[α]_D$=+4.3 (c=0.93 g/100 mL, CHCl$_3$, 20° C., 589.3 nm).
HRMS, ESI: [MH$^+$]$_{calc}$=829.2842, [MH$^+$]$_{mes}$=829.2952.

Compound 2e

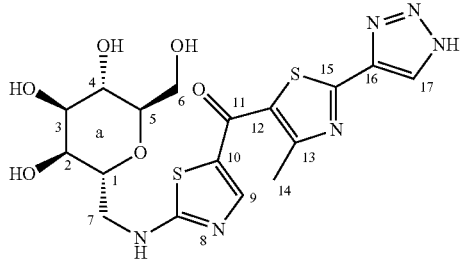

M = 468.0885 g · mol$^{-1}$
C$_{17}$H$_{20}$N$_6$O$_6$S$_2$

Prepared following GP (9), starting from Tc6-116-1 (36 mg, 0.043 mmol) after precipitation in acetonitrile, and purification over C-18 chromatography, 6 mg of the desired product was obtained in 30% yield $^1$H NMR (500 MHz, MeOD): δ (ppm): 8.45 (1H, s, H-9), 8.20 (1H, s, H-17), 4.04-4.12 (2H, m, H-1, H-6), 3.84-3.88 (1H, m), 3.73-3.83 (5H, m, H-5), 3.65 (1H, dd, 2J$_{7-7'}$=11.9 Hz, $^3$J$_{7-1}$=3.0 Hz, H-6'), 2.70 (3H, s, H-14)

$[α]_D$=+50 (c=0.25 g/100 mL, MeOH, 20° C., 589.3 nm)
HRMS, ESI: [M+Na$^+$]$_{calc}$=491.0783, [M+Na$^+$]$_{mes}$=491.0792

Compound 2f (Y=—NH—)

Intermediate 2f1

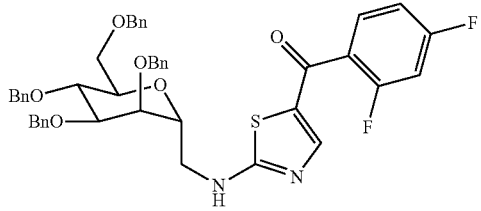 [SMILES: O=C(c1cnc(NCC2OC(COCc3ccccc3)C(OCc3ccccc3)C(OCc3ccccc3)C2OCc2ccccc2)s1)c1ccc(F)cc1F]

According to the general procedure A, using the thiourea 2c4 (50 mg, 0.082 mmol) and 2'-chloro-2,4-difluoroacetophenone (20 mg, 0.106 mmol) as starting materials, the derivative 2f1 (39 mg, 0.050 mmol, 61%) was obtained after purification by silica gel column chromatography (petroleum ether/EtOAc, 80:20 as eluents) as a yellowish oil.

$^1$H NMR (400 MHz, CDCl$_3$) δ 3.45 (1H, dd, $J_{7a,7b}$=12.8 Hz, $J_{7a,1}$=6.1 Hz, H-7a), 3.54-3.60 (2H, m, H-7b, H-6a), 3.64-3.68 (2H, m, H-2, H-3), 3.75-3.81 (2H, m, H-4, H-6b), 3.99-4.07 (2H, m, H-1, H-5), 4.30-4.49 (8H, m, 4×BnO), 6.44-6.56 (2H, m, difluoroacetophenone), 7.13-7.33 (21H, m, 4×BnO, difluoroacetophenone), 7.53 (1H, s, H9).

$[α]_D$=+12.8 (c=0.9 in CHCl$_3$)

m/z [M+H]$^+$ 777; HRMS (ESI) m/z calcd for C$_{45}$H$_{42}$F$_2$N$_2$O$_6$SNa [M+Na]$^+$ 776,2732, found 776,2729.

Compound 2f

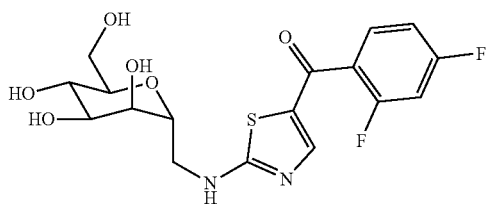

Chemical Formula: C$_{17}$H$_{18}$F$_2$N$_2$O$_6$S
Exact Mass: 416.0854
Molecular Weight: 416.3958

According to the general procedure C, using the derivative 2f1 (40 mg, 0.0515 mmol) as starting materials, the derivative 2f (16 mg, 0.0385 mmol, 75%) was obtained after purification by silica gel column chromatography (AcOEt/MeOH, 70:30 as eluent) as an amorphous white solid.

$^1$H NMR (400 MHz, MeOD) δ 3.62-3.77 (6H, m), 3.81 (1H, dd, J=4.9 Hz, J=3.1 Hz), 3.89 (1H, dd, J=11.9 Hz, J=7.1 Hz, H-6b), 4.06 (1H, m, H-1), 6.55-7.65 (3H, m, difluoroacetophenone), 7.54 (1H, s, thiazol).

$[α]_D$=+42 (c=1.4 in MeOD).

m/z [M+H]$^+$ 417; HRMS (ESI) m/z calcd for C$_{17}$H$_{19}$F$_2$N$_2$O$_6$S [M+H]$^+$ 417.0938, found 417.0926.

Compound 2g (Y=—NH—)

Intermediate 2 g1

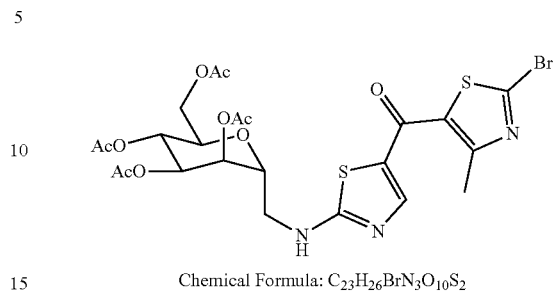

Chemical Formula: C$_{23}$H$_{26}$BrN$_3$O$_{10}$S$_2$
Exact Mass: 647.0243
Molecular Weight: 648.4960

According to the general procedure A, using the thiourea 2k1 (30 mg, 0.0714 mmol) and 1-(2-bromo-4-methylthiazol-5-yl)-2-chloroethan-1-one (25 mg, 0.0928 mmol) as starting materials, the derivative 2 g1 (39 mg, 0.0615 mmol, 86%) was obtained after purification by silica gel column chromatography (petroleum ether/EtOAc, 30:70 as eluents) as a yellowish oil.

$[α]_D$=+63 (c=0.8 in CHCl$_3$); $^1$H NMR (400 MHz, CDCl$_3$) 52.07 (3H, s, AcO), 2.09 (3H, s, AcO), 2.10 (3H, s, AcO), 2.12 (3H, s, AcO), 2.62 (3H, methylthiazol), 3.60 (2H, m, H-7), 3.97 (1H, dd, $J_{6a,6b}$=12.1 Hz, $J_{6a,5}$=3.5 Hz, H-6a), 4.05 (1H, m, H-5), 4.27 (1H, m, H-1), 4.77 (1H, dd, $J_{6b,6a}$=12.1 Hz, $J_{6a,5}$=8.3 Hz, H-6b), 4.98 (1H, dd, $J_{4,3}$=5.5 Hz, $J_{4,5}$=3.6 Hz, H-4), 5.11 (1H, dd, $J_{2,1}$=7.9 Hz, $J_{2,3}$=3.3 Hz, H-2), 5.32 (1H, dd, $J_{3,4}$=5.3 Hz, $J_{3,2}$=3.3 Hz, H-3), 6.61 (1H, bs, NH), 7.80 (1H, s, thiazol); $^{13}$C NMR (127 MHz, CDCl$_3$) 518.4 (CH$_3$, methylthiazol), 20.69, 20.75, 20.77, 20.81 (4CH$_3$, 4×AcO), 34.7 (CH$_2$, C-7), 60.7 (CH$_2$, C-6), 67.0, 67.4, 67.9, 68.9 (4CH), 73.4 (CH, C-1), 116.6 (C), 130.5 (C), 146.0 (CH, thiazol), 158.4 (C), 169.26, 169.49, 169.64, 169.75 (4C, 4×AcO), 171.0, 173.9, 176.0 (3C). m/z [M+H]$^+$ 649; HRMS (ESI) m/z calcd for C$_{23}$H$_{27}$BrN$_3$O$_{10}$S$_2$[M+H]$^+$ 648.0321, found 648.0329.

Compound 2g

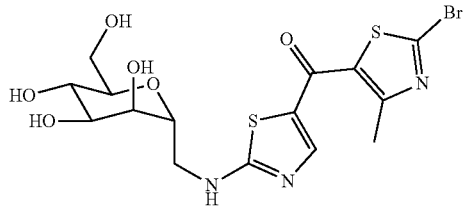

Chemical Formula: C$_{15}$H$_{18}$BrN$_3$O$_6$S$_2$
Exact Mass: 478.9820
Molecular Weight: 480.3480

According to the general procedure B, using the derivative 2 g1 (25 mg, 0.039 mmol) as starting material, the derivative 2 g was obtained after lyophilization (17 mg, 0.036 mmol, 94%) as an amorphous white solid.

$^1$H NMR (400 MHz, MeOD) δ 2.56 (3H, s, methylthiazol), 3.64-3.83 (6H, m), 3.81 (1H, dd, $J_{2,3}$=5.2 Hz, $J_{2,1}$=3.2 Hz, H-2), 3.90 (1H, dd, $J_{6a,6b}$=11.8 Hz, $J_{6a,5}$=6.9 Hz, H-6a), 4.06 (1H, dt, J=8.0 Hz, J=4.8 Hz, H-1), 7.89 (1H, s, thiazol).

[α]$_D$=+42 (c=1.1 in MeOD).

m/z [M+H]$^+$ 479; HRMS (ESI) m/z calcd for C$_{15}$H$_{19}$BrN$_3$O$_6$S$_2$ [M+H]$^+$ 479.9893, found 479.9880.

Compound 2h (Y=—NH—)

Intermediate 2 h1

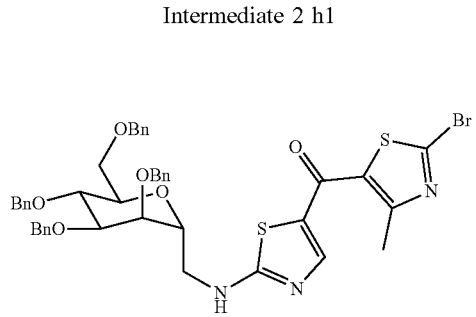

Chemical Formula: C$_{43}$H$_{42}$BrN$_3$O$_6$S$_2$
Exact Mass: 839.1698
Molecular Weight: 840.8480

According to the general procedure A, using the thiourea 2c4 (50 mg, 0.082 mmol) and 1-(2-bromo-4-methylthiazol-5-yl)-2-chloroethan-1-one (31 mg, 0.123 mmol) as starting materials, the derivative 2 h1 (48 mg, 0.057 mmol, 70%) was obtained after purification by silica gel column chromatography (petroleum ether/EtOAc, 70:30 as eluents) as a yellowish oil.

$^1$H NMR (400 MHz, CDCl$_3$) δ 2.64 (3H, s, methylthiazol), 3.49 (1H, dd, J$_{7a,7b}$=12.7 Hz, J$_{7a,1}$=6.2 Hz, H-7a), 3.57-3.65 (2H, m, H-7b, H-6a), 3.67-3.71 (2H, m, H-2, H-3), 3.81-3.87 (2H, m, H-4, H-6b), 4.04-4.13 (2H, m, H-1, H-5), 4.34-4.56 (8H, m, 4×BnO), 6.26 (1H, bs, NH), 7.17-7.36 (20H, m, 4×BnO), 7.82 (1H, s, H9).

[α]$_D$=+18 (c=1.3 in CHCl$_3$).

m/z [M+H]$^+$ 840; HRMS (ESI) m/z calcd for C$_{43}$H$_{43}$BrN$_3$O$_6$S$_2$ [M+H]$^+$ 840.1774, found 840.1771.

Compound 2h

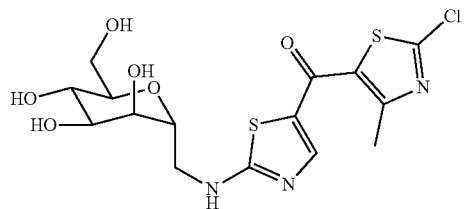

Chemical Formula: C$_{15}$H$_{18}$ClN$_3$O$_6$S$_2$
Exact Mass: 435.0326
Molecular Weight: 435.8940

According to the general procedure C, using the derivative 2 h1 (30 mg, 0.036 mmol) as starting materials, the derivative 2 h (14 mg, 0.032 mmol, 89%) was obtained after purification by silica gel column chromatography (DCM/MeOH, 85:15 as eluent) as an amorphous white solid.

[α]$_D$=+21 (c=1.1 in MeOD).

$^1$H NMR (400 MHz, MeOD) δ 2.53 (3H, s, methylthiazol), 3.62-3.78 (6H, m), 3.82 (1H, dd, J$_{2,3}$=4.9 Hz, J$_{2,1}$=3.2 Hz, H-2), 3.89 (1H, dd, J$_{6b,6a}$=11.9 Hz, J$_{6b,5}$=6.8 Hz, H-6b), 4.07 (1H, m, H-1), 7.89 (1H, s, thiazol).

m/z [M+H]$^+$ 436; HRMS (ESI) m/z calcd for C$_{15}$H$_{19}$ClN$_3$O$_6$S$_2$ [M+H]$^+$ 436.0396, found 436.0398.

Compound 2i (Y=—NH—)

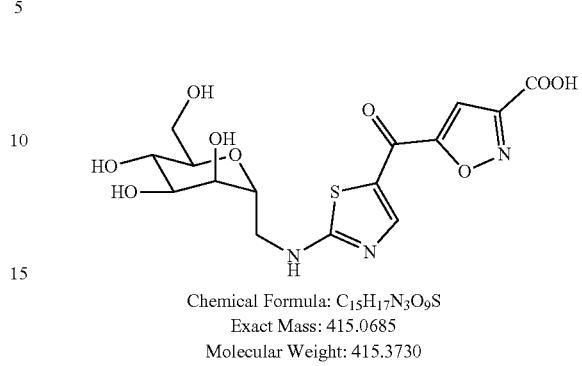

Chemical Formula: C$_{15}$H$_{17}$N$_3$O$_9$S
Exact Mass: 415.0685
Molecular Weight: 415.3730

To a solution of 2j (33 mg, 0.0745 mmol, prepared as explained below) in a mixture 3:1 of MeOH/H$_2$O (2 mL) was added LiOH (3.6 mg, 0.149 mmol). The mixture was stirred at 50° C. for 8 h, neutralized with Amberlite IR120 (H), filtered and the solvents evaporated to dryness. The substrate was dissolved in water and subjected to lyophilization to give 2i (28 mg, 0.0675 mmol, 91%) as an amorphous white solid.

$^1$H NMR (400 MHz, MeOD) δ3.67 (1H, dd, J$_{6a,6}$b=11.6 Hz, J$_{6a,5}$=2.5 Hz, H-6a), 3.71-3.87 (6H, m), 4.03 (1H, dd, J$_{6b,6a}$=11.6 Hz, J$_{6b,5}$=7.8 Hz, H-6b), 4.08 (1H, m, H-1), 7.52 (1H, s, isoxazole), 8.49 (1H, s, thiazol).

[α]$_D$=+19 (c=0.6 in H$_2$O);

m/z [M+H]$^+$ 416; HRMS (ESI) m/z calcd for C$_{15}$H$_{18}$N$_3$O$_9$S [M+H]$^+$ 416.0754, found 416.0758.

Compound 2j (Y=—NH—)

Intermediate 2j1

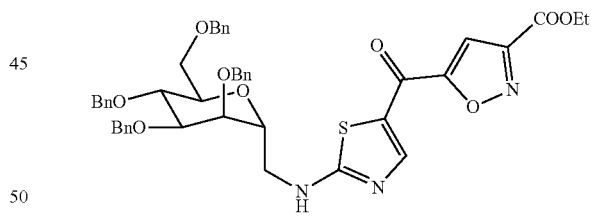

According to the general procedure A, using the thiourea 2c4 (50 mg, 0.082 mmol) and ethyl 5-(2-bromoacetyl)isoxazole-3-carboxylate as starting materials, the derivative 2j1 (47 mg, 0.058 mmol, 71%) was obtained after purification by silica gel column chromatography (petroleum ether/EtOAc, 70:30→50:50 as eluents) as a yellowish oil.

$^1$H NMR (400 MHz, CDCl$_3$) δ 1.36 (3H, t, J=7.13 Hz, COOEt), 3.45 (1H, dd, J$_{7a,7b}$=13.4 Hz, J$_{7a,1}$=6.3 Hz, H-7a), 3.51-3.59 (2H, m, H-7b, H-6a), 3.61-3.65 (2H, m, H-2, H-3), 3.75-3.81 (2H, m, H-4, H-6b), 3.99-4.09 (2H, m, H-1, H-5), 4.27-4.49 (10H, m, COOEt, 4×BnO), 7.00 (1H, bs, NH), 7.11-7.29 (21H, m, isoxazole, 4×BnO), 8.41 (1H, s, H9).

[α]$_D$=+62.6 (c=0.8 in CHCl$_3$).

m/z [M+H]$^+$ 826; HRMS (ESI) m/z calcd for C$_{45}$H$_{45}$N$_3$O$_9$SNa [M+Na]$^+$ 826.2770, found 826.2774.

Compound 2j

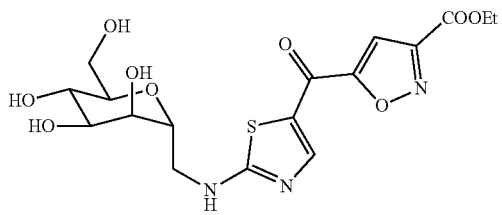

Chemical Formula: $C_{17}H_{21}N_3O_9S$
Exact Mass: 443.0998
Molecular Weight: 443.4270

According to the general procedure C, using the derivative 2j1 (40 mg, 0.049 mmol) as starting materials, the derivative 2j (14 mg, 0.032 mmol, 64%) was obtained after purification by silica gel column chromatography (DCM/MeOH, 80:20 as eluents) as an amorphous white solid.

$^1$H NMR (400 MHz, D$_2$O) δ 1.47 (3H, t, J=7.2 Hz, COOEt), 3.68 (1H, dd, $J_{7a,7b}$=14.2 Hz, $J_{7a,1}$=4.0 Hz, H-7a), 3.73 (1H, m, H-5), 3.81 (1H, t, J=8.6 Hz, H-4), 3.83 (1H, dd, $J_{6a,6b}$=14.6 Hz, $J_{6a,5}$=4.7 Hz, H-6a), 3.88-3.93 (3H, m, H-3, H-6b, H-7b), 4.08 (1H, t, J=3.0 Hz, H-2), 4.26 (1H, ddd, $J_{1,7b}$=9.8 Hz, $J_{1,7a}$=4.1 Hz, $J_{1,2}$=2.9 Hz, H-1), 4.53 (2H, q, J=7.2 Hz, COOEt), 7.43 (1H, s, isoxazole), 8.32 (1H, s, thiazol).

$[α]_D$=+13 (c=0.8 in H$_2$O).

m/z [M+Na]+466; HRMS (ESI) m/z calcd for $C_{17}H_{21}N_3O_9SNa$ [M+Na]$^+$ 466.0895, found 466.0895.

Compound 2k (Y=—NH—)

Thiourea 2k1

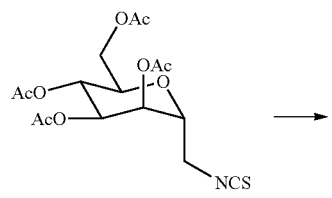

2k1

To a solution of starting isocyanate 1 (50 mg, 0.124 mmol, obtained as described by Barghash et al) in DMF (0.6 mL), at 0° C. and under N$_2$, was added HMDS (258 □L, 1.240 mmol). After 8 h, the mixture was concentrated and the crude was purified by silica gel column chromatography (EtOAc as eluent) to give the thiourea 2k1 (41 mg, 0.098 mmol, 79%) as a colorless oil.

1H NMR (400 MHz, CDCl3) δ 1.94 (3H, s, AcO), 1.97 (3H, s, AcO), 1.99 (6H, s, 2×AcO), 3.74 (2H, m, H-7), 3.89-4.15 (2H, m, H-1, H-5, H-6a), 4.36 (1H, m, H-6b), 4.97-5.11 (2H, m, H-4, H-2), 5.15 (1H, dd, J3,4=7.5 Hz, J3,2=3.3 Hz, H-3), 6.42 (2H, bs, NH2), 7.37 (1H, bs, NH).

$[α]D$=+12 (c=0.9 in CHCl3).

m/z [M+H]+ 421; HRMS (ESI) m/z calcd for C16H25N2O9S [M+H]+ 421.1273, found 421.1275.

Intermediate 2k2

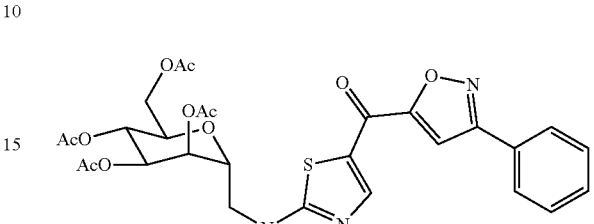

Chemical Formula: $C_{28}H_{29}N_3O_{11}S$
Exact Mass: 615.1523
Molecular Weight: 615.6100

According to the general procedure A, using the thiourea 2k1 (30 mg, 0.0714 mmol) and 2-bromo-1-(3-phenylisoxazol-5-yl)ethan-1-one (25 mg, 0.0928 mmol) as starting materials, the derivative 2k2 (35 mg, 0.0568 mmol, 80%) was obtained after purification by silica gel column chromatography (petroleum ether/EtOAc, 30:70 as eluents) as a yellowish oil.

$^1$H NMR (400 MHz, CDCl$_3$) δ 2.08 (6H, s, 2×AcO), 2.1 (6H, s, 2×AcO), 3.63 (2H, m, H-7), 3.99 (1H, dd, $J_{6a,6b}$=12.3 Hz, $J_{6a,5}$=3.8 Hz, H-6a), 4.11 (1H, ddd, $J_{5,6}$=8.4 Hz, $J_{5,6}$=3.5 Hz, $J_{5,4}$=3.5 Hz, H-5), 4.31 (1H, m, H-1), 4.79 (1H, dd, $J_{6b,6a}$=12.0 Hz, $J_{6a,5}$=8.5 Hz, H-6b), 5.00 (1H, dd, $J_{4,3}$=5.3 Hz, $J_{4,5}$=3.5 Hz, H-4), 5.13 (1H, dd, $J_{2,1}$=8.0 Hz, $J_{2,3}$=3.2 Hz, H-2), 5.34 (1H, dd, $J_{3,4}$=5.3 Hz, $J_{3,2}$=3.3 Hz, H-3), 7.30 (1H, s, phenylisoxazol), 7.48 (3H, m, phenylisoxazol), 7.85 (2H, m, phenylisoxazol), 8.54 (1H, s, thiazol).

$[α]_D$=+58 (c=0.7 in CHCl$_3$)

m/z [M+H]$^+$ 616; HRMS (ESI) m/z calcd for $C_{28}H_{30}N_3O_{11}S$ [M+H]$^+$ 616.1595, found 616.1596.

Compound 2k

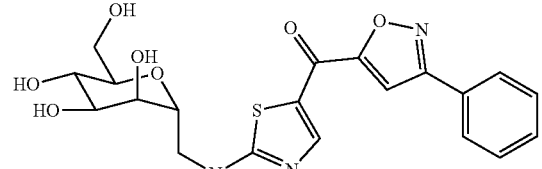

Chemical Formula: $C_{20}H_{21}N_3O_7S$
Exact Mass: 447.1100
Molecular Weight: 447.4620

According to the general procedure B, using 2k2 (20 mg, 0.0325 mmol) as starting materials, the derivative 2k (14 mg, 0.0313 mmol, 96%) was obtained after lyophilization.

$^1$H NMR (400 MHz, DMSO) δ 3.45-3.57 (4H, m), 3.59-3.76 (4H, m), 3.89 (1H, m, H-1), 7.56 (3H, m, phenylisoxazol), 7.89 (1H, s, phenylisoxazol), 8.01 (2H, m, phenylisoxazol), 8.43 (1H, s, thiazol).

[α]$_D$=+12 (c=0.5 in MeOH).

m/z [M+H]$^+$ 448; HRMS (ESI) m/z calcd for C$_{20}$H$_{22}$N$_3$O$_7$S [M+H]$^+$ 448.1173, found 448.1173.

Compound 2l (Y=—NH—)

Intermediate 2l1

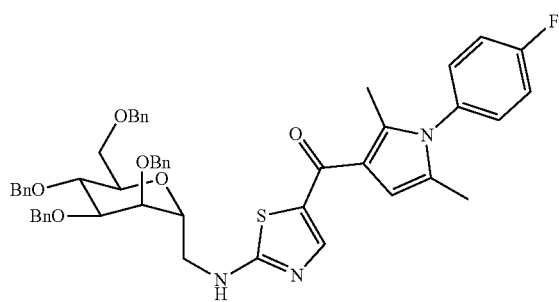 [SMILES: Cc1cc(C(=O)c2cnc(NCC3OC(COCc4ccccc4)C(OCc4ccccc4)C(OCc4ccccc4)C3OCc3ccccc3)s2)c(C)n1-c1ccc(F)cc1]

According to the general procedure A, using the thiourea 2c4 (50 mg, 0.082 mmol) and 2-chloro-1-[1-(4-fluorophenyl)-2,5-dimethyl-1H-pyrrol-3-yl]ethanone (33 mg, 0.123 mmol) as starting materials, the derivative 2l1 (38 mg, 0.045 mmol, 54%) was obtained after purification by silica gel column chromatography (petroleum ether/EtOAc, 80:20 as eluents) as a yellowish oil.

$^1$H NMR (400 MHz, CDCl$_3$) δ 1.95 (3H, s, methylpyrrol), 2.22 (3H, s, methylpyrrol), 3.46 (1H, dd, J$_{7a,7b}$=13.1 Hz, J$_{7a,1}$=6.7 Hz, H-7a), 3.52-3.61 (2H, m, H-7b, H-6a), 3.66-3.69 (2H, m, H-2, H-3), 3.75-3.81 (2H, m, H-4, H-6b), 3.99-4.09 (2H, m, H-1, H-5), 4.35-4.49 (8H, m, 4×BnO), 6.32 (1H, bs, methylpyrrol), 7.12-7.31 (24H, m, 4×BnO, fluorophenyl), 7.81 (1H, s, H9).

[α]$_D$=+31 (c=1.3 in CHCl$_3$).

m/z [M+H]$^+$ 852; HRMS (ESI) m/z calcd for C$_{51}$H$_{51}$FN$_3$O$_6$S [M+H]$^+$ 852.3506, found 852.3483.

Compound 2l

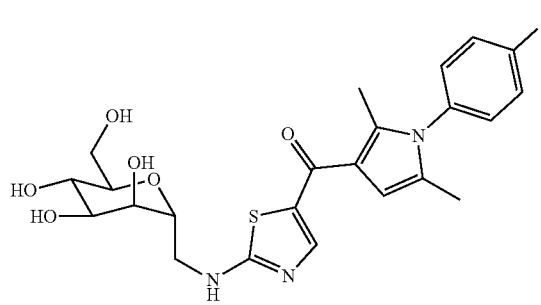

Chemical Formula: C$_{23}$H$_{26}$FN$_3$O$_6$S
Exact Mass: 491.1526
Molecular Weight: 491.5344

According to the general procedure C, using the derivative 2l1 (31 mg, 0.0364 mmol) as starting materials, the derivative 2l (17 mg, 0.0345 mmol, 95%) was obtained after purification by silica gel column chromatography (DCM/MeOH, 80:20 as eluent) as an amorphous white solid.

$^1$H NMR (400 MHz, MeOD) δ2.01 (3H, s, methylpyrrol), 2.20 (3H, s, methylpyrrol), 3.61-3.79 (7H, m), 3.85 (1H, dd, J$_{2,3}$=4.8 Hz, J$_{2,1}$=3.3 Hz, H-2), 3.89 (1H, dd, J$_{6b,6a}$=11.9 Hz, J$_{6b,5}$=6.9 Hz, H-6b), 4.09 (1H, ddd, J=10.2 Hz, J=5.1 Hz, J=5.1 Hz, H-1), 6.39 (1H, bs, pyrrol), 7.29-7.32 (4H, m, fluorophenyl), 7.82 (1H, s, H9).

[α]$_D$=+19 (c=0.3 in MeOH).

m/z [M+H]$^+$ 492; HRMS (ESI) m/z calcd for C$_{23}$H$_{27}$FN$_3$O$_6$S [M+H]$^+$ 492.1597, found 492.1599.

Compound 2m (Y=—NH—)

Intermediate 2m1

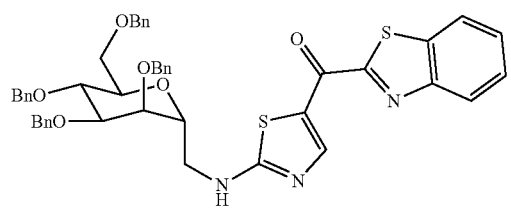

Chemical Formula: C$_{46}$H$_{43}$N$_3$O$_6$S$_2$
Exact Mass: 797.26
Molecular Weight: 797.98

According to the general procedure A, using the thiourea 2c4 (75 mg, 0.122 mmol) and 1-(1,3-benzothiazol-2-yl)-2-bromo-1-ethanone (34 mg, 0.134 mmol) as starting materials, the derivative 2 m1 (61 mg, 0.076 mmol, 63%) was obtained after purification by silica gel column chromatography (petroleum ether/EtOAc, 80:20 as eluents) as a yellowish oil.

$^1$H NMR (400 MHz, CDCl$_3$) δ 3.60 (1H, dd, J$_{7a,7b}$=13.1 Hz, J$_{7a,1}$=6.6 Hz, H-7a), 3.66-3.72 (2H, m, H-7b, H-6a), 3.76-3.79 (2H, m, H-2, H-3), 3.86-3.94 (2H, m, H-4, H-6b), 4.11-4.21 (2H, m, H-1, H-5), 4.41-4.56 (8H, m, 4×BnO), 7.22-7.39 (24H, m, 4×BnO), 7.54 (2H, m, benzothiazol), 7.99 (1H, m, benzothiazol), 8.22 (2H, m, benzothiazol), 9.04 (1H, s, H9).

[α]$_D$=+18 (c=0.9 in CHCl$_3$)

m/z [M+H]$^+$ 798; HRMS (ESI) m/z calcd for C$_{46}$H$_{44}$N$_3$O$_6$S$_2$[M+H]$^+$ 798.2686, found 798.2672.

Compound 2m

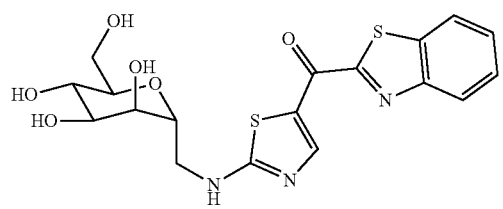

Chemical Formula: C$_{18}$H$_{19}$N$_3$O$_6$S$_2$
Exact Mass: 437.07
Molecular Weight: 437.49

According to the general procedure C, using the derivative 2 m1 (30 mg, 0.0376 mmol) as starting materials, the derivative 2m (15 mg, 0.0343 mmol, 91%) was obtained after purification by silica gel column chromatography (AcOEt/MeOH, 70:30 as eluent) as an amorphous white solid.

¹H NMR (400 MHz, DMSO-d6) δ3.47-3.70 (8H, m), 3.91 (1H, ddd, J=8.7 Hz, J=4.9 Hz, J=4.9 Hz, H-1), 4.50 (1H, bs, OH), 4.76 (1H, bs, OH), 4.89 (2H, bs, OH), 7.64 (2H, m, benzothiazol), 8.25 (2H, bd, J=7.9 Hz, benzothiazol), 8.89 (1H, s, thiazol), 9.34 (1H, bs, NH).

$[\alpha]_D$=+51.3 (c=0.2 in MeOH);

m/z [M+H]⁺ 438; HRMS (ESI) m/z calcd for $C_{18}H_{20}N_3O_6S_2$[M+H]⁺ 438.0788, found 438.0790.

Compound 2n (Y=—NH—)

Intermediate 2n1: 2-chloro-1-(4-methyl-2-(prop-2-yn-1-ylamino)thiazol-5-yl)ethan-1-one

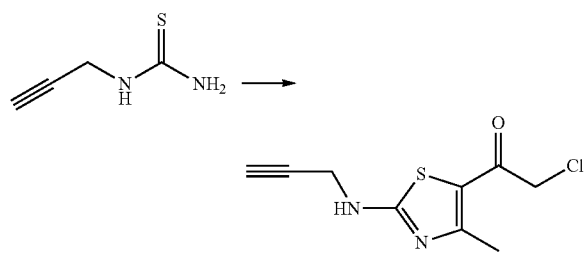

According to the general procedure A, using 1-(prop-2-yn-1-yl)thiourea (189 mg, 1.658 mmol) and dichloroacetone as starting materials, the derivative 2n1 (270 mg, 1.179 mmol, 71%) was obtained after purification by silica gel column chromatography (petroleum ether/EtOAc, 50:50 as eluents) as a yellowish amorphous solid.

¹H NMR (400 MHz, CDCl₃) δ 2.36 (1H, t, J=2.5 Hz), 2.62 (3H, s), 4.15 (2H, d, J=2.5 Hz), 4.35 (2H, s).

m/z [M+H]⁺ 229; HRMS (ESI) m/z calcd for $C_9H_{10}N_2OSCl$ [M+H]⁺ 229.0196, found 229.0197.

Intermediate 2n2

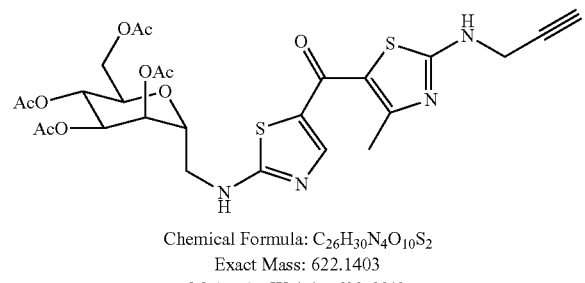

Chemical Formula: $C_{26}H_{30}N_4O_{10}S_2$
Exact Mass: 622.1403
Molecular Weight: 622.6640

According to the general procedure A, using the thiourea 2k1 (200 mg, 0.476 mmol) and 2n1 (142 mg, 0.619 mmol) as starting materials, the derivative 2n2 (249 mg, 0.399 mmol, 84%) was obtained after purification by silica gel column chromatography (EtOAc as eluents) as a yellowish amorphous solid.

¹H NMR (400 MHz, CDCl₃) δ 2.06 (3H, s, AcO), 2.03 (3H, s, AcO), 2.099 (3H, s, AcO), 2.104 (3H, s, AcO), 2.34 (1H, t, J=2.5 Hz, propargylamine), 2.56 (3H, s, thiazol), 3.57 (2H, m, H-7), 4.02 (1H, dd, $J_{6a,6b}$=12.0 Hz, $J_{6a,5}$=3.7 Hz, H-6a), 4.07-4.14 (3H, m, propargylamine, H-5), 4.25 (1H, m, H-1), 4.69 (1H, dd, $J_{6b,6a}$=12.0 Hz, $J_{6b,5}$=8.2 Hz, H-6b), 4.99 (1H, dd, $J_{2,3}$=5.5 Hz, $J_{2,1}$=3.8 Hz, H-2), 5.12 (1H, dd, $J_{4,5}$=7.6 Hz, $J_{4,3}$=3.4 Hz, H-4), 5.32 (1H, dd, $J_{3,2}$=5.5 Hz, $J_{3,4}$=3.3 Hz, H-3), 6.92 (1H, bs, NH), 7.23 (1H, bs, NH), 7.85 (1H, m, thiazol).

$[\alpha]_D$=+61 (c=1.4 in CHCl₃);

m/z [M+H]⁺ 623; HRMS (ESI) m/z calcd for $C_{26}H_{31}N_4O_{10}S_2$[M+H]⁺ 623.1484, found 623.1476.

Compound 2n

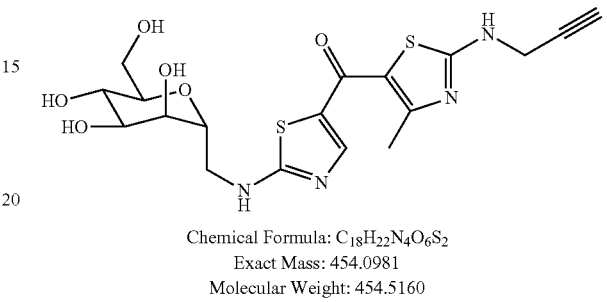

Chemical Formula: $C_{18}H_{22}N_4O_6S_2$
Exact Mass: 454.0981
Molecular Weight: 454.5160

According to the general procedure B, using 2n2 (29 mg, 0.046 mmol) as starting materials, the derivative 2n (20 mg, 0.044 mmol, 96%) was obtained after lyophilization.

¹H NMR (400 MHz, MeOD) δ2.49 (3H, s, methylthiazol), 2.69 (1H, t, J=2.5 Hz, propargylamine), 3.59-3.79 (8H, m), 3.83 (1H, dd, $J_{2,3}$=4.7 Hz, $J_{2,1}$=3.4 Hz, H-2), 3.88 (1H, dd, $J_{6b,6a}$=11.8 Hz, $J_{6b,5}$=7.1 Hz, H-6b), 4.06 (1H, dt, J=7.8 Hz, 4.9, H-1), 4.16 (1H, d, J=2.5 Hz, propargylamine), 7.85 (1H, s, thiazol).

$[\alpha]_D$=+37 (c=1.3 in MeOD).

m/z [M+H]⁺ 455; HRMS (ESI) m/z calcd for $C_{18}H_{22}N_4O_6S_2$[M+H]⁺ 455.1063, found 455.1054.

Compound 2o (Y=—NH—)

Intermediate 2o1

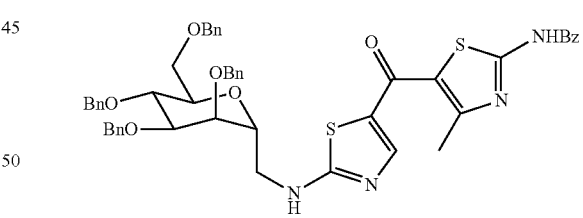

Chemical Formula: $C_{50}H_{48}N_4O_7S_2$
Exact Mass: 880.2964
Molecular Weight: 881.0750

According to the general procedure A, using the thiourea 2c4 (50 mg, 0.082 mmol) and N-(5-(2-chloroacetyl)-4-methylthiazol-2-yl)benzamide (36 mg, 0.123 mmol) as starting materials, the derivative 2o1 (54 mg, 0.061 mmol, 75%) was obtained after purification by silica gel column chromatography (petroleum ether/EtOAc, 50:50 as eluents) as a yellowish oil.

¹H NMR (400 MHz, CDCl₃) δ 2.47 (3H, s, methylthiazol), 3.52 (1H, dd, $J_{7a,7b}$=12.9 Hz, $J_{7a,1}$=6.6 Hz, H-7a), 3.62-3.68 (2H, m, H-7b, H-6a), 3.71-3.76 (2H, m, H-2, H-3), 3.82-3.89 (2H, m, H-4, H-6b), 4.09-4.17 (2H, m, H-1, H-5), 4.41-4.57 (8H, m, 4×BnO), 6.94 (1H, bs, NH), 7.21-7.38 (20H, m, 4×BnO), 7.54 (2H, bt, J=7.5 Hz, benzamide), 7.63 (1H, bt, J=7.5 Hz, benzamide), 7.94 (1H, s, H9), 7.98 (1H, bd, J=7.5 Hz, benzamide).

$[\alpha]_D$=+48 (c=1.2 in CHCl$_3$);

m/z [M+H]$^+$ 881; HRMS (ESI) m/z calcd for C$_{50}$H$_{48}$N$_4$O$_7$S$_2$[M+H]$^+$ 881.3027, found 881.3043.

Compound 2o

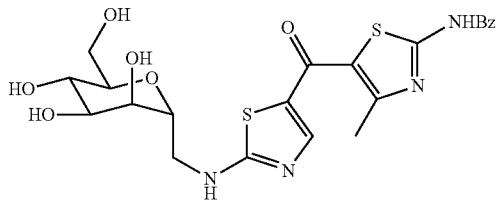

Chemical Formula: C$_{22}$H$_{24}$N$_4$O$_7$S$_2$
Exact Mass: 520.11
Molecular Weight: 520.58

According to the general procedure C, using the derivative 2o1 (37 mg, 0.042 mmol) as starting materials, the derivative 2o (20 mg, 0.038 mmol, 91%) was obtained after purification by silica gel column chromatography (DCM/MeOH, 80:20 as eluents) as an amorphous white solid.

$^1$H NMR (400 MHz, DMSO) δ 2.52 (3H, s, methylthiazol), 3.34-3.70 (H, m), 3.87 (1H, m, H-1), 7.55 (2H, bt, J=7.5 Hz, benzamide), 7.66 (1H, bt, J=7.5 Hz, benzamide), 7.93 (1H, s, thiazol), 8.11 (1H, bd, J=7.5 Hz, benzamide), 8.94 (1H, bs, NH), 13.0 (1H, bs, NH).

$[\alpha]_D$=+32 (c=0.6 in MeOH).

m/z [M+H]$^+$ 521; HRMS (ESI) m/z calcd for C$_{22}$H$_{25}$N$_4$O$_7$S$_2$[M+H]$^+$ 521.1166, found 521.1159.

Example 3: Compounds of Formula (II) (Divalent Compounds)

Compound 3a (Y=—NH—)

Intermediate 3a1: 5-(4-methyl-2-(1-((2,3,4,6-tetra-O-benzyl-α-D-mannopyranosyl)methyl)-1H-1,2,3-triazol-4-yl) thiazol-5-ylcarbonyl)-2-(((2,3,4,6-tetra-O-benzyl-α-D-mannopyranosyl) methyl)amino)-thiazole

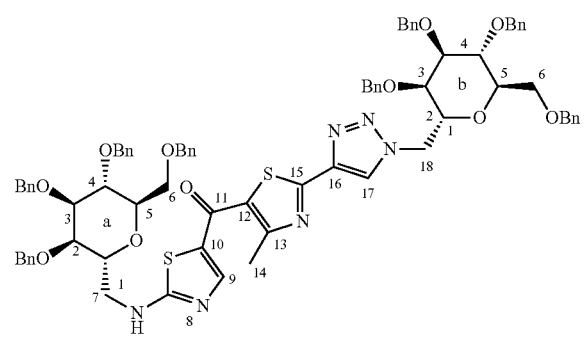

M = 1365.6548 g · mol$^{-1}$
C$_{80}$H$_{80}$N$_6$O$_{11}$S$_2$

Prepared following GP (10), starting from intermediate 2e7 (75 mg, 0.095 mmol) and intermediate 2c1 (66 mg, 1.2 eq). After purification over silica gel (CHCl$_3$/AcOEt 8:2), 45 mg of the desired product was obtained in 35% yield, as a yellow oil.

$^1$H NMR (500 MHz, CDCl$_3$): δ (ppm): 8.45 (1H, s, H-9), 7.97 (1H, bs, H-17), 7.10-7.39 (40H, m, H-Bn), 6.16 (1H, bs, NH), 4.74 (1H, dd, $^2J_{18-18'}$=14.2 Hz, $^3J_{1b-18}$=2.5 Hz, H-18), 4.61 (1H, dd, $^2J_{18-18'}$=14.2 Hz, $^3J_{1b-18'}$=6.6 Hz, H-18'), 4.34-4.56 (16H, m, H—CH$_2$Bn), 4.26 (1H, ddd, $^2J_{1b-18}$=2.4 Hz, $^3J_{1b-18'}$=6.6 Hz, $^3J_{1b-2b}$=9.1 Hz, H-1 b), 4.16 (1H, m, H-5b), 4.09 (2H, m, H-1a, H-5a), 3.82-3.87 (3H, m, H-3a, H-3b, H-6a), 3.80 (1H, dd, $^2J_{6b-6b'}$=10.6 Hz, $^3J_{6b-5b}$=8.2 Hz, H-6b), 3.69-3.73 (2H, m, H-2a, H-4a) 3.66 (1H, m, H-4b), 3.65-3.65 (3H, m, H-6a', H-6b', H-7), 3.48-3.55 (2H, m, H-2b, H-7'), 2.69 (3H, s, H-14).

$[\alpha]_D$=+2.3 (c=0.62 g/100 mL, CHCl$_3$, 20° C., 589.3 nm).

HRMS, ESI: [MH$^+$]$_{calc}$=1365.5405, [MH$^+$]$_{mes}$=1365.5367.

Compound 3a: 5-(4-methyl-2-(1-(((α-D-mannopyranosyl)methyl)-1H-1,2,3-triazol-4-yl) thiazol-5-ylcarbonyl)-2-(((α-D-mannopyranosyl) methyl)amino)-thiazole Prepared following GP (9), starting from intermediate 3a1 (45 mg, 0.033 mmol) after precipitation in methanol, and purification over C-18 chromatography, 15 mg of the desired product was obtained in 70% yield.

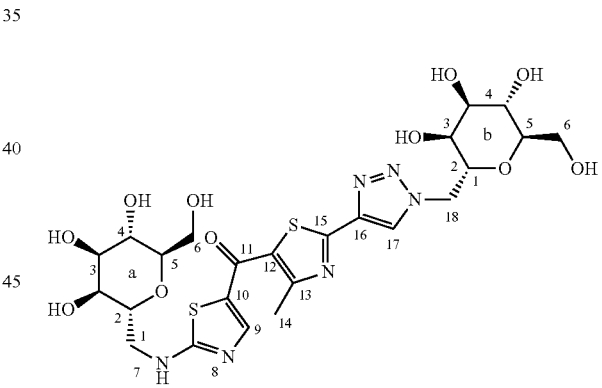

Yellow solid (hygroscopic)
M = 644.1570 g · mol$^{-1}$
C$_{24}$H$_{32}$N$_6$O$_{11}$S$_2$ $^1$H NMR (500 MHz, D$_2$O): δ (ppm): 8.54 (1H, s, H-17), 7.83 (1H, s, H-9), 4.99 (1H, dd, $^2J_{18-18'}$=15.0 Hz, $^3J_{18-1b}$=10.8 Hz, H-18), 4.79 (1H, m, H18'), 4.45 (1H, dt, $^3J_{1b-2b}$=3.2 Hz, $^3J_{1b-18}$=10.2 H-1b), 4.21 (1H, ddd, $^3$J=2.6 Hz, $^3$J=4.0, $^3$J=9.4, H-1a), 4.14 (1H, t, $^3$J=3.2 Hz, H-2b), 4.05 (1H, t, $^3$J=2.9 Hz, H-2a), 3.97 (1H, dd, $^3J_{1b-2b}$=3.4 Hz, $^3J_{1b-18}$=8.2, H-3b), 3.82-3.92 (8H, m, H-3a, H-4a, H-4b, H-6a, H-6b, H-5b), 3.79 (1H, t, $^3$J=8.8 Hz, H-4a), 3.74 (1H, dd, $^2J_{7-7'}$=14.4 Hz, $^3J_{7-1a}$=4.6 Hz, H-7), 3.70 (1H, m, H-5a), 3.59 (1H, dd, $^2J_{7-7'}$=14.4 Hz, $^3J_{7-1a}$=4.2 Hz, H-7'), 2.51 (3H, S, H-14)

HRMS, ESI: [MH$^+$]$_{calc}$=645.1649, [MH$^+$]$_{mes}$=645.1662

Compound 3b (Y=—NH—)

Intermediate 3b1: 5-(4-methyl-2-(1-((1-O-methyl-2,3,4-tetra-O-benzyl-α-D-mannopyranos-6-yl)methyl)-1H-1,2,3-triazol-4-yl)thiazol-5-ylcarbonyl)-2-(((2,3,4,6-tetra-O-benzyl-α-D-mannopyranosyl)methyl)amino)-thiazole Prepared following GP (10), starting from 2e7 (100 mg, 0.127 mmol) and methyl 6-azido-6-deoxy-2,3,4-tris-O-(phenylmethyl)-α-D-Mannopyranoside (Liu et al, 2012) (62 mg, 1.1 eq). After purification over silica gel (EP/AcOEt 7:3 to 5:5) 89 mg of the desired product was obtained in 55% yield, as yellow oil.

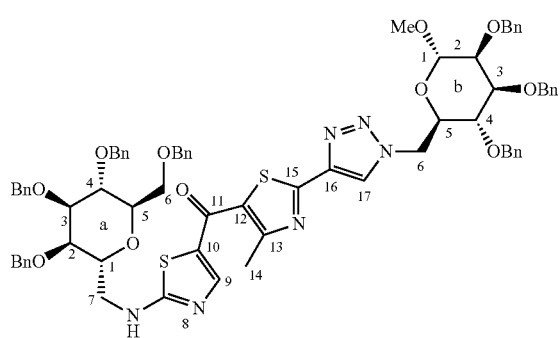

$C_{73}H_{74}N_6O_{11}S_2$
Yellow oil
M = 1274.4857 g · mol⁻¹

$^1$H NMR (500 MHz, CDCl$_3$): δ (ppm): 8.36 (1H, s, H-17), 7.96 (1H, bs, H-9), 7.17-7.40 (35H, m, H-Bn), 4.95 (1H, d, $^3$J=10.9 Hz, H-6b), 4.36-4.74 (16H, m, H-1 b, H-6b', H—CH$_2$Bn), 4.09 (2H, m, H-1a, H-5a), 3.90-3.97 (2H, m, H-3b, H-4b), 3.81-3.86 (2H, m, H-4a, H-6a), 3.76 (1H, dd, $^3$J$_{3b-2b}$=2.6, $^3$J$_{1b-2b}$=1.9 Hz, H-2b), 3.69-3.73 (2H, m, H-2a, H-3a), 3.58-3.66 (3H, m, H-6a, H-5b H-7), 3.51 (1H, dd, $^3$J$_{7'-1a}$=6.2, $^2$J$_{7-7'}$=12.2 Hz, H-7'), 3.15 (3H, s, OMe), 2.71 (3H, s, H-14)

[α]$_D$=+12.1 (c=0.5 g/100 mL, CHCl$_3$, 20° C., 589.3 nm)

HRMS, MALDI: [MH$^+$]$_{calc}$=1275.4930, [MH$^+$]$_{mes}$=1275.4889

Compound 3b

Prepared following GP (9), starting from intermediate 3b1 after precipitation in methanol, and purification over C-18 chromatography. Obtained as a mixture of two anomers of carbohydrate b (α/β-1:1)

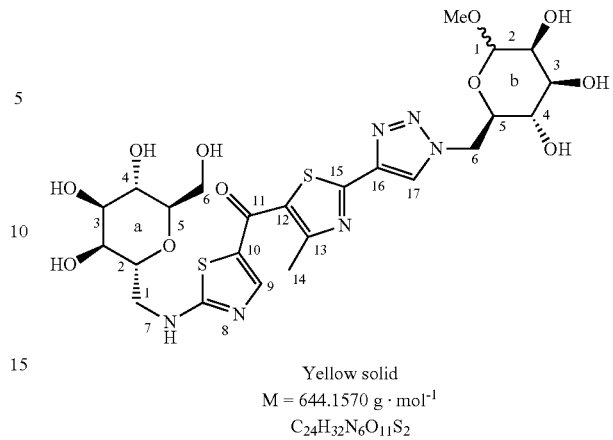

Yellow solid
M = 644.1570 g · mol⁻¹
$C_{24}H_{32}N_6O_{11}S_2$ $^1$H NMR (300 MHz, CDCl$_3$): δ (ppm): 8.52 (1H, s), 8.44 (1H, s), 7.95 (1H, s), 7.92 (1H, s), 5.12 (1H, d, $^3$J$_{1b-2b}$=1.3 Hz, H-1 b-α), 4.66 (1H, d, $^3$J$_{1b-2b}$=1.4 Hz, H-1 b-β), 4.08-4.21 (2H, m), 3.46-3.98 (28H, m), 3.30 (6H, s, OMe), 2.46 (3H, s, H-14), 2.44 (3H, s, H-14), HRMS, MALDI: [M−H]$^-_{calc}$=643.1492, [M−H]$^-_{mes}$=643.1467

Compound 3c

Intermediate 3c1

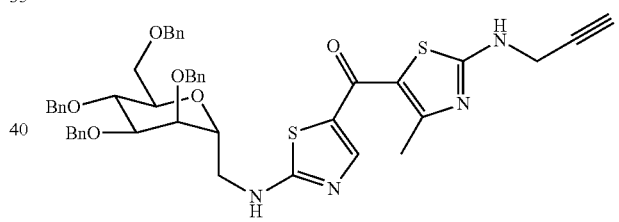

Chemical Formula: $C_{46}H_{46}N_4O_6S_2$
Exact Mass: 814.2859
Molecular Weight: 815.0160

According to the general procedure A, using the thiourea 2c4 (130 mg, 0.212 mmol) and 2-chloro-1-(2-(prop-2-yn-1-ylamino)thiazol-5-yl)ethan-1-one (Intermediate 2n1, 63 mg, 0.276 mmol) as starting materials, the derivative 3c1 (125 mg, 0.153 mmol, 72%) was obtained after purification by silica gel column chromatography (EtOAc as eluents) as a yellowish oil.

$^1$H NMR (400 MHz, CDCl$_3$) δ 2.35 (1H, t, J=2.5 Hz, propargylamine), 2.57 (3H, s, methylthiazol), 3.49 (1H, dd, J$_{7a,7b}$=13.4 Hz, J$_{7a,1}$=6.6 Hz, H-7a), 3.57-3.63 (2H, m, H-7b, H-6a), 3.67-3.72 (2H, m, H-2, H-3), 3.81-3.87 (2H, m, H-4, H-6b), 4.05-4.11 (2H, m, H-1, H-5), 4.14 (2H, d, J=2.5 Hz, propargylamine), 4.37-4.55 (8H, m, 4×BnO), 6.36 (1H, bs, NH), 7.18-7.36 (20H, m, 4×BnO), 7.87 (1H, s, thiazol).

[α]$_D$=+35 (c=1.4 in CHCl$_3$)

m/z [M+H]$^+$ 815; HRMS (ESI) m/z calcd for $C_{46}H_{47}N_4O_6S_2$[M+H]$^+$ 815.2941, found 815.2932.

Intermediate 3c2

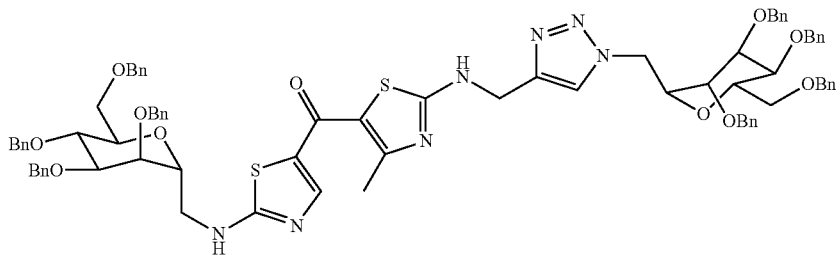

Chemical Formula: $C_{81}H_{83}N_7O_{11}S_2$
Exact Mass: 1393.56
Molecular Weight: 1394.70

To a solution of mannosyl alkyne 3c1 (140 mg, 0.170 mmol) and 1-Carbo-1-azido-2,3,4,6-tetra-O-benzyl-α-D-mannopyranose (compound 2c1, 129 mg, 0.223 mmol) in a mixture 3:1 of 1,4-dioxane-H2O (3.7 ml) were added $CuSO_4$ (5.5 mg, 0.034 mmol) and VitC Na (13 mg, 0.068 mmol) and the mixture was warmed up at 70° C. After 8 h, the mixture was concentrated and the crude was purified by silica gel column chromatography (DCM/AcOEt: 50/50→30/70 as eluents) to give the triazol 3c2 (204 mg, 0.146 mmol, 86%) as a colorless oil.

$[α]_D$=+10 (c=0.4 in $CHCl_3$); $^1H$ NMR (400 MHz, $CDCl_3$) δ 2.58 (3H, s, methylthiazol), 3.48-3.86 (12H, m), 4.04-4.26 (4H, m, H-1, H-1', H-5, H-5'), 4.37-4.55 (19H, m, 8×BnO, $CH_2$-triazol, H-7'a), 4.69 (1H, dd, $J_{7a,7b}$=14.4 Hz, $J_{7a,1}$=2.5 Hz, H-7'b), 6.83 (1H, bs, NH), 7.03 (1H, bs, NH), 7.18-7.37 (40H, m, 8×BnO), 7.86 (1H, s, thiazol), 7.88 (1H, s, triazol); $^{13}C$ NMR (127 MHz, $CDCl_3$) δ 18.6 ($CH_3$, methylthiazol), 40.3 ($CH_2$, $CH_2$-triazol), 46.4 ($CH_2$, C-7), 51.0 ($CH_2$, C-7'), 67.7, 67.9 (2$CH_2$, C-6, C-6'), 68.6 (2CH, C-1, C-1'), 71.2, 71.3, 71.9, 72.3, 72.5, 72.7, 73.0, 73.18 (8$CH_2$, 8×BnO), 72.6, 73.13, 73.4, 73.9, 74.1, 74.2, 74.5, 74.7 (8CH), 116.2 (C), 123.8 (CH, triazol), 127.5-128.4 (40CH, 8×BnO), 128.9 (C), 137.4-137.9 (8C, 8×BnO), 143.1 (C), 148.1 (CH, thiazol), 159.0, 169.3, 174.2, 176.0 (4C). m/z $[M+H]^+$ 1395; HRMS (ESI) m/z calcd for $C_{81}H_{84}N_7O_{11}S_2[M+H]^+$ 1394.5684, found 1394.5665.

Compound 3c

According to the general procedure C, using the derivative 3c2 (150 mg, 0.107 mmol) as starting materials, the derivative 3c (64 mg, 0.095 mmol, 89%) was obtained after purification by silica gel column chromatography (AcOEt/MeOH, 70:30 as eluent) as an amorphous white solid.

$[α]_D$=+13 (c=0.7 in MeOH); $^1H$ NMR (400 MHz, $D_2O$) δ 2.45 (3H, s, methylthiazol), 3.63-3.86 (12H, m), 3.99 (2H, q, J=3.2 Hz), 4.19 (1H, m, H-1), 4.32 (1H, m, H-1'), 4.67 (1H, dd, $J_{6a,6b}$=15.0 Hz, $J_{6a,5}$=3.6 Hz, H-6a), 4.74 (2H, s, $CH_2$-triazol), 4.89 (1H, dd, $J_{6b,6a}$=15.0 Hz, $J_{6b,5}$=3.6 Hz, H-6b), 7.95 (1H, s, triazol), 8.16 (1H, s, thiazol); $^{13}C$ NMR (127 MHz, $D_2O$) δ 15.1 ($CH_3$, methylthiazol), 40.9 ($CH_2$, $CH_2$-triazol), 44.3 ($CH_2$, C-7'), 48.3 ($CH_2$, C-7), 60.6, 60.7 (2$CH_2$, C-6, C-6'), 67.3, 67.4, 68.5, 68.6, 70.63, 70.66, 74.7, 75.2, 75.5, 76.0 (10CH), 115.1 (C), 125.4 (CH, triazol), 126.6, 141.5, 143.7 (3C), 149.4 (CH, thiazol), 169.3, 173.6, 176.3 (3C). m/z $[M+H]^+$675; HRMS (ESI) m/z calcd for $C_{25}H_{36}N_7O_{11}S_2[M+H]^+$ 674,1914, found 674,1921.

Stability Test

To demonstrate the instability under physiological conditions, in particular in the acidic medium of the stomach (in particular for compounds administered per os), of the compounds of formula (IV) and (IV') of WO 2014/016361 which is in the α-configuration, the following experiment has been designed.

Figure 10:
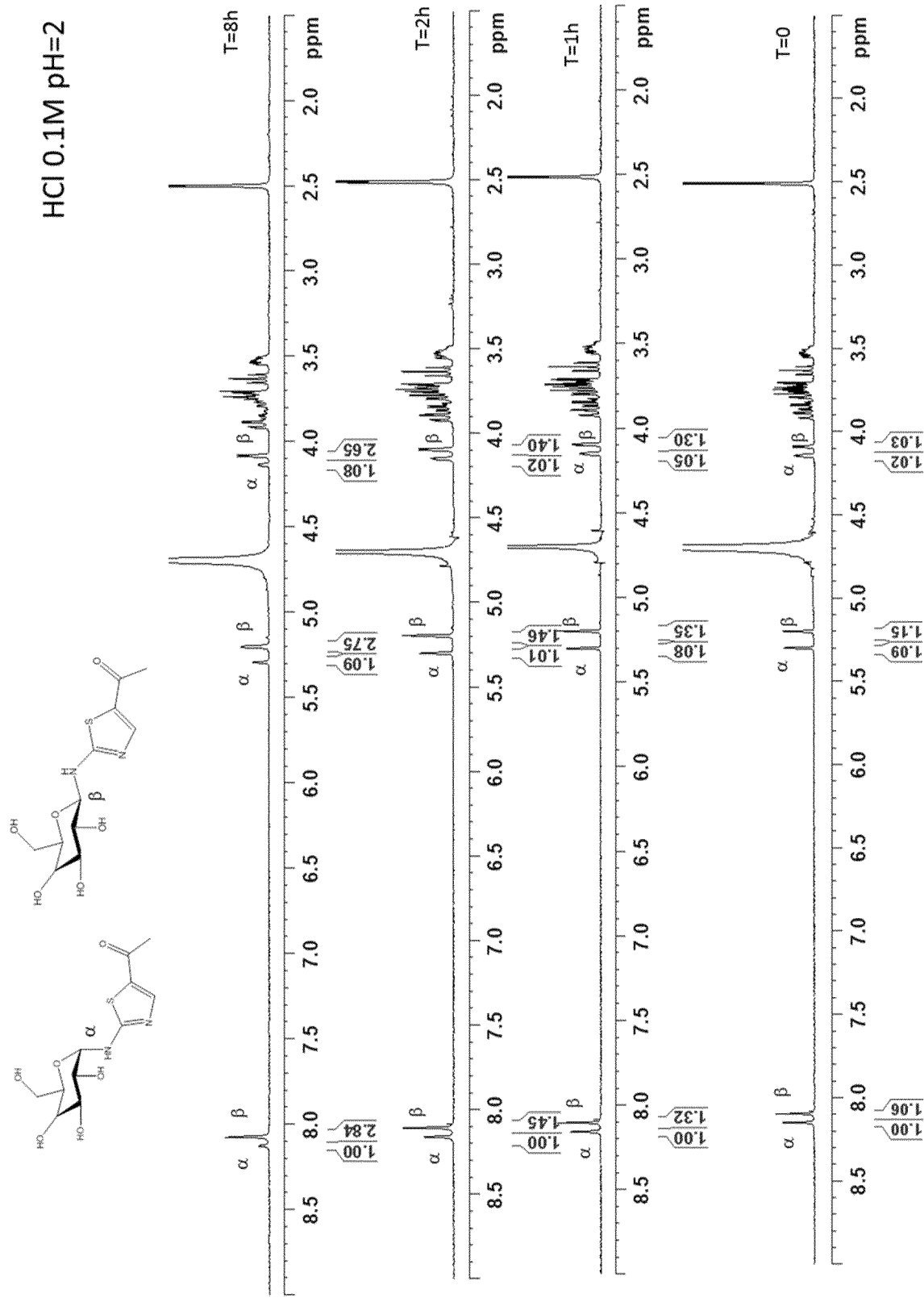
FIG. 10. $^1$H NMR spectra of Compound 13 of WO 2014/016361 in 0.1M HCl in $D_2O$ at t=0, 1 h, 2 h and 8 h (from bottom to top). Horizontal scale: chemical shift (δ) in ppm.
Figure 11:
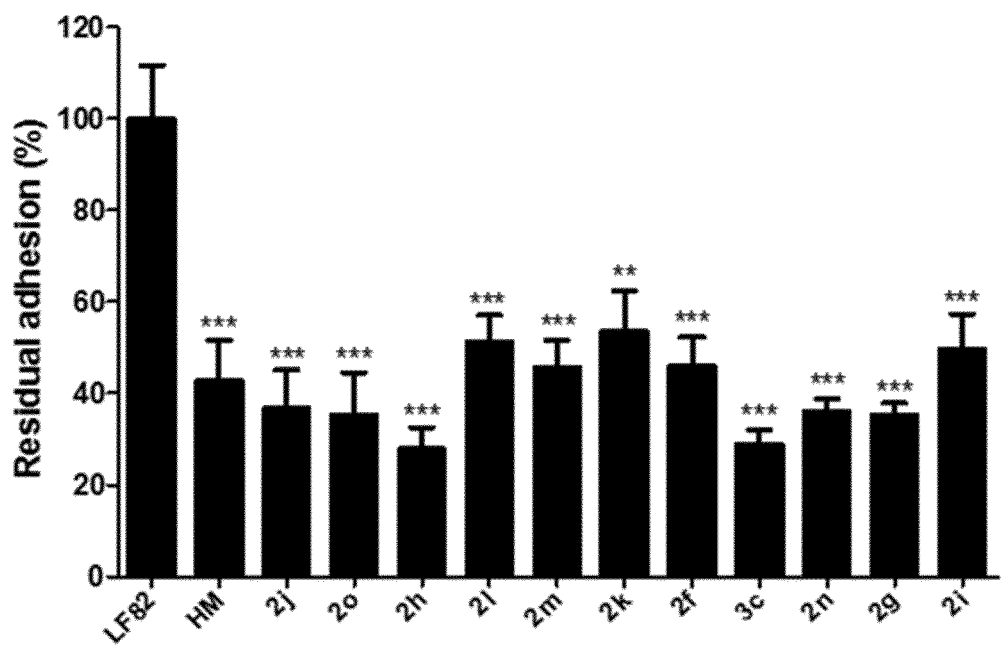
FIG. 11. Comparison of the inhibitory effect of the tested compounds on the ability of the AIEC strain LF82 to adhere to T84 cells obtained with HM (heptyl mannose) and the compounds of the following examples at 10 μM concentration, following a pre-incubation protocol. Results (Vertical scale) are expressed as percentages of bacteria adhering to the cells (means±SEM). 100% corresponds to adhesion in the absence of treatment (LF82, control). The stars indicate that the results are significant, in particular as compared with HM (heptyl mannose). More stars indicate a more significant result.

Compound 6 of WO 2014/016361 was dissolved in 0.1 M HCl and sample were freeze dried at t=0, 1 h, 2 h and 8 h (see FIG. 10). They were then dissolved in $D_2O$ and analyzed by $^1H$ RMN

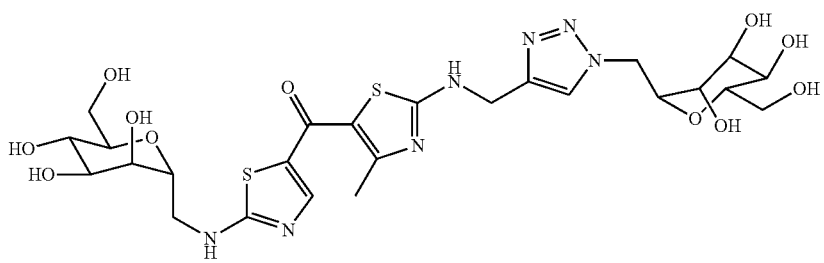

Chemical Formula: $C_{25}H_{35}N_7O_{11}S_2$
Exact Mass: 673.18
Molecular Weight: 673.72

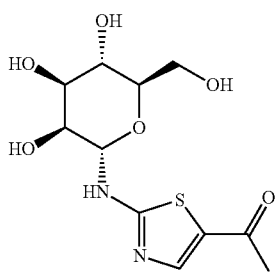 [SMILES: CC(=O)c1cnc(N[C@H]2O[C@H](CO)[C@@H](O)[C@H](O)[C@@H]2O)s1]

Compound 6 of WO 2014/016361

This experiment shows that compound 6 of WO 2014/016361 isomerizes to the corresponding β-mannose derivative. Indeed, under the acidic conditions, an equimolar α/β mixture at T=0 anomerize to a 1/3 α/β mixture at T=8 h.

In contrast, the corresponding compound 1a does not isomerize under the same acidic conditions.

II. Pharmacological Results

General Procedure for Hemagglutination Assays.

Interaction of E. coli FimH adhesins with the glycocalyx of guinea pig erythrocytes forms a crosslinked network in the wells. Glycoconjugates, added in a 2-fold dilution series, prevent the agglutination reaction. The inhibition titer is defined as the lowest concentration of the glycoconjugate at which hemagglutination is still inhibited. Several strains of E. coli were grown statically overnight in LB at 37° C., washed three times in ice-cold phosphate-buffered saline, and redissolved. A 2-fold dilution of glycoconjugates with a starting concentration of 1 mM was prepared in 25 μL of PBS with 10% of DMSO. Importantly, the pipet tip was changed at every dilution step to avoid carry-over. Next, the bacterial solution (25 μL) was added to the 2-fold dilution series of the compound. Finally, 50 μL of guinea pig red blood cells, washed and diluted in the buffer to 5% of the blood volume, was added to reach 100 μL. The plates were left on ice for one night before read-out.

Figure 2:
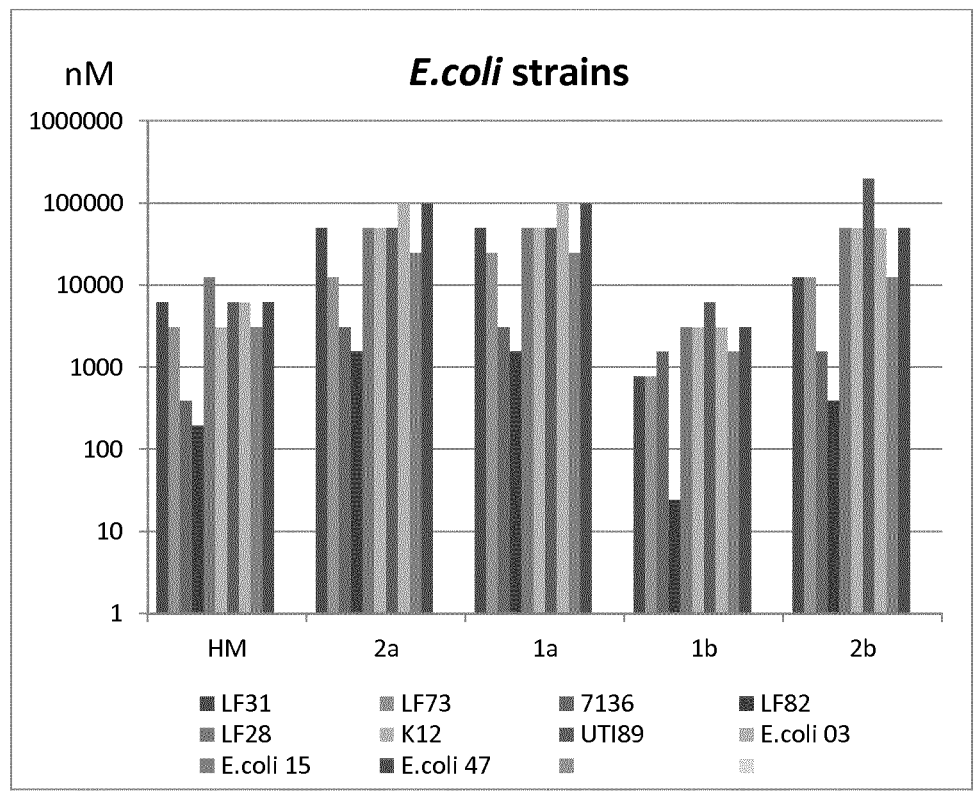
FIG. 2. Inhibition of Haemagglutination by different *E. coli* strain. The formation of the cross-linked network due to the interaction of the *E. coli* FimH adhesins with the glycocalyx of the erythrocytes was prevented at a certain concentration of inhibitors. The minimal inhibitory concentration (MIC) for the tested compounds is expressed in nanomolar (nM) on a logarithmic scale. Due to serial dilutions, the error is ±one well or a factor of two.
Figure 3:
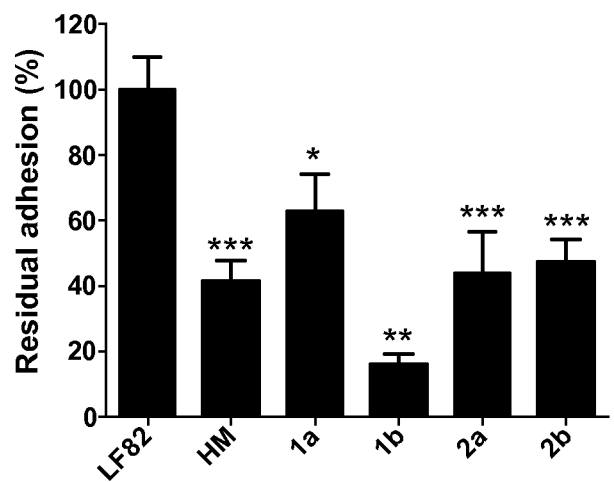
FIG. 3. Comparison of the inhibitory effect of the tested compounds on the ability of the AIEC strain LF82 to adhere to T84 cells obtained with HM (heptyl mannose) and the compounds of the following examples at 10 μM concentration, following a pre-incubation protocol. Results (Vertical scale) are expressed as percentages of bacteria adhering to the cells (means±SEM). 100% corresponds to adhesion in the absence of treatment (LF82, control).
Figure 4:
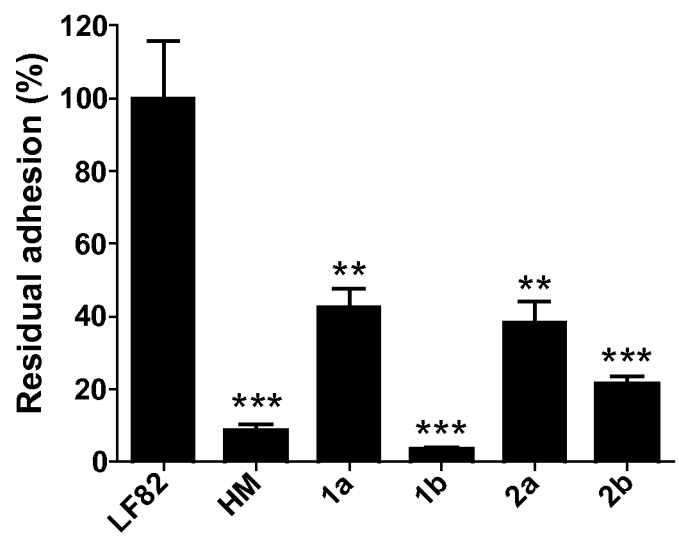
FIG. 4. Comparison of the inhibitory effect of the tested compounds on the ability of the AIEC strain LF82 to adhere to T84 cells obtained with HM (heptyl mannose) and the compounds of the following examples at 50 μM concentration, following a post-incubation protocol. Results (Vertical scale) are expressed as percentages of bacteria adhering to the cells (means±SEM). 100% corresponds to adhesion in the absence of treatment (LF82, control).

The results are shown on FIGS. 1 and 2.

Inhibition of E. coli Strain UTI89 Isolated from Patient with Urinary Tract Infection.

FIG. 1 shows that compounds 2c, 2d and HM are potent inhibitors of UTI89-induced hemagglutination. Compound 2c was the most potent of the series with a low inhibition titer of 98 nM.

Inhibition of Different E. coli Strains

The anti-adhesive capacity of the inhibitors was evaluated against ten E. coli strains isolated from CD patients, urinary tract infections, and hip prosthesis infections.

The results are presented on FIG. 2.

The results showed the capacity of the inhibitors to disrupt the cell-attachment of various E. coli strains isolated from CD patients, urinary tract infections, and hip prosthesis infections. The best inhibitor of the serie (1b) was effective against the whole set of bacterial strains at low concentrations with MIC values ranging from 24 nM against LF82 to 6 μM against UTI89. This is indicative that a unique antiadhesive compound can be used to treat different type of E. coli infections.

1. Adhesion Assays of UPEC UTI89 Strain on urinary tract epithelial cells
2. The antiadhesive potency of compounds 2c, 2d, belonging to the subset of molecules were Y=NH, was compared to the reference HM. HM is a nanomolar FimH antagonist and is often used in literature as a potent reference in cell-based assays with UPEC UTI 89 strains.

The results are presented on FIG. 1.

The results showed the increased anti-adhesive effect of compound 2c compared to 2d with MIC values of 98 nM and 3125 nM, respectively. The additional pharmacophores grafted on 2c therefore play a critical role by improving the intrinsic affinity of the thiazolylmannoside core for FimH. Compound 2c was 8-fold more potent than HM at disrupting the E. coli promoted hemagglutination.

Adhesion Assays of AIEC LF82 Strain on Intestinal Epithelial Cells

In order to obtain relevant in vitro results regarding the inhibition of the adhesion of AIEC bacteria, aiming at discriminating the potential of the tested compounds in treating for instance Crohn's Disease, The prepared compounds were evaluated for their ability to inhibit the adhesion of bacteria on AIEC LF82 intestinal cells, in order to assess the potential of the tested compounds in treating for instance Crohn's Disease.

Materials and Methods

E. coli strain LF82 isolated from an ileal biopsy of a CD patient was used as the AIEC reference strain. Bacteria were grown overnight at 37° C. in Luria-Bertani (LB) broth, and a bacterial suspension was prepared at a concentration of $1.5\times10^8$ bacteria/mL in phosphate buffer saline (PBS) for adhesion assays. The human intestinal cell line T84, purchased from American Type Culture Collection (ATCC, CCL-248), was maintained in an atmosphere containing 5% CO2 at 37° C. in the culture medium recommended by ATCC. T84 cells were seeded in 48-well tissue culture plates at a density of $1.5\times105$ cells/well and incubated at 37° C. for 48 h.

Pre-Incubation

AIEC reference strain LF82 was incubated for 1 h with HM or thiazole-bearing mannosides at final concentrations of 0.1, 1, or 10 μM, then bacteria/mannosides solution were incubated with T84 cells in order to have a multiplicity of infection (MOI) of 10 bacteria per cell ($1.5\times106$ bacteria/well) for 3 h with. Effects of mannoside treatment were compared with HM. Monolayers were washed three times with PBS and lysed with 1% Triton X-100 (Sigma) in deionized water. Samples were diluted and plated onto LB agar plates to determine the number of colony-forming units (CFU).

Post-Incubation

Cells were washed with PBS and infected, then incubated for 3 h with the AIEC reference strain LF82 for 3 h at a multiplicity of infection (MOI) of 10 bacteria per cell ($1.5\times106$ bacteria/well). the cells were washed 4 time with PBS, then incubated 3 h with HM or thiazole-bearing mannosides at the final concentration of 50 μM. Effects of mannoside treatment were compared with HM. Monolayers were washed three times with PBS and lysed with 1% Triton X-100 (Sigma) in deionized water. Samples were diluted and plated onto LB agar plates to determine the number of colony-forming units (CFU).

Results

The results depicted in FIGS. 3, 4, 5 and 11 show the potency of the compounds to inhibit the attachment of LF 82 to intestinal epithelial cells T84. In particular, compound 2b is more potent than the reference compound heptylmannoside, which is however a nanomolar inhibitor FimH. These results were obtained using both a preincubation protocol (wherein the tested compound is brought into contact with the bacteria before interacting with the cells, see FIGS. 3, 5 and 11) and a post-incubation protocol (wherein the tested compound is added after the bacteria are brought into contact with the cells, see FIG. 4). These pre-incubation and post-incubation tests respectively mimick a use of the compounds in a preventive and curative treatment (prophylactic and therapeutic) of pathologies associated with AIECs, in particular Crohn's disease.

Figure 12:
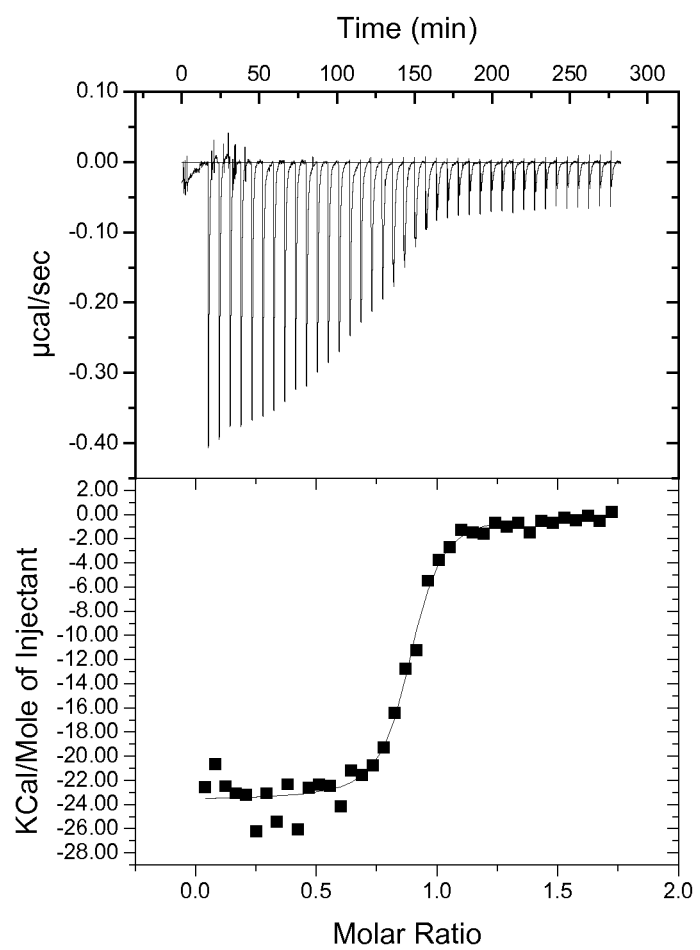
FIG. 12. Summary of the Isothermal Titration Calorimetry experiment of the FimH-compound 3c interaction. The bottom abscissa axis represents the molar ration, the upper abscissa axis represents the time (in min), the ordinate axis of the bottom graph represents the Kcal/Mol of injectant, and the ordinate axis of the upper graph represents the μcal by second (μcal/sec).
Figure 13:
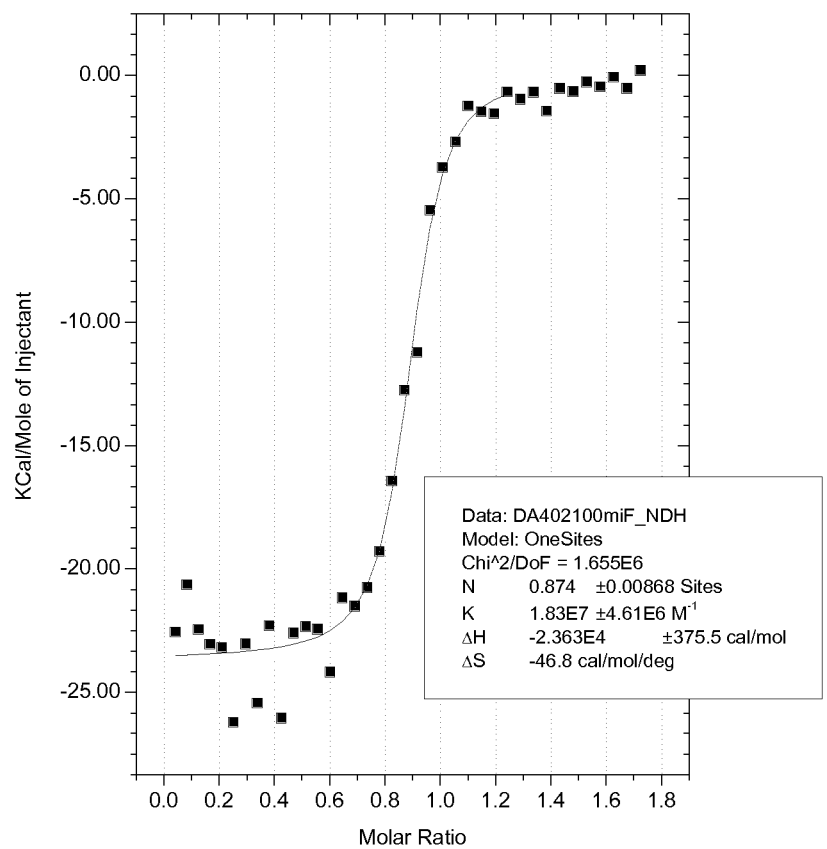
FIG. 13. Fitting of the enthalpogram of compound 3c, which allowed determining the thermodynamic parameters of the interaction:
Kd=0.546+/−0.02169 10-7 M=54.6+/−2.169 nM
n=0.874+/−0.00868 sites
ΔH=−23.630+/−0.3755 kCal/mole
ΔS=−46.8 cal/mol/deg
T=22.07696 deg (Celsius).
The abscissa axis represents the molar ration, the ordinate axis represents the Kcal/Mol of injectant.

Isothermal Titration Calorimetry (ITC) for Measuring the FimH Lectin Domain—DA402 Interaction The recombinantly expressed FimH lectin domain (residues 1-158) from E. coli strain UTI89 was purified as described previously by Wellens et al. The FimH protein solution was put into the measurement cell (1452 µl) of a VP-ITC microcalorimeter (Malvern), at a concentration of 11.83 µM in the ITC working buffer (20 mM Na-Hepes at pH 7.4 and 150 mM NaCl). Compound 3c at 100 µM concentration was titrated into the FimH solution using 38 injections of 7 µl, leading to 38 heat peaks measured in µcal/sec (FIG. 12). The heat peaks were integrated (kCal/mole of injectant) to be presented in an enthalpogram with 38 data points (FIG. 12), used for the fitting to the model of one kind of binding sites (Microcal ITC Origin software) in order to derive the affinity (K) and the stoichiometry (N) of the interaction (FIG. 13). Using the constant absolute temperature (T) of the experiment, the entropic contribution ΔS was calculated (FIG. 13).

Plasma and faeces concentrations after administration of Compound 1b and for compound 13 of WO 2014/016361 at 1 mg/kg by intravenous route and 10 mg/kg by oral route to Sprague Dawley rats 1. Test Substances 2 compounds are tested: compound 1b of the present invention and compound 13 of WO 2014/016361:

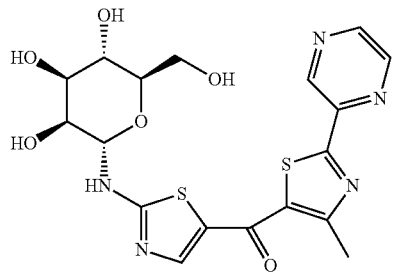 [SMILES: Cc1nc(-c2cnccn2)sc1C(=O)c1cnc(N[C@H]2O[C@H](CO)[C@@H](O)[C@H](O)[C@@H]2O)s1]

Compound 13 of WO 2014/016361

The test substances are stored at room temperature in the dark.

For analysis, the molecules are dissolved in DMSO at 1 mg/mL.

| Weight tube (mg) |
|---|
| 2 * 1 mg for the analytical part |
| 15 mg for the in vivo part |

2. Analytical Test

Before the beginning of the in vivo part, an analytical test for each compound is performed in the two matrices.

The molecular and daughter ions are selected for each compound by direct infusion into the MS-MS system.

At least 8 point calibration standards are run using standard conditions which consist to LC-MS/MS system with C18 column after precipitation of proteins with acetonitrile before the start of the analytical test.

Blank rat faeces are homogenized with 3 volumes of UHQ water until obtention of a paste. Then 100 µL of the homogenate are spiked with the molecules and precipitated with 300 µL of acetonitrile.

For the plasma, 100 µL of blank rat plasma are directly spiked with the compounds before being precipitate with 300 µL of acetonitrile.

The corresponding correlation coefficient (r) is calculated and is higher than 0.75 to continue with the in vivo test.

The concentration ranges tested are:
0.5 ng/mL to 1000 ng/mL for plasma,
4 to 2000 ng/g for faeces, corresponding to 1 to 500 ng/mL of faeces homogenate.

3. In-Life Part 3.1. Characteristics, Housing and Handling of Animals 12 male Sprague Dawley rats around 6-7 week old are used. Upon arrival, the animals are numbered randomly and identified by an ear-tag. The animals are registered into the animal reception and usage register and then observed for at least 3 days. Their health is verified by observation.

Upon receipt, the animals are housed in makrolon cages with stainless steel wire lids with catches.

The litter of the animals is renewed at least every 72 hours. Temperature and humidity are continually monitored. The animal room conditions are kept as follows:

Temperature: 22° C.±2° C. Exceptionally, upper or lower values can be tolerated.

Light/dark cycle: 12 h/12 h (07:00 h-19:00 h).

After administration and over the experiment duration, the animals are placed individually in metabolic cages (tecniplast).

Animals have free access to food and water during the experiment.

3.2. Design

| Route | Vehicle | Dose (mg/kg) | Concentration | Volume of administration (mL/kg) |
|---|---|---|---|---|
| IV | 100% DMSO | 1 | 1 mg/mL | 1 |
| PO | 100% DMSO | 10 | 2 mg/mL | 5 |

3.3. Sampling

For each test substance:

| Administration route | Rat name | Blood sampling Time | Faeces sampling Time |
|---|---|---|---|
| IV | IV1, IV2, IV3 | 5 min | 0-24 h |
|  |  | 30 min |  |
|  |  | 2 h |  |
|  |  | 6 h |  |
|  |  | 24 h |  |
| PO | PO4, PO5, PO6 | 30 min | 0-24 h |
|  |  | 1 h |  |
|  |  | 2 h |  |
|  |  | 6 h |  |
|  |  | 24 h |  |

After administration, the animals are placed in individual metabolic cages in order to collect faeces samples during 24 hours.

3.4. Blood Sampling

At prescribed times, blood is collected. Animals are briefly anaesthetised with Isoflurane® using an anaesthetic system (Équipement Vétérinaire Minerve) during blood samplings.

Site of collection: sinus retro-orbital using a capillary tube
Volume of blood collected: 0.3 mL per time-point
Anticoagulant: Heparin Lithium
Exact sampling times are noted for each blood sampling.
Blood samples are centrifuged at 2500 rpm at +4° C. (between 0 and 9° C.), the plasma is removed and placed into labelled polypropylene tubes. Individual plasma samples are stored frozen at −20° C. (target temperature) until analysis.

4. Analysis 4.1. Analysis of Plasma Samples

100 µL of the plasma sample are taken and 300 µL of acetonitrile are added. After protein precipitation, analysis is performed using LC-MS/MS determination according to previous analytical test results.

4.2. Analysis of Faeces Samples

Faeces samples are collected over the 24 hours of the experiment.
They are precisely weighed and 3 volumes of UHQ water are added.
The mixture is homogeneized until obtention of a paste.
Then 100 µL of the homogenate are taken and extracted with 300 µL of Acetonitrile.
Analysis is performed using LC-MS/MS determination according to previous analytical test results.

4.3. Determination of the Concentrations

Concentrations of the samples are calculated directly from chromatograms after automatic integration by Analyst® 1.5.1 and expressed as ng/mL.
Mean plasma concentrations are calculated (when calculable, i.e. n≥2) using individual concentration and are expressed with the corresponding standard deviation value and variation coefficient (when calculable, i.e. n≥3), with $$CV(\%) = \frac{SD}{Cmean} \times 100.$$

The individual plasma concentrations are tabulated for each rat and scheduled sampling time. Concentrations below the LLOQ are indicated by BLQ. All BLQ concentrations are substituted by zero for calculation of the descriptive statistics of the concentrations.

5. Results

Estimation of pharmacokinetics parameters is performed using Kinetica® (Version 4.3—Thermo Electron Corporation—Philadelphia—USA). It was performed by using a one-compartment model approach, which considers the body as a single compartment in which the concentration is homogeneous.
The following parameters are estimated:
Cmax (ng/mL): maximal plasma concentration
Tmax (h): first time to reach Cmax
$AUC_t$ (ng/mL*h): area under the plasma concentration-time curve from administration up to the last quantifiable concentration at time t $$\text{Absolute bioavailability } F(\%) = \frac{AUC\ PO/\text{dose } PO}{AUC\ IV/\text{dose } IV} * 100$$

"BLQ" stands for "Below the Limit of Quantification" (5 ng/mL for plasma).

Compound 1b

| IV route | Sampling time (h) | IV1 | IV2 | IV3 | Mean | SD | CV |
|---|---|---|---|---|---|---|---|
| Plasma (ng/mL) | 0.083 | 572.7 | 470.2 | 908.7 | 650.5 | 229.4 | 35.3 |
| | 0.5 | 59.6 | 108.2 | 66.5 | 78.1 | 26.3 | 33.7 |
| | 2 | BLQ | 7.7 | BLQ | 2.6 | NC | NC |
| | 6 | BLQ | BLQ | BLQ | 0.0 | NC | NC |
| | 24 | BLQ | BLQ | BLQ | 0.0 | NC | NC |
| Faeces (ng/mL) | 0-24 | 889 | 1608 | 569 | 1022 | 532 | 52 |
| Faeces (ng/g) | 0-24 | 3557 | 6433 | 2274 | 4088 | 2129 | 52 |
| Weight of faeces (g) | 0-24 | 7 | 3 | 9 | 6 | 3 | 42 |
| | | | | | | | 42 |
| Total amount of 1b (ng) | 0-24 | 25318 | 22175 | 19840 | 22445 | 2749 | 12 |
| Volume administered (mL) | | 0.24 | 0.24 | 0.29 | | | |
| Recovery in faeces (%) | 0-24 | 10.5 | 9.2 | 6.8 | 8.9 | 1.9 | 21.2 |

The results are reported on FIG. 6.

| PO route | Sampling time (h) | PO4 | PO5 | PO6 | Mean | SD | CV |
|---|---|---|---|---|---|---|---|
| Plasma (ng/mL) | 0.5 | 6.7 | 8.1 | 6.5 | 7.1 | 0.9 | 12.7 |
| | 1 | 5.5 | 6.5 | BLQ | 4.0 | 3.5 | 87.5 |
| | 2 | 6.0 | BLQ | 5.2 | 3.7 | 3.2 | 87.3 |
| | 6 | BLQ | BLQ | BLQ | 0.0 | NC | NC |
| | 24 | BLQ | BLQ | BLQ | 0.0 | NC | NC |
| Faeces (ng/mL) | 0-24 | 36553 | 28874 | 36745 | 34058 | 4490 | 13 |
| Faeces (ng/g) | 0-24 | 146214 | 115495 | 146982 | 136230 | 17961 | 13 |
| Weight of faeces (g) | 0-24 | 9 | 9 | 8 | 9 | BLQ | 8 |

| PO route | Sampling time (h) | Rat PO4 | PO5 | PO6 | Mean | SD | CV |
|---|---|---|---|---|---|---|---|
| Total amount of 1b (ng) | 0-24 | 1335427 | 1081683 | 1171915 | 1196341 | 128624 | 11 |
| Volume administered (mL) | | 1.2 | 1.3 | 1.3 | | | |
| Recovery in faeces (%) | 0-24 | 55.6 | 41.6 | 45.1 | 47.4 | 7.3 | 15.4 |

Figure 7:
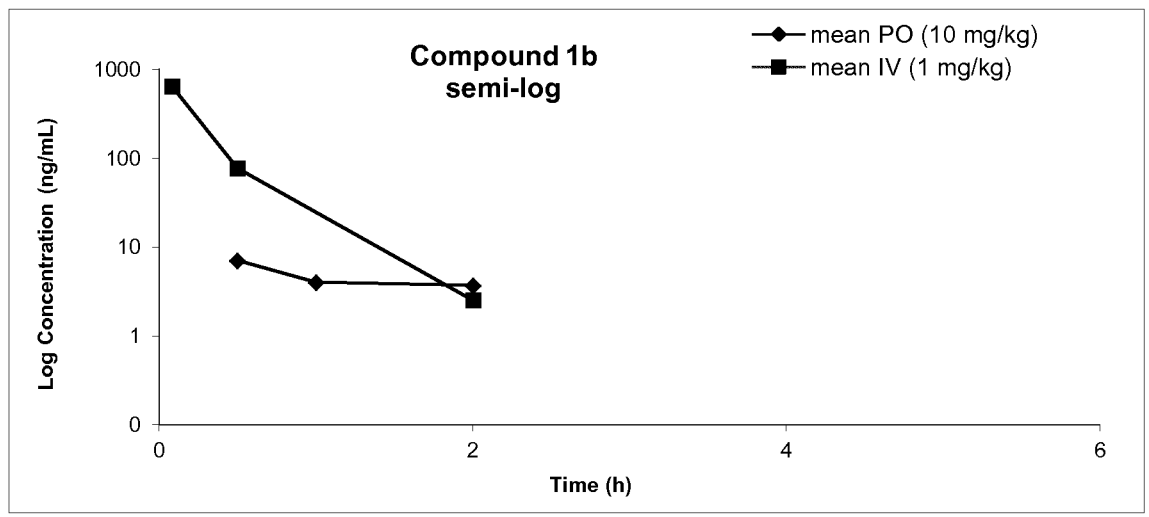
FIG. 7. Semi-logarithmic representation of the plasmatic concentrations after administration of Compound 1b to Sprague Dawley rats at 1 mg/kg by intravenous route (squares) and 10 mg/kg by oral route (diamonds). The X-axis represents the time (in hours), the Y-axis represents the logarithm of the plasmatic concentration of compound 1b in ng/L.

The results are reported on FIG. 7.
Compound 13 of WO 2014/016361

| IV route | Sampling time (h) | Rat IV1 | IV2 | IV3 | Mean | SD | CV |
|---|---|---|---|---|---|---|---|
| Plasma (ng/mL) | 0.083 | *1134.8* | *1451.7* | *1443.6* | 1343.4 | 180.7 | 13.5 |
| | 0.5 | 56.1 | 67.6 | 58.5 | 60.8 | 6.1 | 10.0 |
| | 2 | 1.6 | 1.6 | 1.8 | 1.6 | 0.1 | 6.2 |
| | 6 | BLQ | BLQ | BLQ | 0.0 | NC | NC |
| | 24 | BLQ | BLQ | BLQ | 0.0 | NC | NC |
| Faeces (ng/mL) | 0-24 | 826 | 783 | 836 | 815 | 28 | 3 |
| Faeces (ng/g) | 0-24 | 3303 | 3130 | 3346 | *3260* | 114 | 3 |
| Weight of faeces (g) | 0-24 | 9 | 9 | 11 | 10 | 1 | 13 |
| Total amount of compound 13 (ng) | 0-24 | 30095 | 28426 | 38053 | 32191 | 5144 | 16 |
| Volume administered (mL) | | 0.23 | 0.26 | 0.24 | | | |
| Recovery in faeces (%) | 0-24 | 13.1 | 10.9 | 15.9 | 13.3 | 2.5 | 18.6 |

Figure 8:
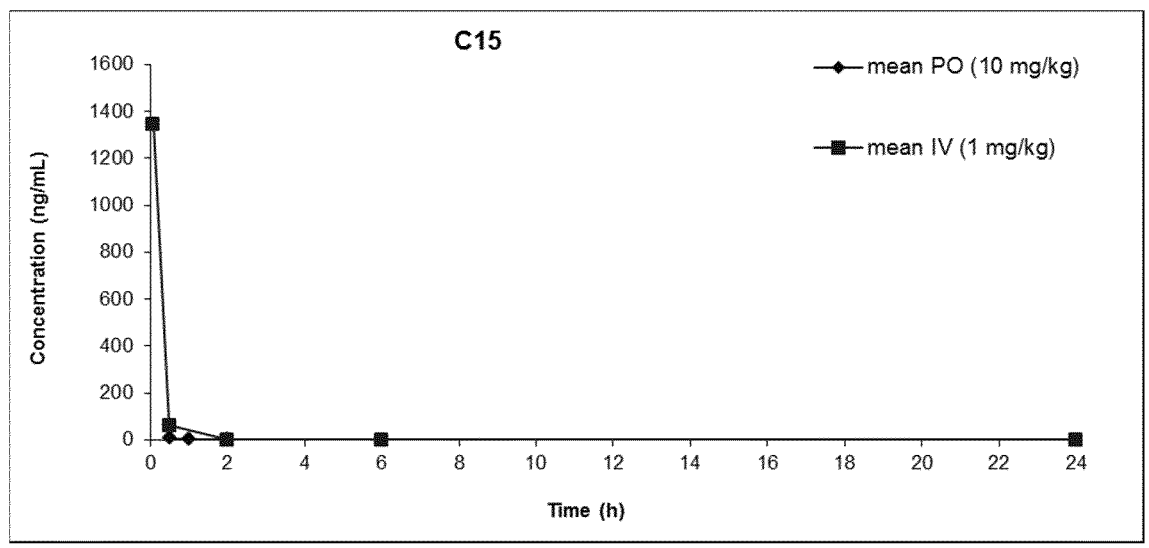
FIG. 8. Plasmatic concentrations after administration of Compound 13 of WO 2014/016361 to Sprague Dawley rats at 1 mg/kg by intravenous route (squares) and 10 mg/kg by oral route (diamonds). The X-axis represents the time (in hours), the Y-axis represents the plasmatic concentration of compound 1b in ng/L.

The results are presented on FIG. 8.

| PO route | Sampling time (h) | Rat PO4 | PO5 | PO6 | Mean | SD | CV |
|---|---|---|---|---|---|---|---|
| Plasma (ng/mL) | 0.5 | 5.5 | 10.9 | 7.0 | 7.8 | 2.8 | 36.0 |
| | 1 | 3.3 | 4.6 | 5.4 | 4.4 | 1.1 | 24.6 |
| | 2 | 1.9 | 2.3 | 2.0 | 2.0 | 0.2 | 9.1 |
| | 6 | 1.7 | 1.9 | 1.6 | 1.7 | 0.2 | 9.4 |
| | 24 | BLQ | BLQ | BLQ | 0.0 | NC | NC |
| Faeces (ng/mL) | 0-24 | 25979 | 41416 | 33134 | *33510* | 7725 | 23 |
| Faeces (ng/g) | 0-24 | 103917 | 165663 | 132537 | 134039 | 30900 | 23 |
| Weight of faeces (g) | 0-24 | 12 | 8 | 9 | 10 | 2 | 18 |
| Total amount of compound 13 (ng) | 0-24 | 1203583 | 1389086 | 1183679 | 1258783 | 113284 | 9 |
| Volume administered (mL) | | 1.2 | 1.2 | 1.2 | | | |
| Recovery in faeces (%) | 0-24 | 50.1 | 57.9 | 49.3 | 52.4 | 4.7 | 9.0 |

Figure 9:
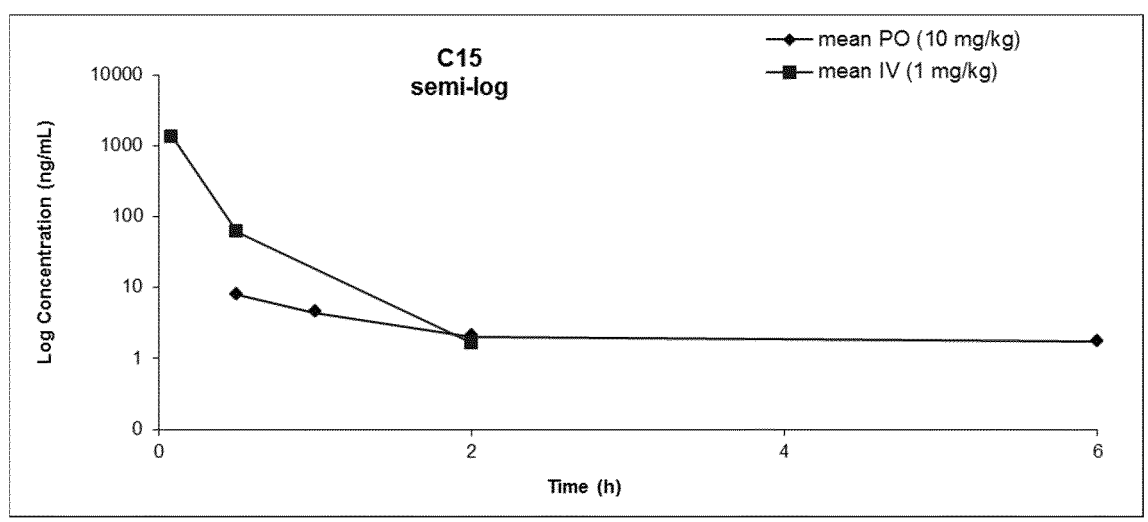
FIG. 9. Semi-logarithmic representation of the plasmatic concentrations after administration of Compound 13 of WO 2014/016361 to Sprague Dawley rats at 1 mg/kg by intravenous route (squares) and 10 mg/kg by oral route (diamonds). The X-axis represents the time (in hours), the Y-axis represents the logarithm of the plasmatic concentration of compound 1b in ng/L.

The results are presented on FIG. 9.

6. Pharmacokinetic Results

Main pharmacokinetics data are summarized in the table below:

PK Parameters Calculated Based on Mean Data

| Compound | Administration route | Vehicle | Dose (mg/kg) | Cmax (ng/mL) | Tmax (h) | $AUC_t$ (ng/mL*h) | $AUC_{inf}$ (ng/mL*h) | % $AUC_{extra}$ | F (%) |
|---|---|---|---|---|---|---|---|---|---|
| 13 of WO 2014/016361 | IV | DMSO | 1 | 1343.35 | 0.08 | 451 | 451.56 | 0.11 | 0.3 |
|  | PO |  | 10 | 7.79 | 0.50 | 16 | 23.26 | *32.3* |  |
| 1b | IV | DMSO | 1 | 650.52 | 0.08 | 266 | 267.34 | 0.35 | 0.3 |
|  | PO |  | 10 | 7.07 | 0.50 | 8 | 18.18 | *53.8* |  |

*italic: % AUC extra >20%: value given for indication*

F was calculated based on AUCt (Area under the Curve at t).

7. Conclusions

Plasmatic concentrations of both compounds display very low level of exposition after oral administration whose bioavailability calculated is under 0.3%.

Faecal concentrations of compounds have been assessed in a range from 200 to 100 000 ng/mL of homogenate. The estimations of quantity found in faeces out of the administered quantity for oral route are:

47.4% for compound 1b 52.4% for compound C13

Both compounds 1b and compound 13 of WO 2014/016361 are not passing through the intestinal barrier and keep large quantity of intact products in the faeces.

REFERENCES

Barghash et al *Org Biomol Chem.* 2009, 7, 3319-3330

Barnich N et al *J. Clin. Invest* 2007, 117, 1566-1574

Bonnet et al *Clin. Cancer Research* 2014, 20, 859-867

Bouckaert J et al. *Mol. Microbiol.* 2005, 55: 441-455.

Bouckaert J et al. *Mol. Microbiol.* 2006, 61: 1556-1568.

Bouckaert J et al. 2013 *Chemistry, a European Journal* 19: 7847-7855.

Boudeau J et al *Infect. Immun.* 1999, 67, 4499-4509

Bronowski et al *Microbiology* 2008, 154, 571-583

Brument et al *Journal of Medicinal Chemistry* 2013, 56(13), 5395-5406

Chen et al *PNAS* 2009, 106, 52, 22439-22444

Cho et al. *Gastroenterology* 2011, 140(6), 1704-12. doi: 10.1053/j.gastro.2011.02.046

Darfeuille-Michaud et al *Gastroenterology* 2004, 127 (2), 412-421

Dreux N. et al *PLOS Pathogens* 2013, 9, 1, e1003141

Greene, "Protective Groups In Organic synthesis" (John Wiley & Sons, New York (1981)

Halluin et al *Carbon* 2015, 93, 974-983.

Liu et al *Bioorg. Med. Chem. Lett.* 2012, 22 (19), 6190-6194,

Mansfield et al *J. Vet. Intern. Med.* 2009, 23, 964-969

Martin et al *Gastroenterology* 2004, 127, 80-93

Martinez-Medina et al *Inflammatory Bowel Dis.* 2009, 15, 6, 872-882

Martinez-Medina et al *Applied and Environmental Microbiology* 2011, 77, 16, 5813-5817

Martinez-Medina et al. 1 *Gut* 2014, 63, 116-124. doi: 10.1136/gutjnl-2012-304119

Martinez-Medina et al 2 *Gastrointest Pathophysiology* 2014, 5, 3, 213-227

Molodecky N A, et al. *Gastroenterology.* 2012

Raisch et al *Gastroenterology* 2014, 20, 21, 6560-6572

Schwardt et al *Bioorganic & Medicinal Chemistry* 2011, 19, 6454-6473

Sobieszczanska et al Polish *Journal of Microbiology* 2012, 61, 2, 105-110

Wellens et al. *PLoS ONE* 2008, 3(4), e204

The invention claimed is:

1. A compound of formula (I):

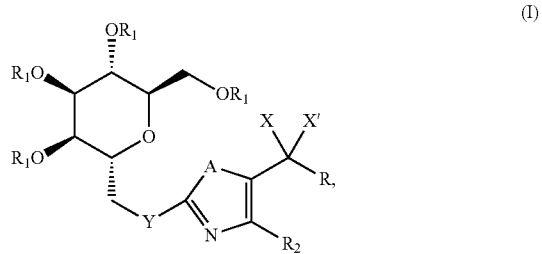

wherein $R_1$ represents H, CO—$(C_1$-$C_6)$-alkyl or CO-alkylaryl,

Y represents a single bond, $CH_2$, O, $NR_3$, S,

A represents O, NH or S,

X represents H and X' represents OH or X and X' taken together with the carbon atom bearing them form a CO group, $R_2$ represents H, a linear or branched $(C_1$-$C_6)$-alkyl or $CF_3$, $R_3$ represents H, a $C_1$-$C_6$ alkyl, a CO—$(C_1$-$C_6)$-alkyl, $CF_3$ or $COCF_3$, and R represents: a $(C_1$-$C_6)$-alkyl, a $(C_2$-$C_6)$-alkenyl, a $(C_2$-$C_6)$-alkynyl, a $(C_3$-$C_{10})$-cycloalkyl, a $(C_5$-$C_{10})$-cycloalkenyl, a heterocycloalkyl, a heterocycloalkenyl, an arylan alkyl aryl, $CF_3$, adamantyl, $OR_a$, or $NR_bR_c$, wherein $R_a$ represents H, a $(C_1$-$C_6)$-alkyl, a $(C_2$-$C_6)$-alkenyl, a $(C_2$-$C_6)$-alkynyl, a $(C_3$-$C_6)$-cycloalkyl, a $(C_3$-$C_6)$-cycloalkenyl, a heterocycloalkyl, a heterocycloalkenyl, an aryl, a alkylaryl, a CHO, a CO—$(C_1$-$C_6)$-alkyl, or CO-aryl, a $CO_2H$, a $CO_2$—$(C_1$-$C_6)$-alkyl, or a CONH—$(C_1$-$C_6)$-alkyl, and wherein $R_b$ and $R_c$ represent independently from each other any of the groups defined for $R_a$, said $(C_1$-$C_6)$-alkyl, $(C_2$-$C_6)$-alkenyl, $(C_2$-$C_6)$-alkynyl, $(C_3$-$C_{10})$-cycloalkyl, $(C_5$-$C_{10})$-cycloalkenyl, heterocycloalkyl, heterocycloalkenyl, CO—$(C_1$-$C_6)$-alkyl, $CO_2$—$(C_1$-$C_6)$-alkyl, CONH—$(C_1$-$C_6)$-alkyl, aryl, alkylaryl, CO-aryl and CO-alkylaryl being optionally substituted by one or more substituent(s) R', each independently selected from:

a $(C_1$-$C_6)$-alkyl optionally substituted by one or more, substituents selected from a halogen, $NH_2$, OH, $CF_3$, a $C_1$-$C_6$ alkyl unsubstituted or substituted by a carbohydrate, $CH_2SO_3T$, $CH_2COOT$ or $N(R_g)_3T'$, wherein $R_g$ represents independently H, a $(C_1-C_6)$-alkyl, T represents a monovalent cation and wherein T' is a monovalent anion, —a $(C_2-C_6)$-alkenyl,
a $(C_2-C_6)$-alkynyl,
a $(C_3-C_{10})$-cycloalkyl,
a $(C_5-C_{10})$-cycloalkenyl,
a heterocycloalkyl,
a heterocycloalkenyl,
an aryl, optionally substituted by one or more, substituents selected from a halogen, $NH_2$, OH, $CF_3$, a $C_1-C_6$ alkyl unsubstituted or substituted by a carbohydrate, $CH_2SO_3T$, $CH_2COOT$ or $N(R_g)_3T'$, wherein $R_g$, T and T' are as defined above,
an alkyl aryl optionally substituted by one or more substituents selected from a halogen, $NH_2$, OH, $CF_3$, a $C_1-C_6$ alkyl unsubstituted or substituted by a carbohydrate, $CH_2SO_3T$, $CH_2COOT$ or $N(R_g)_3T'$, wherein $R_g$, T and T' are as defined above,
a NH-alkyl aryl optionally substituted by one or more, substituents selected from a halogen, $NH_2$, OH, $CF_3$, a $C_1-C_6$ alkyl unsubstituted or substituted by a carbohydrate, $CH_2SO_3T$, $CH_2COOT$ or $N(R_g)_3T'$, wherein $R_g$, T and T' are as defined above,
a CHO,
a CO—$(C_1-C_6)$-alkyl optionally substituted by a halogen or a carbohydrate,
a CO-aryl optionally substituted by one or more substituents selected from a halogen, $NH_2$, OH, $CF_3$, a $C_1-C_6$ alkyl unsubstituted or substituted by a carbohydrate, $CH_2SO_3T$, $CH_2COOT$ or $N(R_g)_3T'$, wherein $R_g$, T and T' are as defined above,
a $CO_2H$,
a $CO_2$—$(C_1-C_6)$-alkyl,
a CONH—$(C_1-C_6)$-alkyl,
a CONH-aryl or NHCO-aryl optionally substituted by one or more substituents selected from a halogen, $NH_2$, OH, $CF_3$, a $C_1-C_6$ alkyl unsubstituted or substituted by a carbohydrate, $CH_2SO_3T$, $CH_2COOT$ or $N(R_g)_3T'$, wherein $R_g$, T and T' are as defined above,
a halogen,
$CF_3$,
$OR_d$, wherein $R_d$ represents: H, a $(C_1-C_6)$-alkyl, a $(C_3-C_{10})$-cycloalkyl, CO—$(C_1-C_6)$-alkyl, or CO-aryl optionally substituted by one or more substituents selected from a halogen, $CF_3$, a $C_1-C_6$ alkyl unsubstituted or substituted by a carbohydrate,
$NR_eR_f$, wherein $R_e$ and $R_f$ represent independently from each other: H, a $(C_1-C_6)$-alkyl, a $(C_3-C10)$-cycloalkyl, CO—$(C_1-C_6)$-alkyl, or CO-aryl optionally substituted by one or more substituents selected from a halogen, $CF_3$, a $C_1-C_6$ alkyl unsubstituted or substituted by a carbohydrate,
$NHR_b$, wherein $R_b$ is as defined above,
$NO_2$,
CN, and
$CH_2SO_3T$, $CH_2COOT$ or $N(R_g)_3T'$, wherein $R_g$, T and T' are as defined above,
or a pharmaceutically acceptable salt or solvate thereof.

2. The compound of claim 1, wherein $R_1$ represents H.
3. The compound of claim 1, wherein $R_2$ represents H.
4. The compound of claim 1, wherein A represents S.
5. The compound of claim 1, wherein X and X' taken together with the carbon atom bearing them forms a CO group.
6. The compound of claim 1, wherein Y is a single bond or NH.

7. The compound of claim 1, wherein R represents a $(C_1-C_6)$-alkyl, a heterocycloalkyl, a heterocycloalkenyl, an aryl, an alkyl aryl, $CF_3$, admantyl, $OR_a$, or $NHR_a$, wherein $R_a$ represents H, a $(C_1-C_6)$-alkyl, a cycloalkyl, a heterocycloalkyl, an aryl, or a alkylaryl, said $(C_1-C_6)$-alkyl, heterocycloalkyl, heterocycloalkenyl, aryl, and alkyl aryl being optionally substituted by 1, 2, 3 or 4 substituent(s) R', as defined in claim 1.

8. The compound of claim 1, wherein R' represents:
a $(C_1-C_6)$-alkyl optionally substituted by one or more, substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
a $(C_3-C_6)$-cycloalkyl,
a heterocycloalkyl,
a heterocycloalkenyl,
an aryl, optionally substituted by one or more substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
an alkyl aryl optionally substituted by one or more substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
a CHO,
a CO—$(C_1-C_6)$-alkyl optionally substituted by a halogen,
a CO-aryl optionally substituted by one or more, substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
a $CO_2H$,
a $CO_2$—$(C_1-C_6)$-alkyl,
a CONH—$(C_1-C_6)$-alkyl,
a NHCO-aryl optionally substituted by one or more, substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
a NH-alkyl aryl optionally substituted by one or more, substituents selected from a halogen, $NH_2$, OH, $CF_3$, a $C_1-C_6$ alkyl substituted by a carbohydrate, $CH_2SO_3T$, $CH_2COOT$ or $N(R_g)_3T'$, wherein $R_g$, T and T' are as defined in claim 1,
a halogen,
$CF_3$,
$OR_d$, wherein $R_d$ represents H or a $(C_1-C_6)$-alkyl,
$NR_eR_f$, wherein $R_e$ and $R_f$ represent independently from each other: H, or a $(C_1-C_6)$-alkyl,
$NHR_b$, wherein $R_b$ is as defined above,
$NO_2$, and
CN.

9. The compound of claim 1, wherein R represents methyl,

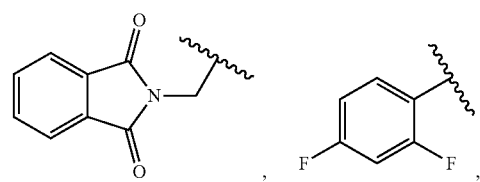

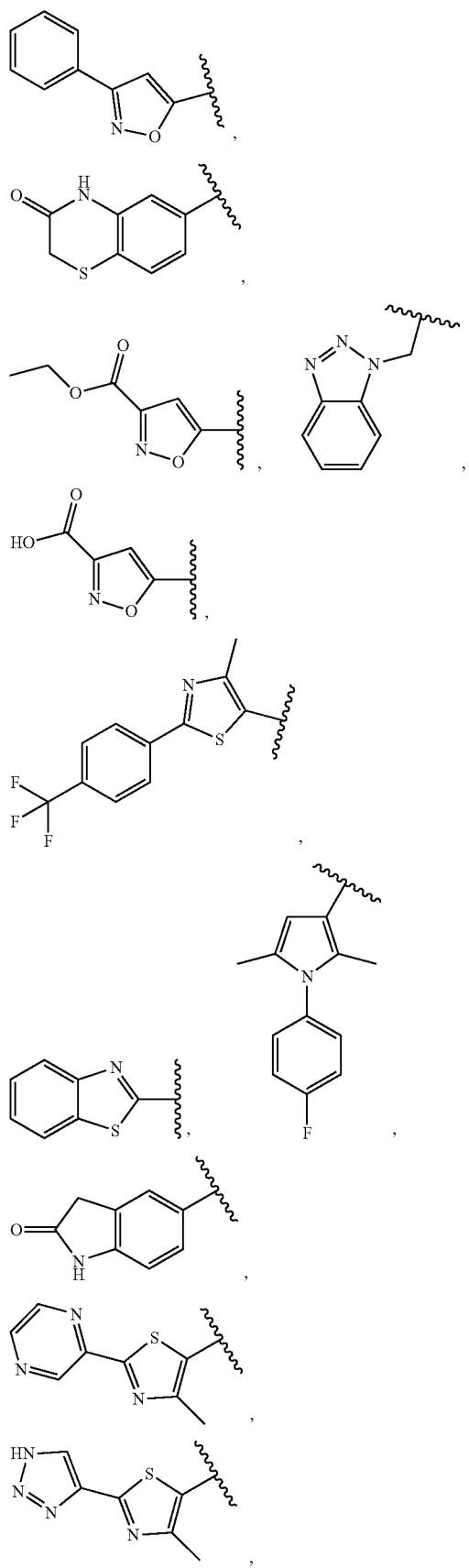
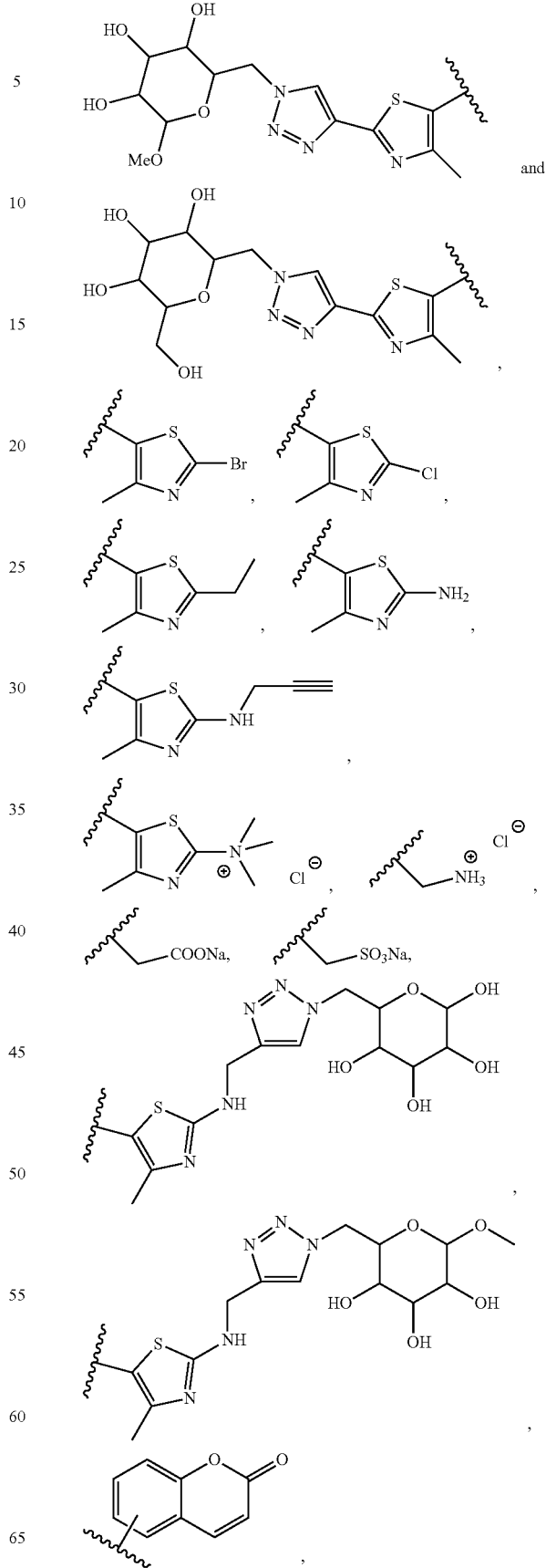

107
-continued
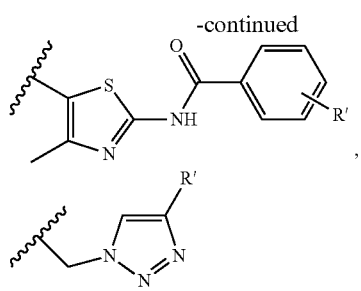
with R' as defined in claim 1.
10. The compound of claim 1, wherein it is selected from:
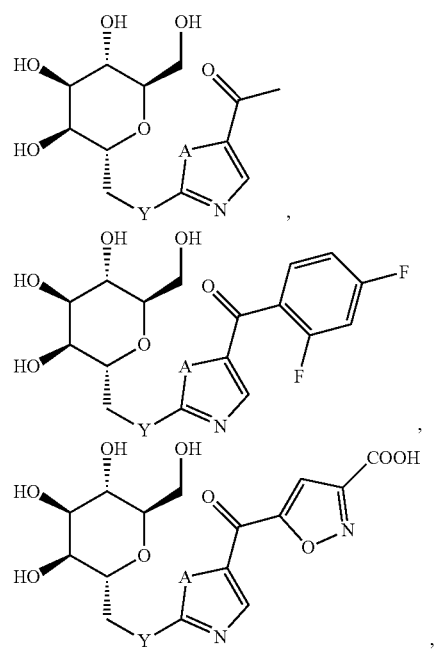
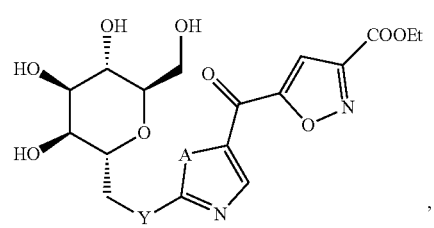
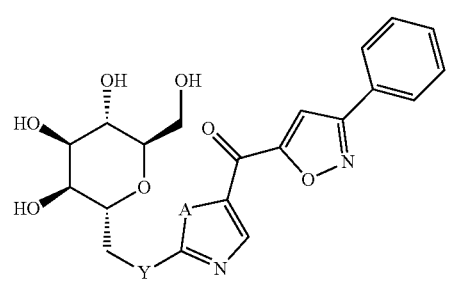
108
-continued
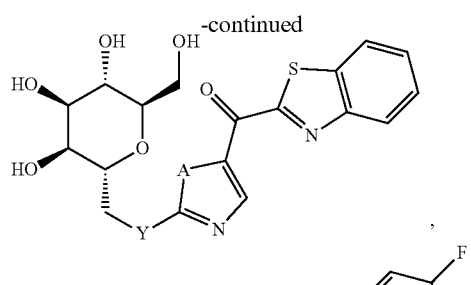
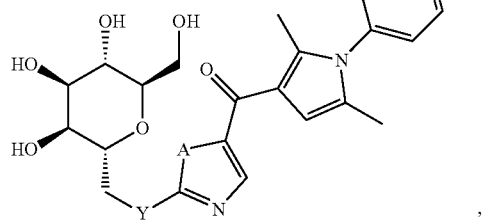
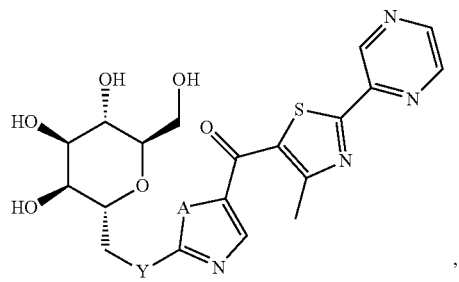
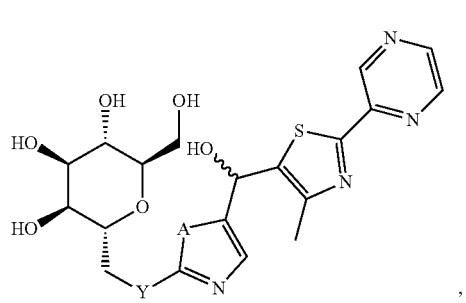
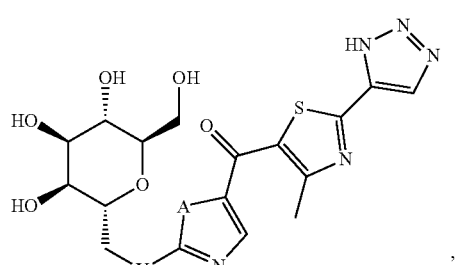
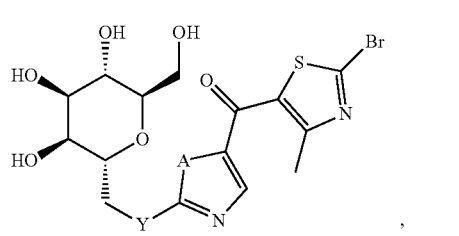

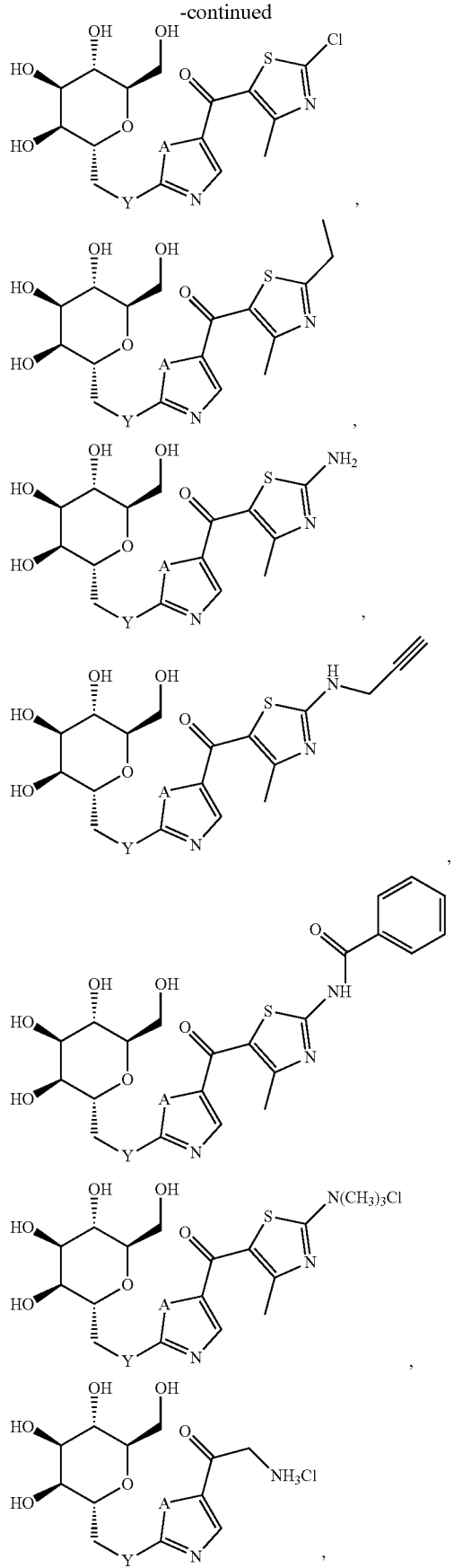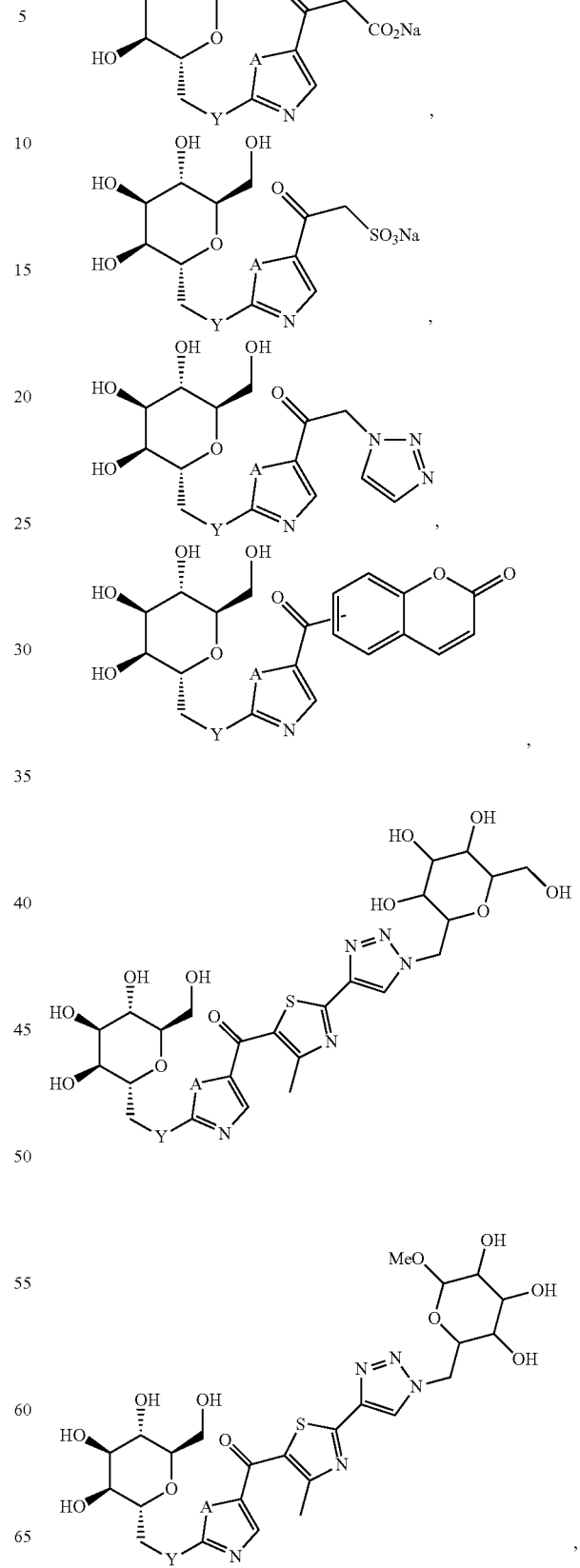

-continued

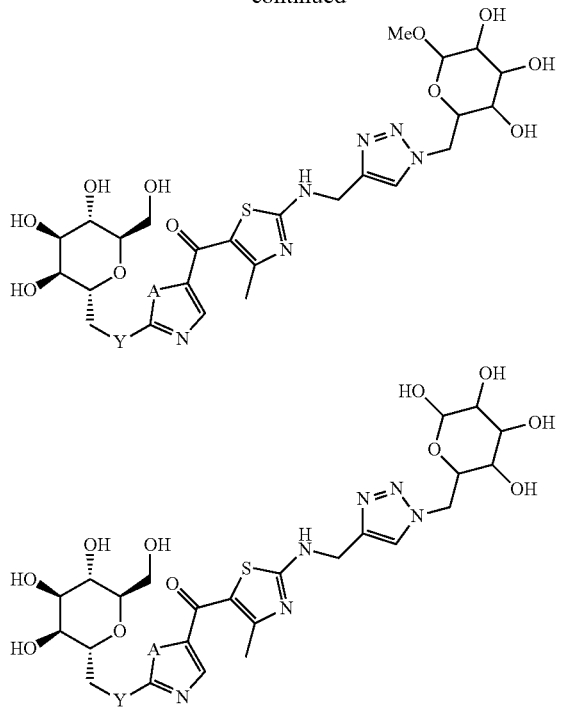

wherein A is as defined in claim 1,
and wherein Y is as defined in claim 1.

11. A pharmaceutical composition comprising the compound of claim 1 as active substance, and a pharmaceutically acceptable carrier.

12. The pharmaceutical composition of claim 11, further comprising another therapeutic compound.

13. The compound of claim 1, wherein T is an alkaline cation and T' is a halogenide.

14. The compound of claim 1, wherein T is Na$^+$ and T' is chloride.

15. The compound of claim 10, wherein A is S and Y is a single bond or NH.

16. A method for treating pathologies caused by Adherent *Escherichia coli* and mediated by interactions between Adherent *Escherichia coli* lectins and host cell surface glycans, comprising administering to a subject in need thereof an effective amount of the compound of claim 1 or the composition of claim 11.

17. The method of claim 16, wherein said pathologies are:
an inflammatory bowel disease, including Crohn's disease;
a urinary tract infection, including painful bladder syndrome and cystitis,
an irritable bowel syndrome;
a metabolic disease including metabolic syndrome, obesity, diabetes, hypercholesterolemia;
autoimmune inflammatory diseases including Berger's disease, Graves' disease, Hashimoto's thyroiditis, the primary myxedema, celiac disease, ulcerative colitis, Crohn's disease, rheumatoid arthritis, primary biliary cirrhosis, primary sclerosing cholangitis, the autoimmune hemolytic anemia, pernicious anemia (pernicious anemia), lupus erythematosus, CREST syndrome, type 1 diabetes, scleroderma, pemphigus vulgaris, pemphigoid oily, the epidermolysis Bullosa acquired, dermatitis herpetiformis, myasthenia, Lambert-Eaton myasthenic syndrome, polymyositis, Sjögren's syndrome, multiple sclerosis, rheumatoid arthritis, Grave's disease and psoriasis; and
colorectal cancer, including colon cancer.

18. The method of claim 16, further comprising a second composition comprising another therapeutic compound in a simultaneous, separate or staggered way.

19. The method of claim 16 for treating Crohn's disease or colitis in a mammal.

20. The method of claim 16, wherein Adherent *Escherichia coli* lectins are FimH adhesin.

* * * * *